US006455250B1

(12) United States Patent
Aguilera et al.

(10) Patent No.: US 6,455,250 B1
(45) Date of Patent: Sep. 24, 2002

(54) ENDONUCLEASE COMPOSITIONS AND METHODS OF USE

(75) Inventors: Renato J. Aguilera, Culver City; Christopher J. Lyon, Los Angeles, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/210,422

(22) Filed: Dec. 11, 1998

Related U.S. Application Data

(60) Provisional application No. 60/069,205, filed on Dec. 11, 1997.

(51) Int. Cl.[7] .......................... C12Q 1/68; C12P 21/06; C12N 5/00; C07H 21/04; A01N 63/00
(52) U.S. Cl. ....................... 435/6; 435/69.1; 435/320.1; 435/325; 435/455; 435/456; 424/93.2; 424/93.21; 536/23.2; 536/23.5
(58) Field of Search ...................... 435/4, 6, 69.1, 435/70.1, 455, 325, 349, 352, 350, 353, 363, 366, 456; 536/23.1, 23.2; 800/8, 9, 13

(56) References Cited

U.S. PATENT DOCUMENTS 5,200,313 A * 4/1993 Carrico .......................... 435/6

FOREIGN PATENT DOCUMENTS

| EP | 0307247 | * 3/1989 |
| EP | 0721012 | * 7/1996 |
| WO | 9740134 | * 10/1997 |

OTHER PUBLICATIONS

Hillier et al., GenCore, GenBank Acc. No. H12842, accessed by the USPTO on Jul. 3, 2000, Jun. 27, 1995.*
McCoubrey et al., GenCore, GenBank Acc. No. U05013, accessed by the USPTO, on Jul. 3, 2000, Jun. 21, 1994.*
Turley et al., GenCore, GenBank Acc. No. A49936, accessed by the USPTO on Jul. 3, 2000, Mar. 7, 1997.*
Marra et al., GenCore, GenBank Acc. No. AA546141, accessed by the USPTO on Jul. 3, 2000, Aug. 5, 1997.*
Marra et al., GenCore, GenBank Acc. No. AA276783, accessed by the USPTO on Jul. 3, 2000, Apr. 1, 1997.*
Marra et al., GenCore, GenBank Acc. No. AA645623, accessed by the USPTO on Jul. 3, 2000, Oct. 28, 1997.*
Marra et al., GenCore, GenBank Acc. No. W14976, accessed by the USPTO on Jul. 3, 2000, Sep. 10, 1996.*
Palmiter et al., Proc. Natl. Acad. Sci., USA, 88:478–482, 1991.*
A. Colman, Am. J. Clin. Nutr., 63:639S–645S, 1996.*
R.J. Wall, Theriogenology, 45:57–68, 1996.*
Aguilera et al., "Characterization of immunoglobulin enhancer deletions in murine plasmacytomas,", *EMBO J.*, 4:3689–3693, 1985.

Ainscough, "Hypothetical protein K04H4.6—Caenorhabditis elegans," EMBL Data Library from the internet at website: http://www.ncbi.nlm.nih.gov/htbin–post/Entrez/query?uid=482203&form=6&db=p&Dopt=g.
Baker et al., "Molecular cloning and characterization of human and murine Dnase II, " *Gene*, 215:281–289, 1998.
Brown et al., "Regulation of the RAG–1 promoter by the NF–Y transcription factor," *J. Immunol.*, 158:5071–5074, 1997.
Czene et al., "pH dependent DNA cleavage in permeabilized human fibroblasts," *Biochem. J.*, 323:337–341, 1997.
Hope et al., "Endonucleolytic activity that cleaves immunoglobulin recombination sequences," *Sci.*, 231:1141–1145, 1986.
Lamerdin et al., "Homo Spaiens DNA from chromosome 19p13.2 cosmids R31240, R30272 and R28549 containing the EKLf, GCDH, CRTC, and RAD23A genes, genomic sequence," EMBL Data Library from the internet at website: http://www.ncbi.nlm.nih.gov/htbin–post/Entrez/query?uid=1905905&form=6&db=n&Dopt=g.
Lyon and Aguilera, "Purification and characterization of the immunoglobulin switch sequence–specific endonuclease (Endo–SR) from bovine spleen," *Molecular Immunology*, 32(3):209–219, 1997.
Lyon et al., "Characterization of an endonuclease activity which preferentially cleaves the G–rich immunoglobulin switch repeat sequences," *Mol. Immunol.*, 33(2):157–169, 1996.
Lyon, "Characterization of a candidate switch endonuclease activity, " *A dissertation submitted in partial satisfaction of the requirement for the degree Doctor of Philosophy in Molecular Biology*, 1997.
Marra et al., "mb35ho6.r1 Soares mouse p3NMF19.5 Mus musculus cDNA clone IMAGE:331451 5', mRNA sequence, " EMBL Data Library from the internet at website:http://www.ncbi.nlm.nih.gov/htbin–post/Entrez/query?uid=1288999&form=6&db=n&Dopt=g.
Miranda et al., "The murine nucleolin protein is an inducible DNA and ATP binding protein which is ready detected in nuclear extracts of lipopolysaccharide–treated splenocytes," *Exp. Cell Res.*, 217:294–308, 1995.
Vassilatis et al., "Analysis of a 43–kDa glycoprotein from the intracellular parasitic nematode *Trichinella spiralis*, " *J. Biol. Chem.*, 267(26):18459–65, 1992.

* cited by examiner

*Primary Examiner*—Scott D. Priebe
*Assistant Examiner*—Shin–Lin Chen
(74) *Attorney, Agent, or Firm*—Mandel & Adriano

(57) ABSTRACT

Disclosed are methods for modulating apoptosis and altering programmed cell death events using novel Endo-SR gene compositions and the polypeptides encoded thereby. Also disclosed are methods for repairing DNA, modulating genetic recombination in a cell, and altering DNA rearrangement in a host cell. Also disclosed are methods for the design and isolation of peptidomimetics and other inhibitors of Endo-SR useful in the treatment of leukemias, lymphomas, and other cancers.

16 Claims, 7 Drawing Sheets

Figure 1:
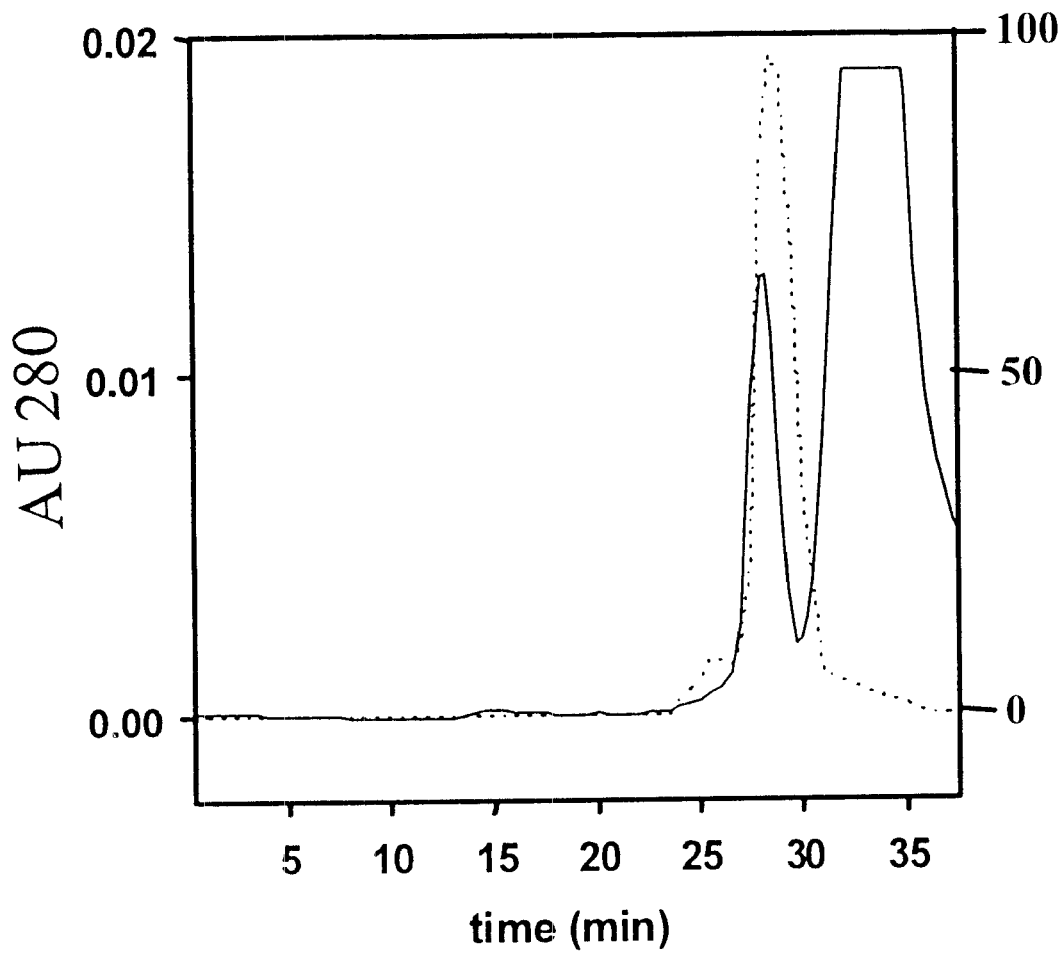

| Peptide 1 | QLAFVLYNDQPXK | (Seq ID NO:13) |
|---|---|---|
| | SQLAFVLYND | (Seq ID NO:14) |
| Peptide 2 | YGRGHTKGVLLLDQEGGFL | (Seq ID NO:15) |
| | SXHRGHTK | (Seq ID NO:16) |
| Peptide 3 | KQLTYTYMLV | (Seq ID NO:17) |

FIG. 7

```
                                  SEQUENCE LISTING

<160> NUMBER OF SEQ ID NOS:  17

<210> SEQ ID NO 1
<211> LENGTH: 636
<212> TYPE: DNA
<213> ORGANISM: Musca sp.

<400> SEQUENCE: 1
atggcaacac tgagatcgct gctgctggct gcgctgctgt gggtccctgc cgaagccctg         60
agctgctatg gggactccgg gcagcctgtg gattggttcg tggtatacaa gctgccggct        120
cacagcgggt ctagggatac tccaaaggga ctgacgtgta aatacatgga ccagaactcc        180
gacggttggc aagacggtgt agggtacatc aacagcccgg agggagccgt gggccgcagc        240
ttgcagccat tgtaccgaaa gaactccagc cagctggcct ttctactcta caacgaccaa        300
cctcctaaat ccagctcaac tcgggactct accggccatg gcatacgaa  gggcaagcag        360 ctaacctaca cctatcccct tgtctatgac cacaagctgg aaggcttctt cgctcagaaa        420
ttaccctaca cctatcccct tgtctatgac cacaagctgg aaggcttctt cgctcagaaa        480
ttacctgacc tagagacggt gatcaagaac caacatgtcc tccatgagcc ctggaatagc        540
agtgtaatac tcacttccca agctggggcc accttccaga gctttgccaa atttggaaaa        600
tttggagatg acctgtactc cggatggttg gcagaa                                  636

<210> SEQ ID NO 2
<211> LENGTH: 192
<212> TYPE: PRT
<213> ORGANISM: Musca sp.

<400> SEQUENCE: 2

Met Ala Thr Leu Arg Ser Leu Leu Ala Ala Leu Leu Trp Val Pro
  1               5                  10                  15

Ala Glu Ala Leu Ser Cys Tyr Gly Asp Ser Gly Gln Pro Val Asp Trp
                 20                  25                  30

Phe Val Val Tyr Lys Leu Pro Ala His Ser Gly Ser Arg Asp Thr Pro
             35                  40                  45

Lys Gly Leu Thr Cys Lys Tyr Met Asp Gln Asn Ser Asp Gly Trp Gln
     50                  55                  60

Asp Gly Val Gly Tyr Ile Asn Ser Pro Glu Gly Ala Val Gly Arg Ser
 65                  70                  75                  80

Leu Gln Pro Leu Tyr Arg Lys Asn Ser Ser Gln Leu Ala Phe Leu Leu
                 85                  90                  95

Tyr Asn Asp Gln Pro Pro Lys Ser Ser Thr Arg Asp Ser Thr Gly
            100                 105                 110

His Gly His Thr Lys Gly Lys Gln Leu Thr Tyr Thr Tyr Pro Leu Val
            115                 120                 125

Tyr Asp His Lys Leu Glu Gly Phe Phe Ala Gln Lys Leu Pro Asp Leu
        130                 135                 140
```

```
Glu Thr Val Ile Lys Asn Gln His Val Leu His Glu Pro Trp Asn Ser
145                 150                 155                 160

Ser Val Ile Leu Thr Ser Gln Ala Gly Ala Thr Phe Gln Ser Phe Ala
                165                 170                 175

Lys Phe Gly Lys Phe Gly Asp Asp Leu Tyr Ser Gly Trp Leu Ala Glu
            180                 185                 190
```

<210> SEQ ID NO 3
<211> LENGTH: 802
<212> TYPE: DNA
<213> ORGANISM: Musca sp.
<220> FEATURE:
<221> NAME/KEY: misc_feature
<222> LOCATION: (638)..(797)
<223> OTHER INFORMATION: n = c, g, a, or t

<400> SEQUENCE: 3

| | | | | | |
|---|---|---|---|---|---|
| atggcaacac | tgagatcgct | gctgctggct | gcgccgctgt | gggtcctgcc | cgaagccctg | 60 |
| agctgctatg | gggactccgg | gcagcctgtg | gattggtgag | taagtagtcg | cgggactgtc | 120 |
| ccccgcacac | tgcctgggga | ccggcgcggg | aatccaaaaa | acctcagatt | ccttttctct | 180 |
| cccaacctca | tgtcttcacg | gacctccagg | ttcgtggtat | acaagctgcc | ggctcacagc | 240 |
| gggtctaggg | atactccaaa | gggactgacg | tataaataca | tggaccaaaa | ctccgacgga | 300 |
| tggcaagacg | gtgtagggta | tatcaacagc | tcggagggag | ccgtgggccg | cagcttgcag | 360 |
| ccattgtacc | gaaagaactc | cagccaggtg | acttgagtgc | cttcggaacc | cgggccggga | 420 |
| cactgtggtg | ggtctcgccg | ggaagggaag | gtagttacat | agcctctgtg | cattctccta | 480 |
| gctggccttt | ctactctaca | cgaccaacc | tcctaaatcc | agctcagctc | gggactctac | 540 |
| cggccatggg | catacaaagg | gtgagaagct | tggactggtg | gtcctggaac | ctccctgaat | 600 |
| tgtaaatttt | accctcacta | accttccgcc | tgatgaaagg | tggggatttg | cctgtcctgg | 660 |
| nctccgtttc | tcgctctaaa | acccanccat | ctgangcccc | tacctgcttg | cangttaact | 720 |
| aacttgacnc | tncctccggt | tcaggttttc | ctgcnccctga | acaaaaaagg | ggnttctggc | 780 |
| ttgttcccan | tntnccncc | tc | | | | 802 |

<210> SEQ ID NO 4
<211> LENGTH: 1582
<212> TYPE: DNA
<213> ORGANISM: Musca sp.
<220> FEATURE:
<221> NAME/KEY: misc_feature
<222> LOCATION: (725)
<223> OTHER INFORMATION: n = c, g, a, or t

<400> SEQUENCE: 4

| | | | | | |
|---|---|---|---|---|---|
| gtccttcccg | ttcactcagt | ttgcaaggat | tggtgagttg | aatcactgag | aagccaagct | 60 |
| tcaaattctt | ctgaggaacc | agtctcacac | ggctccctcg | ccttgtcttc | taggcaagca | 120 |
| gctaacctac | acctatcccc | ttgtctatga | ccacaagctg | gaaggcttct | tcgctcagaa | 180 |
| attacctgac | ctagagacgg | tgatcaagaa | ccaacatgtc | ctccatgagc | cctggaatag | 240 |
| cagtgtaata | ctcacttccc | aagctggggc | caccttccag | agctttgcca | aatttggaaa | 300 |
| atttggagat | ggtaagcctt | gatgttgagg | ggtgggggga | gggcactttc | gttgtagaag | 360 |
| ggggtcccta | gtatccctag | gcctgcgggc | aacacattta | gagcccagat | gtctttggga | 420 |
| gtcatattac | aataataact | atgagcagta | acagccagc | agacggggttg | ggcgggtgat | 480 |
| acatatctgt | gacctcagca | ctgtgggggc | ggagatggaa | gcttgaagtc | agccaacaga | 540 |

```
cctaggttca aatgttggtt tctggatgtg taatatacaa tacaacctga gcctgtttgc    600
tcacctgaaa aattaggata ttaagggttc ccttagtggg ttgtgaaata acacataatt    660
gtttggtaag gattcccttt aggggtgtgg ggaggcgggc cctcactgtg tatccctggc    720
tggtntggaa ctctcagaga gccatctgcc tctactgtct cagcgcagac tttaaaggct    780
tgagtctcca tgcccagcct atgtgtttgt gtaagacctc tttacattcc aggctagact    840
ccatctgaga gcctcttgtt ccagttttg agtgttaggg ctgcaggtgg acctggagag    900
ggacctgacc tgttataggg gctgcttagg ttcacgtcat tccaaagtag aacatttgag    960
cggagcagga gccataccga ggaatgtacc agtgcccttc acttcatctt tctttcccct   1020
gcagacctgt actccggatg gttggcagaa gcccttggca ccaacctaca ggtccagttc   1080
tggcaaaatt ctccaggcat cctgccctcc aactgctctg gagcctatca ggttctggat   1140
gtgacacaga caggattccc tggcccatct agactaactt tcagtgccac agaggaccac   1200
tccaaatggt gtgtggcccc tcaagggccc tgggcctgtg tgggtgacac gaataggaac   1260
aaagcagaga cacaccgagg tgcggcacag gtatgcaccc aactgccttc cttttggaag   1320
gccttccagt ccctggtgaa agactggaaa ccctgtatag aggggagctg actgaagccc   1380
atcggagcaa aggactaaga ctccgcagtc taaccaggtg ggggccggac tagcctttac   1440
cccagcactt gggaagcaga agcaggtgga tcgattctct ctctctctct ggttttccga   1500
gacagggttt ctctgtgtta cccttggctg tcctggaaac tcactctgta gaacaaggcc   1560
tgggcctcca actccaaatc tg                                            1582
```

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic

<400> SEQUENCE: 5
ctagagctgg ggtgagctga gctgagct                                        28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic

<400> SEQUENCE: 6
ctagagctca gctcagctca ccccagct                                        28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic

<400> SEQUENCE: 7
ctagagctga gctgagctga gctgagct                                        28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic

<400> SEQUENCE: 8
ctagagctca gctcagctca gctcagct                                      28

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic

<400> SEQUENCE: 9
tggggtgagc tgca                                                     14

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: Synthetic

<400> SEQUENCE: 10
gctcacccca gtac                                                     14

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 11
tggggtgagc tgagctgagc                                               20

<210> SEQ ID NO 12
<211> LENGTH: 20
<212> TYPE: DNA
<213> ORGANISM: Bovidae

<400> SEQUENCE: 12
tgagctgagc tgagctgagc                                               20

<210> SEQ ID NO 13
<211> LENGTH: 20
<212> TYPE: PRT
<213> ORGANISM: Bovidae

<400> SEQUENCE: 13

Thr Gly Ala Gly Cys Thr Gly Ala Gly Cys Thr Gly Ala Gly Cys Thr
 1               5                  10                  15
Gly Ala Gly Cys
            20

<210> SEQ ID NO 14
<211> LENGTH: 10
<212> TYPE: PRT
<213> ORGANISM: Bovidae

<400> SEQUENCE: 14

Ser Gln Leu Ala Phe Val Leu Tyr Asn Asp
 1               5                  10

<210> SEQ ID NO 15
<211> LENGTH: 19

-continued

```
<212> TYPE: PRT
<213> ORGANISM: Bovidae

<400> SEQUENCE: 15

Tyr Gly Arg Gly His Thr Lys Gly Val Leu Leu Leu Asp Gln Glu Gly
 1               5                  10                  15

Gly Phe Leu

<210> SEQ ID NO 16
<211> LENGTH: 8
<212> TYPE: PRT
<213> ORGANISM: Bovidae
<220> FEATURE:
<221> NAME/KEY: PEPTIDE
<222> LOCATION: (2)
<223> OTHER INFORMATION: X = any

<400> SEQUENCE: 16

Ser Xaa His Arg Gly His Thr Lys
 1               5

<210> SEQ ID NO 17
<211> LENGTH: 10
<212> TYPE: PRT
<213> ORGANISM: Bovidae

<400> SEQUENCE: 17

Lys Gln Leu Thr Tyr Thr Tyr Met Leu Val
 1               5                  10
```

ENDONUCLEASE COMPOSITIONS AND METHODS OF USE

This application claims priority under 35 U.S.C. 119 (e) of provisional U.S. patent application Ser. No. 60/069,205, filed Dec. 11, 1997.

The United States government has rights in the present invention pursuant to Grants MCB-9316981 and MCB-9316982 from the National Science Foundation.

1.0 BACKGROUND OF THE INVENTION

1.1 Field of the Invention

The present invention relates generally to the fields of immunology and oncology. Disclosed are compositions comprising nucleotide sequences encoding endonuclease SR, and polypeptides encoded thereby. Also disclosed are methods for repairing DNA and modulating genetic recombination in a cell, particularly through the use of a specific endonuclease, which is referred to hereinafter as Endo-SR (Endonuclease implicated in Switch Recombination). The compositions disclosed are useful in cleaving DNA at specific G-rich regions which are implicated in modulating DNA rearrangements. Also disclosed are methods for the design and isolation of peptidomimetics and Endo-SR inhibitors useful in the treatment of leukemias, lymphomas, and other cancers, as well as modulation of apoptosis and programmed cell death events.

1.2 Description of Related Art

1.2.1 B-Lymphocytes

Mature B lymphocytes can alter their Ig isotype expression by targeted deletional rearrangement of their IgH constant region genes in a process called isotype switch recombination (Harriman et al., 1993; Shimizu and Honjo, 1984). The ability of B cells to "switch" one Ig constant region for another significantly enhances the versatility of the immune system by allowing activated B cells to selectively alter the function of their secreted Ig without altering their ligand specificity (Esser and Radbruch, 1990; Mond et al., 1995a, b).

Recombination breakpoints generated by this process primarily map to large (approximately 1 to 10 kb), highly-repetitive DNA regions found upstream of all IgH constant region genes (Esser and Radbruch, 1990; Harriman et al., 1993). These switch regions are primarily composed of degenerate, variable-length G-rich repeat units, that differ considerably both within and between species (Esser and Radbruch, 1990; Harriman et al., 1993). However, all switch regions contain disproportionate numbers of two pentamer motifs, TGGGN and TGAGC, that are found at or adjacent to most analyzed switch recombination breakpoints (Dunnick et al., 1993; Mowatt et al., 1986; Kenter et al., 1993, Petrini and Dunnick, 1989; Wuerffel et al., 1992).

Selective recombination of individual switch regions directly correlates with transcriptional activation of these regions in response to extracellular signals (Berton and Vitetta, 1990; Bottaro et al., 1994; Kuwabara et al., 1995; Rothman et al., 1990; Warren and Berton, 1995; Xu et al., 1993; Xu and Stavnezer, 1992). Recent studies have demonstrated that an additional signal(s) is required to induce switch recombination at an actively transcribed switch region (Bottaro et al., 1994). Specific transcriptional induction has thus been proposed to increase the accessibility of a particular switch region to switch recombinase factors, which may also be activated by some of the same signals responsible for transcriptional activation of these loci (Mandler et al, 1993; Purkerson and Isakson, 1992; Snapper and Mond, 1993).

The search for switch recombinase factors has primarily focused on the detection of DNA binding factors which specifically interact with switch repeat sequences, and although this approach has lead to the characterization of several novel DNA binding factors (Fukita et al., 1993; Marcu et al., 1992; Miranda et al., 1995; Mizuta et al., 1993; Waters et al., 1989; Wuerffel et al., 1990; Xu et al., 1992), as yet none of these factors have been directly implicated in the switch recombination reaction.

2.0 SUMMARY OF THE INVENTION

The present invention overcomes limitations in the prior art by providing novel endonuclease polypeptides, and in particular, mammalian Endo-SR polypeptides which have specific endonuclease activity. In a preferred embodiment, the Endo-SR polypeptide is isolated from mammalian sources, including murine, bovine, and human sources, or from organisms such as C. elegans and the like, and comprises at least a 19-contiguous amino acid sequence from SEQ ID NO:2. More preferably, the polypeptide comprises the amino acid sequence of SEQ ID NO:2, and is encoded by a polynucleotide that comprises at least a 76-contiguous nucleic acid sequence from SEQ ID NO:1, and preferably comprising the sequence of SEQ ID NO: 1. Exemplary murine genomic DNA sequences include sequences such as those in SEQ ID NO:3 and SEQ ID NO:4. Preferred sequences include sequences comprising at least 49 contiguous nucleic acid sequences from SEQ ID NO:3, and sequences comprising at least 24 contiguous nucleic acid sequences from SEQ ID NO:4. Sequences comprising at least 204 contiguous nucleic acids from SEQ ID NO:4 are also contemplated to be particularly useful.

The Endo-SR polypeptides of the present invention preferentially cleave either a "TGGGN" or a "TGAGC" polynucleotide sequence, and more preferably cleave both of these sequences, which are known as "switch pentamer motifs" at or near recombination breakpoints. These polypeptides have been shown to be enriched in lymphoid tissue nuclear extracts.

In one important embodiment, the invention provides an isolated and purified amino acid segment comprising Endo-SR polypeptide comprising the amino acid sequence of SEQ ID NO:2. This polypeptide is a murine polypeptide, the coding region for which is given in SEQ ID NO:1 (a cDNA clone). The corresponding murine genomic DNA sequences are given in SEQ ID NO:3 and SEQ ID NO:4. The Endo-SR polypeptide exhibits specific endonuclease activity for G-rich DNA sequences. In related embodiments, methods for making and using this protein, derivatives and mutants thereof, and antibodies directed against these proteins are also disclosed. Also disclosed are methods for the design of inhibitors, such as peptidomimetics, of Endo-SR, and their use in modulation of Endo-SR activity.

In another important embodiment, the invention provides an isolated and purified nucleic acid segment comprising the mammalian gene which encodes the Endo-SR polypeptide disclosed herein. The nucleotide sequence of the cDNA is given in SEQ ID NO:1, and the partial murine genomic sequences are identified in SEQ ID NO:3 and SEQ ID NO:4. In related embodiments, methods for making, using, altering, mutagenizing, assaying, and quantitating these nucleic acid segments are also disclosed. Also disclosed are diagnostic methods and assay kits for the identification and detection of related gene sequences in a variety of in vitro and in vivo methodologies. Because Endo-SR has been implicated in the process of antibody isotype switch recombination and programmed cell death, highly purified or recombinant Endo-SR represents a useful tool for dissection of the mechanism of switch recombination and/or apoptosis.

Another aspect of the present invention is a mammalian cell, and in particular, a bovine or human cell that produces the novel Endo-SR polypeptide disclosed herein. Exemplary mammalian cells that produce the polypeptide include human HeLa and 293T kidney cells as well as mouse L-cell and NIH3T3.

A further aspect of the present invention is a vector, such as a plasmid, cosmid, phage, virus, phagemid, bacterial artificial chromosome or yeast artificial chromosome, that contains a nucleic acid sequence comprising a whole or a portion of a gene encoding Endo-SR (cDNA, SEQ NO ID:1; genomic clones, SEQ ID NO:3 and SEQ ID NO:4). Also provided is a transformed host cell comprising a native or recombinant gene encoding Endo-SR, as well as a tissue culture, a cell culture, or an animal, fungal or bacterial cell culture or suspension or lysate of a host cell transformed with such a vector.

The invention also provides a pharmaceutical composition comprising an Endo-SR polypeptide or a gene encoding such a polypeptide.

Because moderate levels of enzymatically active Endo-SR have been detected in animal serum and the Endo-SR is secreted, the polypeptide may play a role in preventing DNA accumulation in blood and tissues. Monoclonal or polyclonal antibodies directed towards the Endo-SR protein and/or Endo-SR peptides may prove to have therapeutic potential for patients carrying Endo-SR mutations resulting in elevated secretion of this protein. Alternatively, anti-Endo-SR antibodies may prove useful in the detection and diagnosis of patients with elevated or repressed levels of this enzyme. Therefore, in one embodiment, there is provided a monoclonal antibody that binds immunologically to an Endo-SR polypeptide. The antibody preferably is a mammalian antibody, and is non-cross-reactive with other mammalian polypeptides. Alternatively, the antibody may bind specifically to either human, or non-human Endo-SR polypeptides, but not to both human and non-human Endo-SR polypeptides. The antibody may further comprise a detectable label, such as a fluorescent label, a chemiluminescent label, a radiolabel or an enzyme. Also encompassed are hybridoma cells and cell lines producing such antibodies.

In another embodiment, there is included a polyclonal antisera, antibodies of which bind immunologically to an Endo-SR polypeptide. The antisera may be derived from any animal, but preferably is from an animal other than a human. Preferred antigens for the preparation of such sera include an Endo-SR polypeptide from human, bovine, murine, or other mammalian origins. A preferred host for the polyclonal antisera is preferably rabbit, goat, or other such animal. In an illustrative embodiment, rabbit polyclonal antisera raised against a recombinant human Endo-SR protein fragment was generated and shown to specifically recognize the immunizing antigen. The immunogen was generated from a Endo-SR gene fragment representing exons 5–6 of the human coding sequence cloned into the pET15b™ expression vector (Novagen), which was subsequently expressed and purified from bacteria.

It also is an objective of the present invention to provide methods for making and using the Endo-SR compositions disclosed herein, and also for using the genes which encode them.

For example, the invention provides a method of obtaining an Endo-SR polypeptide from a mammalian cell. Endo-SR/DNase II activity was purified to homogeneity or near homogeneity from both mammals and C. elegans nematodes in a procedure in which crude protein extracts are selectively fractionated by successive ammonium sulfate precipitation, isoelectric focusing, cation-exchange chromatography, and size exclusion chromatography (essentially as per Lyon and Aguilera, 1997). Nuclear extracts are used as the starting material in Endo-SR purification from mammalian cell lines and tissues, while purification of the nematode enzyme begins with whole cell extracts. Endo-SR activity has been detected in cytoplasmic and nuclear extracts of all assayed tissues and cell lines.

Nuclease assays have demonstrated that, among the tissues tested, spleen contains the most Endo-SR specific activity, followed by thymus and liver. Spleen tissue was used as the source material for purification of the bovine enzyme due to its preferential enrichment in this activity. Endo-SR activity has also been detected at variable levels in all human and murine cell lines assayed to date and therefore this activity may be isolated from such cell lines essentially as previously described (Lyon, et al., 1996).

In another embodiment, there is provided a method of producing the Endo-SR polypeptide from a host cell transformed with one or more DNA sequences encoding the polypeptide. Such preparation is typically referred to in the art as "large-scale" or "recombinant" protein production. In an exemplary method, the polypeptides of the present invention may be produced by a method that generally comprises:

Large amounts of Endo-SR protein could most efficiently be generated from a cell line containing an integrated Endo-SR expression vector. Endo-SR activity has been overexpressed by transient and stable transfection of mammalian cell lines with expression vector constructs. Since prolonged Endo-SR overexpression reduces cell viability, stable transfectants have been produced using the Tet-Off™ (Clontech) system. Recombinant genes under the control of this system are expressed only in the absence of inhibitory concentrations of tetracycline and recombinant protein expression can be modulated by varying the concentration of tetracycline in the culture media. Since the Endo-SR protein contains a leader sequence and has been shown to be secreted from the cell, it is possible that recombinant protein will be easily isolated from cell supernatants in serum-free media. Other human (such as HeLa and 293T kidney cells) and mouse (such as L-cell, NIH3T3, or other cell lines) may also be used to obtain cell types that permit optimal high-level production of this enzyme in culture.

In another embodiment, there is provided a method of cleaving a polynucleotide such as DNA. This method generally involves contacting a polynucleotide that comprises at least one "TGGGN" or one "TGAGC" sequence with an amount of an Endo-SR polypeptide composition effective to cleave such polynucleotide.

In a further embodiment, there is provided a method for killing a tumor comprising the step of contacting a tumor cell within a subject with a therapeutically-effective amount of an Endo-SR polypeptide compositions. Preferably, the tumor cell is within a mammal such as a human.

In still a further embodiment, there is provided a method for treating cancer comprising the step of contacting a tumor cell within a subject with a nucleic acid (a) encoding an Endo-SR polypeptide and (b) a promoter operable in the tumor cell, wherein the promoter is operatively linked to the region encoding the Endo-SR polypeptide, under conditions permitting the uptake of the nucleic acid by the tumor cell. The subject is preferably an animal, and most preferably a human.

In still yet a further embodiment, there is provided a transgenic mammal in which both genomic copies of the gene encoding an Endo-SR polypeptide are interrupted, deleted, or replaced with at least one other gene or gene fragment. Such an animal is typically referred to as an Endo-SR "knockout" animal. Such animals are contemplated to be excellent models for gene therapy/DNA vaccines as they may allow DNA based vectors to efficiently integrate into the host genome. The mammal is preferably murine, porcine, ovine, epine, lupine, equine, bovine, caprine, canine, or feline.

In still yet an additional embodiment, there is provided a method of screening a candidate substance which inhibits Endo-SR activity in a cell. This method generally comprises (a) providing a cell having functional Endo-SR polypeptide activity; (b) contacting the cell with the candidate substance; and (c) determining the inhibitory effect of the candidate substance on the Endo-SR activity in the cell. The candidate substance may be a chemotherapeutic or radiotherapeutic agent or be selected from a small molecule library, or alternatively, a peptidomimetic which inhibits Endo-SR activity. Endo-SR inhibition may result in similar effect as the mutation of the gene in animals. The cell may be contacted in vitro or in vivo.

The foregoing objects of the invention and others that are now readily apparent to those of skill in the art having the benefit of the present disclosure are described more fully in the sections which follow:

2.1 Polynucleotide Compositions

The present invention also concerns polynucleotide segments, (including DNA, RNA, and PNAs) that can be isolated from virtually any source, that are free from total genomic DNA and that encode the whole or a portion of the novel endonuclease disclosed herein. The gene having the nucleotide sequence of SEQ ID NO:1 encodes the murine Endo-SR polypeptide having an amino acid sequence shown in SEQ ID NO:2. DNA segments encoding this polypeptide may be used to identify additional DNA sequences, that may encode proteins, polypeptides, subunits, functional domains, and the like of Endo-SR-related or other non-related gene products. In addition these DNA segments may be synthesized entirely in vitro using methods that are well-known to those of skill in the art.

As used herein, the term "DNA segment" refers to a DNA molecule that has been isolated free of total genomic DNA of a particular species. Therefore, a DNA segment encoding an Endo-SR polypeptide refers to a DNA segment that contains an Endo-SR polypeptide coding sequence yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, BACs, YACs, viruses, and the like. In one embodiment, the inventors have constructed BAC genomic clones which find important utility in the generation of "knockout" animals.

Similarly, a DNA segment comprising an isolated or purified Endo-SR polypeptide-encoding gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes not only genomic sequences, including extra-chromosomal DNA sequences, but also promoter or cis acting sequences and/or engineered gene segments that express, or may be adapted to express one or more proteins, polypeptides or peptide fragments.

"Isolated substantially away from other coding sequences" means that the gene of interest, in this case, an Endo-SR polypeptide-encoding gene, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

In particular embodiments, the invention concerns isolated polynucleotides and recombinant vectors incorporating polynucleotide sequences that encode all or part of an Endo-SR polypeptide species that includes within its amino acid sequence an at least 19 contiguous amino acid sequence from SEQ ID NO:2. More preferably, the polynucleotide comprises a nucleic acid sequence that encodes an Endo-SR polypeptide species that includes within its amino acid sequence an at least twenty amino acid contiguous sequence of SEQ ID NO:2. Still more preferably, the polynucleotide comprises a nucleic acid sequence that encodes an Endo-SR polypeptide species that includes within its amino acid sequence an at least 22 amino acid contiguous sequence of SEQ ID NO:2. In illustrative embodiments, such a polynucleotide comprises at least about 24, at least about 26, at least about 28, or at least about 30 or more contiguous amino acids from SEQ ID NO:2. In one embodiment, the preferred polynucleotides of the invention encode a polypeptide that comprises the sequence of SEQ ID NO:2.

The term "a sequence essentially as set forth in SEQ ID NO:2," means that the sequence substantially corresponds to a portion of the sequence of SEQ ID NO:2 and has relatively few amino acids that are not identical to, or a biologically functional equivalent of, the amino acids of any of these sequences. The term "biologically functional equivalent" is well understood in the art and is further defined in detail herein (e.g., see Illustrative Embodiments). Accordingly, sequences that have between about 70% and about 80%, or more preferably between about 81% and about 90%, or even more preferably between about 91% and about 99% amino acid sequence identity or functional equivalence to the amino acids of SEQ ID NO:2 will be sequences that are "essentially as set forth in SEQ ID NO:2." In illustrative embodiments, the endonuclease polypeptides of the present invention emcompass polypeptide species that are about 92% identical to the amino acid sequence of SEQ ID NO:2, or about 93% identical to the amino acid sequence of SEQ ID NO:2, or even about 94% identical to the amino acid sequence of SEQ ID NO:2, and in some instances will be about 95% or 96% identical to the amino acid sequence of SEQ ID NO:2, or even more. As such, it is contemplated that sequences that are about 97% or 98% or 99% identical to the amino acid sequence of SEQ ID NO:2 will be preferred for practice of the present invention. Indeed, when mutant endonuclease compositions are contemplated, or when endonuclease polypeptides are isolated from related species, or when allelic variants of the polypeptide species occur within one or more species of animal from which the polypeptide is isolated, it is contemplated that one or more amino acids may be altered, mutated, deleted, or even one or more amino acids added to the sequence of SEQ ID NO:2, and still have a polypeptide that has endonuclease activity.

Such mutated polypeptide species may have altered endonuclease activity or altered endonuclease specificity, as as such, may possess greater or reduced activity or specificity when compared to the wild-type polypeptide shown in SEQ ID NO:2.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other polynucleotide sequences, such as promoters, enhancers, expression elements, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant polynucleotide protocol. For example, nucleic acid fragments may be prepared that include a short contiguous stretch encoding the whole or a portion of the peptide sequence disclosed in SEQ ID NO:2, or that are identical to or complementary to DNA sequences which encode the peptide disclosed in SEQ ID NO:2, and particularly the DNA segment disclosed in SEQ ID NO:1. For example, DNA sequences such as about 24, about 25, about 26, or about 27 or more nucleotides in length, and even those that are up to and including about 10,000, about 5,000, about 4,000, about 3,000, about 2,000, about 1000, about 800, about 700, about 600, about 500, about 400, about 300, about 200, about 100, or even about 75, 50 or 25 base pairs in length (including all intermediate lengths) are also contemplated to be useful.

It will be understood that this invention is not limited to the particular nucleic acid sequences which encode peptides of the present invention, or which encode the amino acid sequence of SEQ ID NO:2, including the DNA sequence which is particularly disclosed in SEQ ID NO:1, and the genomic DNA sequences disclosed in SEQ ID NO:3 and SEQ ID NO:4. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

It will be readily understood that "intermediate lengths", in the contexts of both polynucleotides and polypeptides, means any integer length that lies within or is between the quoted ranges. For example, sequences from between about 24 and about 10,000 nucleotides in length, will include all integers between such lengths, including lengths of about 24, 25, 26, 27, 28, 29, 30, 31, 32, 33, 34, 35, 36, 37, 39, 39, 40, 41, 42, 43, 44, 45, 46, 47, 48 , 49, etc.; 50, 51, 52, etc.; 60, 61, 62, etc., 70, 75, 76, 77, 78, 79, 80, 81, 82, 83, 84, 85, 90, 95, 100, 105, 110, 115, etc.; 120, 130, 140, 150, 160, 170, 180, 190, etc.; 200, 201, 202, 203, 204, 205, 206, 207,208, 209, 210, 220, 230, 240, 250, 260, 270, 280, 290, 300, including all integers through the 301–500; 501–1,000; 1,001–2,000; 2,001–3,000; 3,001–4,000; 4,001–6,000, 6,001–9,000, and up to and including sequences of about 9,500, 9,600, 9,700, 9,800, 9,900, 10,000 nucleotides and the like. Similarly, sequences from between about 19 and about 200 amino acids in length, will include all integers between such lengths, including lengths of about 20, 21, 22, 23, 24, 25, 26, 27, 28, 29, 30, 31, 32, 33, 34, 35, 36, 37, 38, 39, 40, etc.; 40, 41, 42, 43, etc.; 50, 51, 52, etc.; 60, 61, 62, etc., 70, 75, 80, 85, 90, 95, 100, 105, 110, 115, etc.; 120, 130, 140, 150, 160, 170, 180, 190, etc.; including all integers up to and including the full-length polypeptide of 192 amino acids. Naturally, when all or a portion of the coding region for the Endo-SR polypeptide is fused to one or more additional polypeptides (such as in the preparation of fusion proteins, peptide adjuvants, and the like) polypeptides longer than the full-length sequence are also contemplated to be useful. Likewise, the Endo-SR polypeptide homologs isolated from other mammalian species may be slightly longer than the sequence of SEQ ID NO:2, and as such, polypeptides having a length of about 192, about 194, about 195, about 196, about 197, about 198, about 199, or even about 200 to about 300; or more amino acids and the like may also be useful in certain embodiments, and as such, are contemplated to fall within the scope of the present disclosure.

The polynucleotides and polypeptides of the present invention also encompass biologically-functional, equivalent polypeptides and polynucleotides. Such sequences, for example, may arise as a consequence of codon redundancy and functional equivalency that are known to occur naturally within nucleic acid sequences and the proteins thus encoded. Because, it has been demonstrated that the Endo-SR exhibits both specific endonuclease activity (at G-rich residues) and a degradative activity, it is likely that the "improved" or "second-generation" Endo-SR polypeptides may be desirable and synthesized to improve or modify its sequence specificity. Such altered proteins may result in novel endonuclease activities with specificity resembling that of prokaryotic restriction endonucleases with many potential application in the research and biotechnology fields. As such, functionally-equivalent Endo-SR proteins or peptides also represent important aspects of the invention, and may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length Endo-SR protein or smaller peptide fragment derived therefrom, is positioned under the control of one or more promoters or other expression elements. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

2.2 Polynucleotides as Hybridization Probes and Primers

In addition to their use in directing the expression of the novel Endo-SR polypeptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of SEQ ID NO:1 will find particular utility. Longer contiguous identical or complementary sequences, e.g., those of about 20, 30, 40, 50, 100, 200, 500, 1000, 2000, 5000, 10000, etc. (including all intermediate lengths and up to and including full-length sequences) will also be of use in certain embodiments.

The ability of such nucleic acid probes to specifically hybridize to an Endo-SR polypeptide-encoding sequence will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 14–25, 26–40, 41–60, or even of 100–200 nucleotides or so in length, either identical to, or complementary to, the sequence disclosed in SEQ ID NO:1, are particularly contemplated as hybridization probes for use in, e.g., Southern and Northern blotting. Smaller fragments will generally find use in hybridization embodiments, wherein the length of the contiguous complementary region may be varied, such as between about 10–14 and about 100 or 200 nucleotides, but larger contiguous complementarity stretches may be used, according to the length complementary sequences one wishes to detect.

The use of a hybridization probe of about 19 nucleotides in length allows the formation of a duplex molecule that is both stable and selective. Molecules having contiguous complementary sequences over stretches greater than 19 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,195 and U.S. Pat. No. 4,683,202 (each specifically incorporated herein by reference in its entirety), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions, typically referred to in the art as "high stringency conditions" tolerate little, if any, mismatch between the probe and the template or target strand, and would be particularly suitable for isolating Endo-SR-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1994; Segal 1976; Prokop, 1991; and Kuby, 1991, are particularly relevant.

Of course, for some applications, for example, where one desires to prepare mutants employing a mutant primer strand hybridized to an underlying template or where one seeks to isolate Endo-SR-encoding sequences from related species, functional equivalents, or the like, less stringent hybridization conditions will typically be needed in order to allow formation of the heteroduplex. In these circumstances, one may desire to employ conditions such as salt concentrations of from about 0.15 M to about 0.9 M, and temperature ranges of from about 20° C. to about 55° C. Using these conditions, typically referred to in the art as "low stringency conditions," cross-hybridizing species are readily identified as positively hybridizing signals with respect to control hybridizations.

In any case, however, it is generally appreciated that hybridization conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results. In any circumstances, it is desirable that the conditions used for hybridization to detect gene segments encoding Endo-SR polypeptides will be sufficiently stringent to permit hybridization of the probe to sequences which encode polypeptides having Endo-SR or Endo-SR-like activity, but will not permit hybridization of the probe to nucleotide sequences which do not encode polypeptides having Endo-SR or Endo-SR-like activity.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

2.3 Recombinant Vectors and Protein Expression

The invention also discloses and claims a composition comprising an Endo-SR polypeptide. The composition may comprises one or more host cells which express an Endo-SR polypeptide, recombinant host cells expresses the protein, cell suspensions, extracts, inclusion bodies, or tissue cultures or culture extracts which contain an Endo-SR polypeptide, culture supernatant, disrupted cells, cell extracts, lysates, homogenates, and the like. The Endo-SR polypeptides may be present in aqueous form, or alternatively, in dry, semi-wet, or similar forms such as cell paste, cell pellets, or alternatively freeze dried, powdered, lyophilized, evaporated, or otherwise similarly prepared in dry form. Such means for preparing Endo-SR polypeptides are well-known to those of skill in the art of protein isolation and purification. In certain embodiments, the Endo-SR polypeptides may be purified, concentrated, admixed with other reagents, or processed to a desired final form. Preferably, the composition will comprise from about 1% to about 90% by weight of the Endo-SR polypeptide, and more preferably from about 5% to about 50% by weight.

In a preferred embodiment, the Endo-SR polypeptide compositions of the invention may be prepared by a process which comprises the steps of culturing a host cell which expresses an Endo-SR polypeptide under conditions effective to produce such a protein, and then obtaining the protein from the cell. The obtaining of such an Endo-SR polypeptide may further include purifying, concentrating, processing, or admixing the protein with one or more reagents. Preferably, the Endo-SR polypeptide is obtained in an amount of from between about 1% to about 90% by weight, and more preferably from about 5% to about 70% by weight, and even more preferably from about 10% to about 20% to about 30%, or even to about 40% or 50% by weight.

The invention also relates to a method of preparing an Endo-SR polypeptide composition. Such a method generally involves the steps of culturing a host cell which expresses an Endo-SR polypeptide under conditions effective to produce the protein, and then obtaining the protein so produced. The vectors of the invention which comprise nucleic acid segments encoding Endo-SR polypeptides may be used to transform other suitable bacterial or eukaryotic cells to produce the polypeptides of the invention.

In such embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding an Endo-SR polypeptide in its natural environment. Such promoters may include promoters normally associated with other genes, and/or promoters isolated from any bacterial, viral, or eukaryotic cell. Preferred eukaryotic cells are animal cells, with mammalian cells, particularly human cells, being most preferred. Naturally, it will be important to employ a promoter that effectively directs the expression of the DNA segment in the cell type, tissue, organism, animal, or recombinant host cell chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the Pichia expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of Endo-SR polypeptides or epitopic core regions, such as may be used to generate anti-Endo-SR antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequences from SEQ ID NO:2.

2.4 Transgenes and Transgenic Host Cells Expressing Endo-SR

In yet another aspect, the present invention provides methods for producing a transgenic cell, and in particular a plant or animal cell which expresses a nucleic acid segment encoding the novel Endo-SR polypeptides of the present invention. The process of producing transgenic cells is well-known in the art. In general, the method comprises transforming a suitable host cell with a DNA segment which contains a promoter operably linked to a coding region that encodes an Endo-SR polypeptide. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular Endo-SR polypeptide expressed in a particular transgenic cell, the invention also provides for the expression of Endo-SR antisense mRNA. The use of antisense mRNA as a means of controlling or decreasing the amount of a given protein of interest in a cell is well-known in the art.

In a preferred embodiment, the invention encompasses an animal cell which has been transformed with a nucleic acid segment of the invention, and which expresses a gene or gene segment encoding one or more of the novel polypeptide compositions disclosed herein. As used herein, the term "transgenic host cell" is intended to refer to a host cell, either prokaryotic or eukaryotic, that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed host cell, such as genes which may normally be present in the non-transformed cell but which one desires to either genetically engineer or to have altered expression.

It is contemplated that in some instances the genome of a transgenic host cell of the present invention will have been augmented through the stable introduction of a transgene encoding an Endo-SR polypeptide, either native or synthetically modified or mutated. In some instances, more than one transgene will be incorporated into the genome of the transformed host cell. Such is the case when more than one Endo-SR polypeptide-encoding DNA segment is incorporated into the genome of such a cell. In certain situations, it may be desirable to have one, two, three, four, or even more Endo-SR polypeptides (either native or recombinantly-engineered) incorporated and stably expressed in the transformed transgenic host cell. In preferred embodiments, the introduction of the transgene into the genome of the host cell results in a stable integration wherein the progeny of such cells also contain a copy of the transgene in their genome.

2.5 Transgenic Animals Lacking Endo-SR Activity

Alternatively, the invention provides a "knockout" transgenic animal which has been transformed with a nucleic acid segment of the invention, in such a way that Endo-SR activity is reduced or eliminated from cells of the transgenic knockout animal. In some instances the genome of a transgenic host cell of the present invention will have been augmented through the stable replacement of a native Endo-SR encoding gene with a defective Endo-SR gene, or alternatively, the native Endo-SR-encoding gene will be disrupted, deleted, or replaced by a nucleic acid segment which prevents synthesis of a functional Endo-SR polypeptide in the resulting transgenic animal.

Means for transforming a host cell and the preparation of a transgenic cell line are well-known in the art (as exemplified in U.S. Pat. Nos. 5,550,318; 5,508,468; 5,482,852; 5,384,253; 5,276,269; and 5,225,341, all specifically incorporated herein by reference), and are briefly discussed herein. Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed Endo-SR polypeptides. These DNA constructs can further include structures such as promoters, enhancers, polylinkers, or even gene sequences which have positively- or negatively-regulating activity upon the particular genes of interest as desired. The DNA segment or gene may encode either a native or modified Endo-SR polypeptide, which will be expressed in the resultant recombinant cells, and/or which will impart a desired phenotype to the transformed host cell.

2.6 Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as $E.\ coli$ polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as $E.\ coli$ cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

2.7 Compositions and Methods for Producing Antibodies

In particular embodiments, the inventors contemplate the use of antibodies, either monoclonal or polyclonal which bind to the Endo-SR polypeptides disclosed herein. Means for preparing and characterizing antibodies are well known in the art (See, e.g, Harlow and Lane, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified Endo-SR polypeptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, (Gefter et al., 1977). The use of electrically induced fusion methods is also appropriate (Goding, 1986, pp. 71–74).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

2.8 Endo-SR Screening and Immunodetection Kits

The present invention also provides compositions, methods and kits for screening samples suspected of containing an Endo-SR polypeptide or a gene encoding such an Endo-SR polypeptide. Alternatively, the invention provides compositions, methods and kits for screening samples suspected of containing Endo-SR polypeptides or genes encoding Endo-SR polypeptides which are functionally equivalent to, or substantially homologous to, the Endo-SR polypeptide disclosed herein. Such screening may be performed on samples such as transformed host cells, clinical or laboratory samples suspected of containing or producing such a polypeptide or nucleic acid segment. A kit can contain a novel nucleic acid segment or an antibody of the present invention. The kit can contain reagents for detecting an interaction between a sample and a nucleic acid or an antibody of the present invention. The provided reagent can be radio-, fluorescently- or enzymatically-labeled. The kit can contain a known radiolabeled agent capable of binding or interacting with a nucleic acid or antibody of the present invention.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, a test plate having a plurality of wells, or a microscope slide. When the reagent provided is a dry powder, the powder can be reconstituted by the addition of a suitable solvent, that may be provided.

In still further embodiments, the present invention concerns immunodetection methods and associated kits. It is proposed that the Endo-SR polypeptides of the present invention may be employed to detect antibodies having reactivity therewith, or, alternatively, antibodies prepared in accordance with the present invention, may be employed to detect Endo-SR polypeptides or Endo-SR polypeptide-related epitope-containing containing amino acid sequences. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either an Endo-SR polypeptide or an Endo-SR polypeptide-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of Endo-SR polypeptides or related peptides and/or antibodies in a sample. Samples may include cells, cell supernatants, cell suspensions, cell extracts, enzyme fractions, protein extracts, or other cell-free compositions suspected of containing Endo-SR polypeptides. Generally speaking, kits in accordance with the present invention will include a suitable Endo-SR polypeptide, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

2.9 ELISAs and Immunoprecipitation

ELISAs may be used in conjunction with the invention. In an ELISA assay, proteins or peptides incorporating Endo-SR polypeptide antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hours, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g, incubation for 2 hours at room temperature in a PBS-containing solution such as PBS Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectra spectrophotometer.

The anti-Endo-SR antibodies of the present invention are particularly useful for the isolation of other Endo-SR polypeptide antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

2.10 Western Blots

The Endo-SR compositions of the present invention will find great use in immunoblot or western blot analysis. The anti-Endo-SR antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

2.11 Epitopic Core Sequences

The present invention is also directed to Endo-SR polypeptide compositions, free from total cells and other peptides, which comprise a purified Endo-SR polypeptide which incorporates an epitope that is immunologically cross-reactive with one or more anti-Endo-SR antibodies. In particular, the invention concerns epitopic core sequences derived from Endo-SR polypeptides and Endo-SR polypeptide-derived proteins or peptides.

As used herein, the term "incorporating an epitope(s) that is immunologically cross-reactive with one or more anti-Endo-SR antibodies" is intended to refer to a peptide or protein antigen which includes a primary, secondary or tertiary structure similar to an epitope located within an Endo-SR polypeptide. The level of similarity will generally be to such a degree that monoclonal or polyclonal antibodies directed against the Endo-SR polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of Endo-SR immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, e.g., Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to Endo-SR polypeptides. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the Endo-SR polypeptide-directed antibodies disclosed herein. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at about 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

2.12 Biological Functional Equivalents

Modification and changes may be made in the structure of the Endo-SR polypeptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the codons given in Table 1.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |

TABLE 1-continued

| Amino Acids | | | Codons | | | | | |
|---|---|---|---|---|---|---|---|---|
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, ie., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within +1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

2.13 Regulating the Expression of Endo-SR Activity in a Cell Using Anti-Sense Constructs The end result of the flow of genetic information is the synthesis of protein. DNA is transcribed by polymerases into messenger RNA and translated on the ribosome to yield a folded, functional protein. Thus, even from this simplistic description of an extremely complex set of reactions, it is obvious that there are several steps along the route where protein synthesis can be inhibited. The native DNA segment coding for Endo-SR, as all such mammalian DNA strands, has two strands: a sense strand and an antisense strand held together by hydrogen bonding. The messenger RNA coding for Endo-SR has the same nucleotide sequence as the sense DNA strand except that the DNA thymidine is replaced by uridine. Thus, synthetic antisense nucleotide sequences will bind to the mRNA coding for Endo-SR and inhibit expression of the protein.

Antisense oligodeoxynucleotides (AS-ODNs) are single-stranded, short sequences of DNA (Cohen, 1989; De Mesmaeker et al., 1995) that are complementary to specific messenger RNA (mRNA). Since AS-ODNs hybridize with the mRNA, they prevent the targeted mRNA from expressing its polypeptide product in the cell.

The targeting of antisense oligonucleotides to bind mRNA is one mechanism to shut down protein synthesis. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829, each specifically incorporated herein by reference in its entirety). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., 1988; Vasanthakumar and Ahmed, 1989; Peris et al., 1998; U.S. Pat. No. 5,801,154; U.S. Pat. No. 5,789,573; U.S. Pat. No. 5,718,709 and U.S. Pat. No. 5,610,288, each specifically incorporated herein by reference in its entirety). Antisense constructs have also been described that inhibit and can be used to treat a variety of abnormal cellular proliferations, e.g cancer (U.S. Pat. No. 5,747,470; U.S. Pat. No. 5,591,317 and U.S. Pat. No. 5,783,683, each specifically incorporated herein by reference in its entirety).

AS-ODNs have also been used for the treatment of a variety of diseases and disorders in animals, including hypertension (Phillips, 1997; Wielbo et al., 1994; Phillips et al., 1994 and Gyurko et al., 1997; Gyurko et al., 1993; Meng et al., 1994; Wielbo et al., 1997; Wielbo et al., 1996; Wielbo et al., 1995).

The inventors contemplate that antisense oligonucleotide and peptide nucleic acid compositions that specifically bind Endo-SR mRNA in a mammalian cell, may be used to alter the expression of Endo-SR in the cell.

Therefore, the present invention provides a composition comprising at least a first oligonucleotide of at least 9 to about 35 bases in length, wherein the oligonucleotide specifically binds to a portion of mRNA expressed from a gene encoding a mammalian Endo-SR polypeptide, and further wherein binding of the oligonucleotide to the mRNA is effective in decreasing the activity of the enzyme in a host cell expressing the mRNA.

In certain aspects of the invention, the oligonucleotide comprises deoxyribonucleic acid, ribonucleic acid, or peptide-nucleic acid. In particular embodiments, the oligonucleotide comprises a sequence that is complementary to at least ten, at least eleven, at least twelve, at least thirteen or at least fourteen or more contiguous bases from SEQ ID NO:1. In other aspects of the present invention, the oligonucleotide has no more than 4, no more than 3, no more than 2, no more than 1 or no mismatches from the mRNA sequence to which it specifically binds. In particular aspects of the invention, the composition further comprises at least a second oligonucleotide of at least 9 to about 35 nucleotides in length, wherein the second oligonucleotide specifically binds to a portion of mRNA expressed from a gene encoding another mammalian endonuclease. Alternatively, the composition may further comprises one or more anti-cancer or anti-tumor agents, or may comprise one or more additional endonuclease compositions. In certain preferred embodiments, the composition further comprises a pharmaceutically-acceptable vehicle, exemplified by, but not limited to, a liposome, a lipid particle, a lipid vesicle, a nanoparticle, a microparticle, a nanocapsule, a nanosphere, or a sphingosome.

In certain aspects of the invention, the enzyme is a human enzyme. In particular embodiments, the host cell is a mammalian host cell. In certain preferred embodiments of the invention, the host cell is a human cell. In other preferred aspects, the host cell is comprised within a human.

The present invention also provides a polynucleotide of at least 9 to about 35 bases in length, wherein the polynucleotide specifically binds to a portion of mRNA expressed from a DNA segment encoding a mammalian Endo-SR polypeptide, and further wherein binding of the polynucleotide to the mRNA is effective in decreasing the transcription of the mRNA in a host cell expressing the mRNA. The present invention further provides an antisense nucleic acid molecule comprising a segment complementary to a sequence unique to mammalian Endo-SR-specific mRNA, wherein when administered to a living organism, the antisense molecule is capable of reducing the amount of the enzyme in the organism.

2.14 Definitions

The oligonucleotides (or "ODNs" or "polynucleotides" or "oligos" or "oligomers" or "n-mers") of the present invention are preferably deoxyoligonucleotides (i.e. DNAs), or derivatives thereof; ribo-oligonucleotides (i.e. RNAs) or derivatives thereof; or peptide nucleic acids (PNAs) or derivatives thereof.

The term "substantially complementary," when used to define either amino acid or nucleic acid sequences, means that a particular subject sequence, for example, an oligonucleotide sequence, is substantially complementary to the sequence of Endo-SR-specific sequences (e.g., those identified in SEQ ID NO:1 or SEQ ID NO:2), and thus will specifically bind to a portion of an mRNA encoding an Endo-SR polypeptide. As such, typically the sequences will be highly complementary to the mRNA "target" sequence, and will have no more than 1, 2, 3, 4, 5, 6, 7, 8, 9, or 10 base mismatches throughout the sequence. In many instances, it may be desirable for the sequences to be exact matches, i.e. be completely complementary to the sequence to which the oligonucleotide specifically binds, and therefore have zero mismatches along the complementary stretch. As such, highly complementary sequences will typically bind quite specifically to the target sequence region of the mRNA and will therefore be highly efficient in reducing, and/or even inhibiting the translation of the target mRNA sequence into polypeptide product.

Substantially complementary oligonucleotide sequences will be greater than about 80 percent complementary (or '% exact-match') to the corresponding mRNA target sequence to which the oligonucleotide specifically binds, and will, more preferably be greater than about 85 percent complementary to the corresponding mRNA target sequence to which the oligonucleotide specifically binds. In certain aspects, as described above, it will be desirable to have even more substantially complementary oligonucleotide sequences for use in the practice of the invention, and in such instances, the oligonucleotide sequences will be greater than about 90 percent complementary to the corresponding mRNA target sequence to which the oligonucleotide specifically binds, and may in certain embodiments be greater than about 95 percent complementary to the corresponding mRNA target sequence to which the oligonucleotide specifically binds, and even up to and including 96%, 97%, 98%, 99%, and even 100% exact match complementary to the target mRNA to which the designed oligonucleotide specifically binds.

Percent similarity or percent complementary of any of the disclosed sequences may be determined, for example, by comparing sequence information using the GAP computer program, version 6.0, available from the University of Wisconsin Genetics Computer Group (UWGCG). The GAP program utilizes the alignment method of Needleman and Wunsch (1970). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (1986), (2) a penalty of 3.0 for each gap and an additional 0.10 penalty for each symbol in each gap; and (3) no penalty for end gaps.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein produced in a microbial expression system which is essentially free of native endogenous substances. Protein expressed in most bacterial cultures, e.g., *E. coli*, will be free of glycan. Protein expressed in yeast may have a glycosylation pattern different from that expressed in mammalian cells.

"Biologically active," as used throughout the specification means that a particular molecule shares sufficient amino acid sequence similarity with the embodiments of the present invention disclosed herein to be capable of specifically cross-react or bind specifically to one or more antibodies raised against a mammalian Endo-SR polypeptide or peptide fragment thereof.

"DNA sequence" refers to a DNA polymer, in the form of a separate fragment or as a component of a larger DNA construct. Preferably, the DNA sequences are in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where the same do not interfere with manipulation or expression of the coding regions.

"RNA sequence" refers to an RNA polymer, in the form of a separate fragment or as a component of a larger RNA construct, such as a messenger RNA (mRNA) encoding one or more Endo-SR polypeptides. Preferably, the RNA sequences are in a quantity or concentration enabling identification, manipulation, and recovery of the sequence and its component nucleotide sequences by standard biochemical methods, for example, using a cloning vector, or alternatively, by chemically synthesizing the RNA molecule completely or partially in vitro.

"Nucleotide sequence" refers to a heteropolymer of deoxyribonucleotides, ribonucleotides, or peptide-nucleic acid sequences that may be assembled from smaller fragments, isolated from larger fragments, or chemically synthesized de novo or partially synthesized by combining shorter oligonucleotide linkers, or from a series of oligonucleotides, to provide a sequence which is capable of specifically binding to an mRNA molecule and acting as an antisense construct to alter, reduce, or inhibit the transcription of the message into polypeptide, and thus, ultimately affect the concentration, amount, or activity of the final gene product in situ, in vitro, or in vivo.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Size-exclusion chromatography and SDS-PAGE analysis of Endo-SR purification fractions. Size-exclusion chromatography of partially purified bovine Endo-SR. A highly purified bovine Endo-SR sample (Fraction IV) was loaded onto a Superose 12 (Pharmacia) size-exclusion column and fractionated according to apparent native molecular weight. Enzyme activity (dashed lines) eluted from this column at an $M_r$ of ~35 000 in direct correspondence with a well-defined protein peak.

Figure 2A:
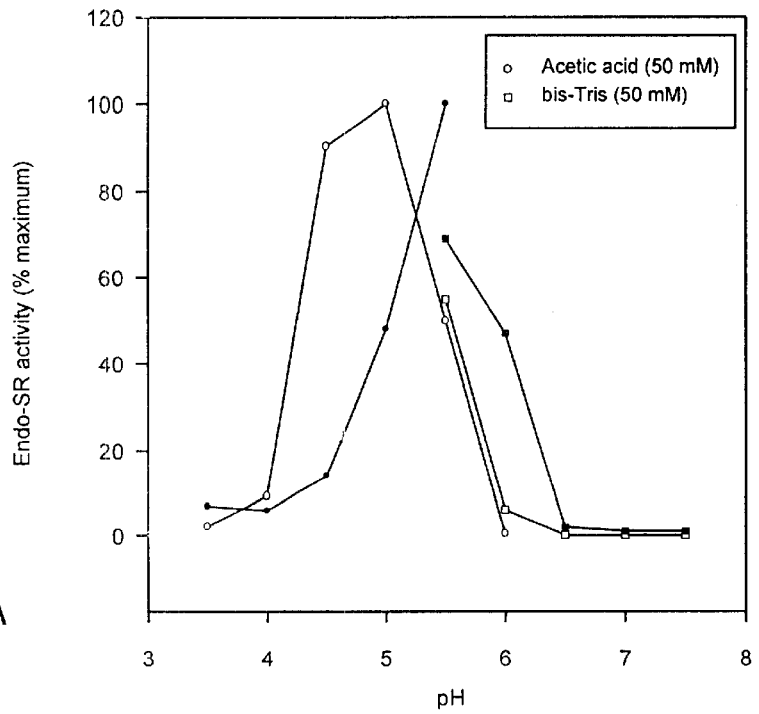

FIG. 2A. Characterization of murine and bovine Endo-SR activity parameters. Effect of pH on Endo-SR activity. Nuclease assays were performed with either 50 mM acetic acid (pH 3.5–6.0) or bis-Tris (pH 5.5–7.5), and endonuclease specific activity was determined essentially as previously described. Reported activity values are expressed as percentages of maximal detected enzyme activity. Bovine and murine enzyme activities are represented by open and closed symbols, respectively.

Figure 2B:
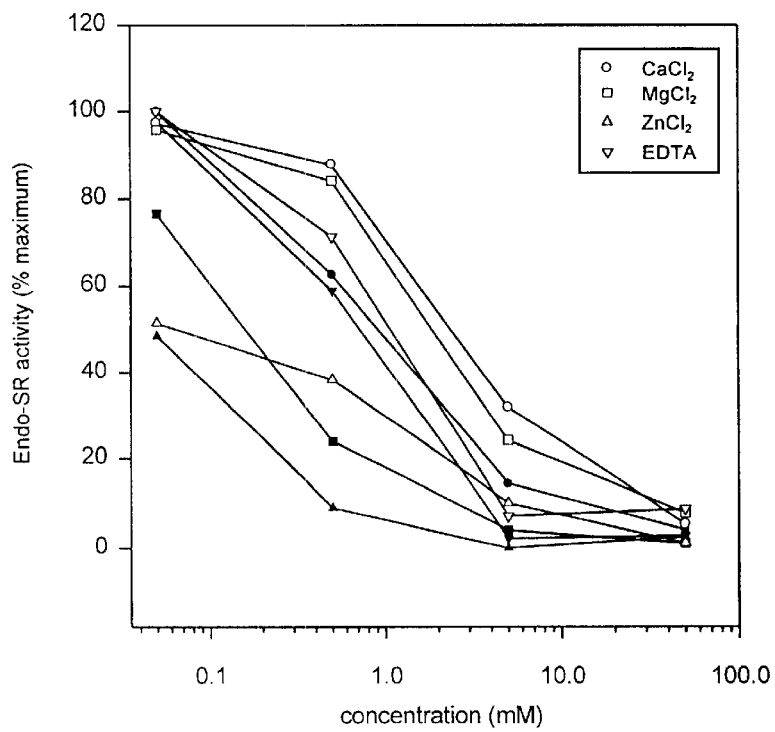

FIG. 2B. Effect of various common divalent metal cation ($M^{2+}$) species on Endo-SR activity. Nuclease reaction buffer used in these assays contained no $Mg^{2+}$, and nuclease reactions were adjusted to various M or EDTA concentrations. Nuclease assays performed with supplemental $M^{2+}$ or EDTA were pre-incubated for 30 min on ice prior to addition of the DNA substrate. Specific endonuclease activity values detected in these assays were normalized against nuclease reactions, which contained no supplemental $M^{2+}$ or EDTA, and expressed as percentages of this reaction activity. Bovine and murine enzyme activities are represented by open and closed symbols, respectively.

Figure 3A:
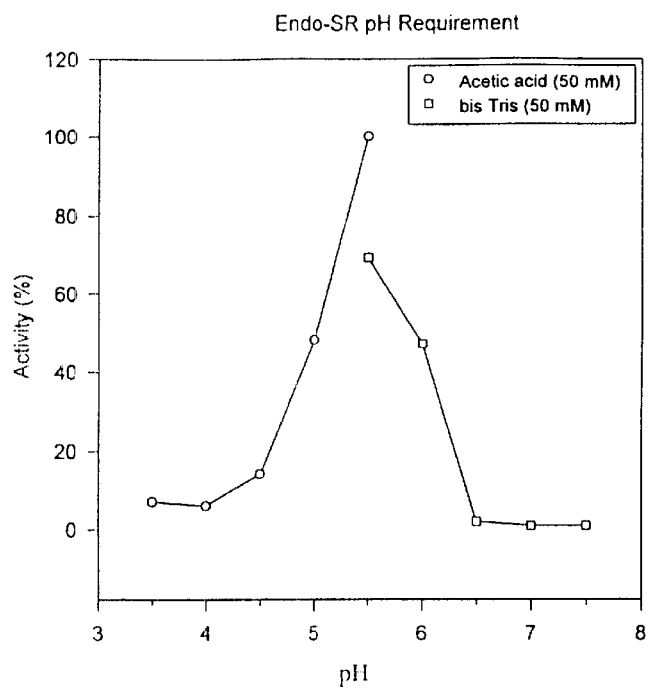

FIG. 3A. Characterization of Endo-SR activity parameters. Effect of pH on Endo-SR activity. Nuclease assays were performed as previously described except for the noted changes in buffered pH conditions. Activities shown are expressed as percentages of the maximal detected enzyme activity.

Figure 3B:
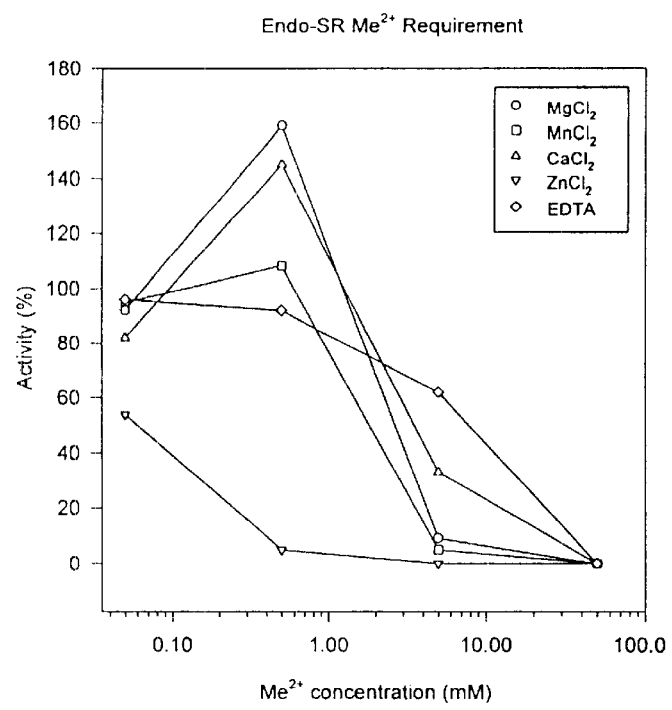

FIG. 3B. Effect of $M^{2+}$ species on Endo-SR activity. Nuclease assays were performed as previously described but with varied concentrations of different $M^{2+}$ species (or EDTA) replacing the standard (5 mM $Mg^{2+}$) assay condition. Activity values shown are expressed as percentages of an activity detected in a control assay (0 $\mu$M) containing no added $M^{2+}$ species.

Figure 4A:
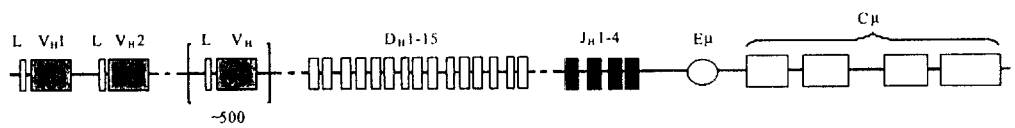
Figure 4A:
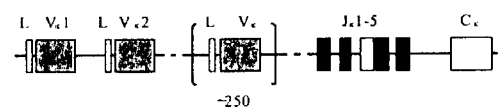

FIG. 4A. Schematic diagram of the V-(D)-J recombination process. Schematic diagram of the immunoglobulin heavy-chain (IgH) and kappa light-chain (Igκ) genes.

Figure 4B:
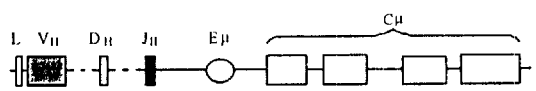
Figure 4B:
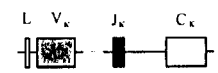
Figure 4B:
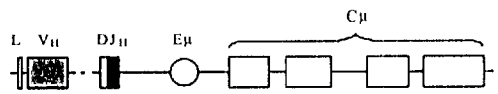
Figure 4B:
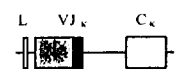
Figure 4B:
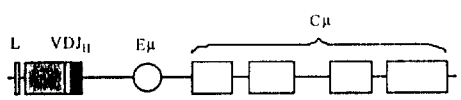
Figure 4B:
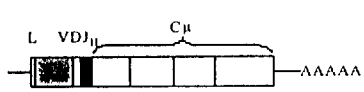
Figure 4B:
Figure 4B:
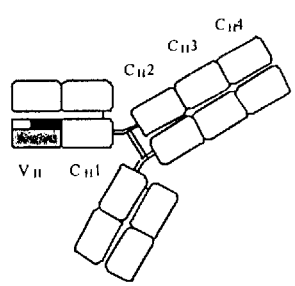
Figure 4B:
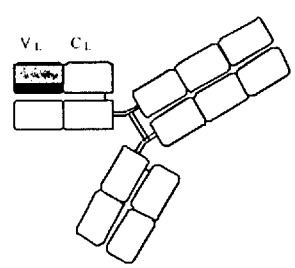

FIG. 4B. Rearrangement of the IgH and Igκ gene loci during B cell development. V-(D)-J rearrangements in pro-B cells recombine IgH $D_H$ and $J_H$ gene segments to create a $DJ_H$ chimera that is subsequently joined to one of ~500 $V_H$ region gene segments. Synthesis of a $VDJ_H$ region brings the rearranged $V_H$ region's promoter into close proximity with the IgH intronic enhancer (E$\mu$) and drives high-level transcription of the rearranged IgH gene. The translated IgH gene product associates with two surrogate light-chain proteins (VpreB and λ5) to form an IgM-like surface complex that induces Ig light-chain rearrangement and represses further heavy-chain rearrangement. V-(D)-J rearrangements within the Igκ locus join one of four functional Jκ elements (white box indicates a Jκ pseudogene) to one of ~250 Vκ gene elements. Functional expression of a Ig light-chain displaces the VpreB:λ5 surrogate light-chain during Ig assembly, resulting in the surface expression of an IgM protein complex that represses further rearrangement of the Ig light-chain genes. The antigen specificity of each IgM molecule is determined by the association of the theoretically unique $VDJ_H$ and $VJ_L$ regions of each Ig heavy- and light-chain.

Figure 5:
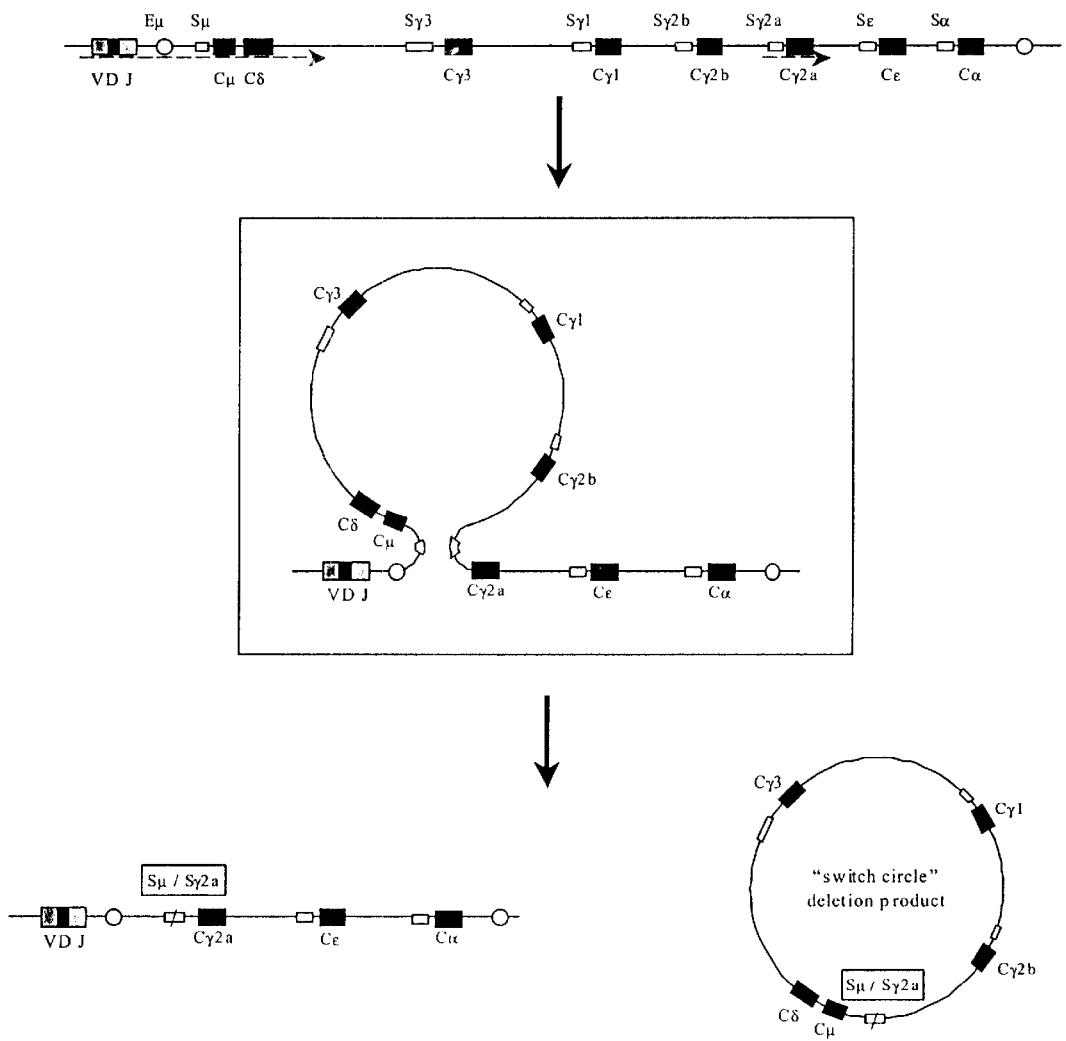

FIG. 5. Schematic diagram of the switch recombination process. The murine immunoglobulin heavy-chain gene locus contains eight constant region gene segments (black boxes), any of which can be expressed during B cell differentiation. All mature B lymphocytes initially express IgM ($C_\mu$), and can subsequently express IgD ($C_\delta$) through alternate splicing of the IgH primary transcript (long arrow). Mature B cells can also differentiate to selectively express any of the remaining six $C_H$ gene segments through site-specific rearrangement of the IgH gene locus in response to specific extracellular signals. Switch recombination alters $C_H$ gene expression by deletional replacement of the "active" $C_H$ gene segment, located directly downstream of the VDJ gene segment, with another selected $C_H$ gene segment. Switch rearrangements occur between large, highly repetitive "switch regions" (open boxes) found next to all recombinationally active constant region genes. Switch recombination requires transcriptional activation (arrows) and synapsis of the targeted switch regions, and produces reciprocal rearrangement products: the rearranged IgH gene locus and an extrachromosomal "switch circle" containing the deleted region (50~200 kb) of the IgH chromosome.

Figure 6:
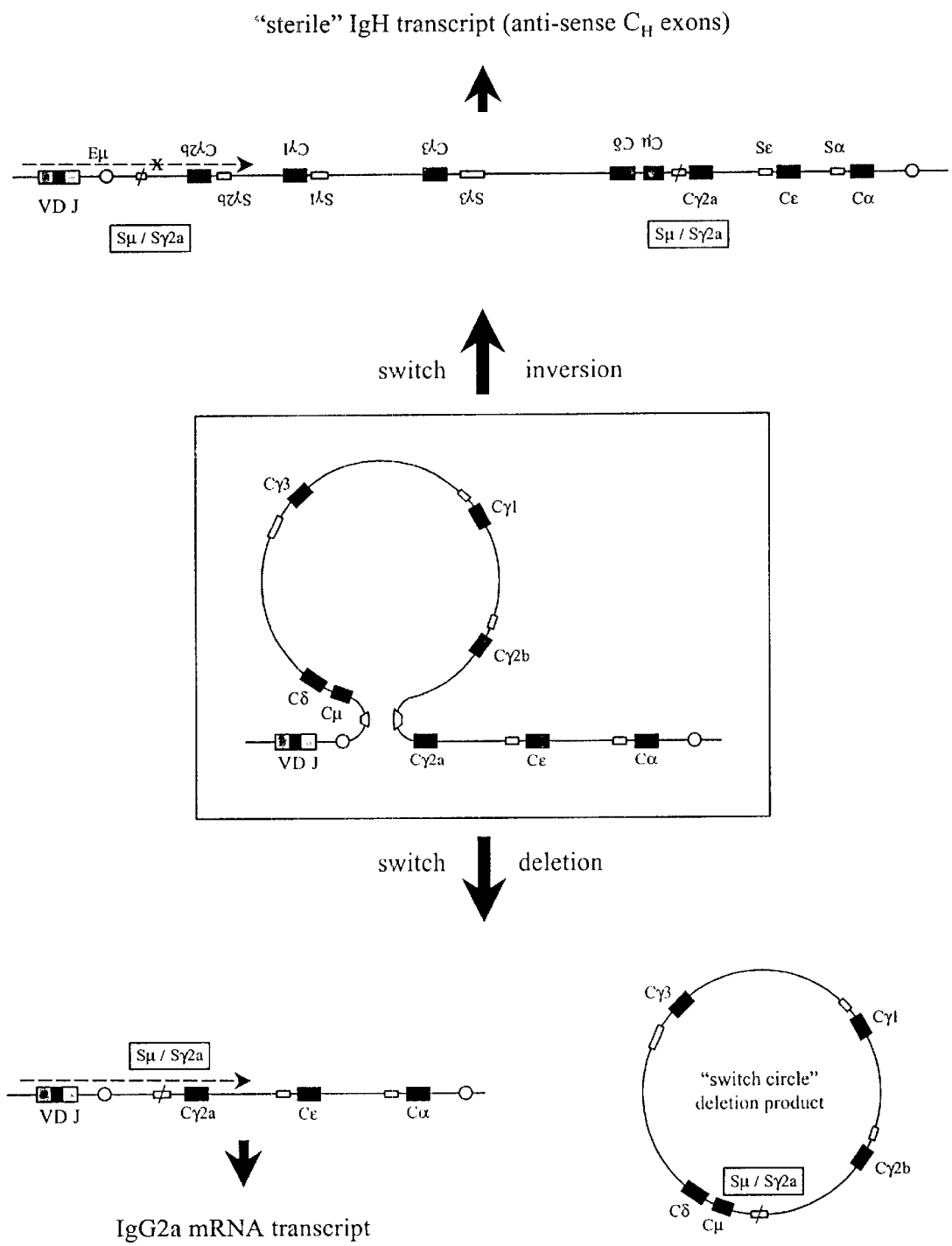

FIG. 6. Switch recombination products. Switch rearrangement events produce both switch deletion and switch inversion products with equal frequency. Switch deletions are required for expression of alternate $C_H$ region genes, while switch inversions appear to inactivate an IgH locus. Switch inversions reverse the orientation of the chromosomal region flanked by the two switch recombination breakpoints, generating a "sterile" IgH transcript (marked arrow) that does not encode a functional $C_H$ region. Switch inversions also ablate the transcriptional activation of the original targeted $C_H$ region, since these events transfer the affected $C_H$ promoter region to the newly formed chimeric 5' switch region (S$\mu$/Sγ2a, slashed box) precluding future transcription through the chimeric switch region adjacent to the originally targeted $C_H$ region.

FIG. 7. Endo-SR protein sequence homologies. Sequence analysis of purified Endo-SR protein has generated five peptide sequences, four of which demonstrate considerable homology and appear to represent independent isolates of two peptide sequences. Regions of sequence homology between these two peptides (peptides 1 and 2) are underlined.

4.0 DESCRIPTION OF ILLUSTRATIVE EMBODIMENTS

The inventors and others (Aguilera et al., 1985; Lyon et al., 1996; Wuerffel et al., 1990) have proposed that switch recombination should require at least three distinct activities: (i) sequence-specific binding of switch repeat/recombination sequence motifs (referred to as SRSs in this proposal), (ii) endonucleolytic cleavage of targeted SRSs, and (iii) ligation of SRS free DNA ends. During a search for factors that specifically interact with the SRS, the inventors identified a novel DNA endonuclease activity, designated Endo-SR, that specifically recognizes the most prevalent SRS motifs (Lyon et al., 1996). The inventors have isolated Endo-SR activity from both murine and bovine lymphoid tissues and found that in both species, Endo-SR activity is enriched in, but not restricted to, lymphoid tissue; demonstrates maximal activity between pH 5 and 6; is strongly inhibited by low concentrations of zinc; and does not require the addition of cation cofactors for full enzyme activity (Lyon and Aguilera, 1997; Lyon et al., 1996).

The inventors have purified the bovine Endo-SR nuclease activity to homogeneity and have identified a ~35 kDa protein species that directly correlates with enzyme activity (Lyon and Aguilera, 1997; Lyon et al., 1998). Protein microsequencing of this enzyme fraction produced five extended (>5 aa) peptide sequences, representing three independent Endo-SR peptides (Lyon et al., 1998). Sequence homology searches performed with these peptides, revealed significant similarity to the predicted amino acid sequence of a hypothetical 40 kDa human protein, R31240-2. A search of the NCBI database of expressed sequence tags revealed that R31240-2 (Endo-SR) mRNA is expressed in a variety of different human cell types, including cells derived from lymph node, ovarian, prostate, neuronal, epithelial, and endothelial tissues (Lyon et al., 1998). These findings are consistent with results that show that Endo-SR is expressed at variable levels in all human, murine and bovine cell lines and tissues analyzed to date (Lyon and Aguilera, 1997; Lyon et al., 1998; Lyon et al., 1996).

In order to determine if the R31240-2 gene encoded the Endo-SR activity, the inventors generated expression vectors containing human R31240-2 cDNA and assayed these constructs for the ability to promote Endo-SR activity. Overexpression of R31240-2 in mammalian cells lead to a significant increase in Endo-SR activity (Lyon et al., 1998) indicating that this gene represents the human homologue of Endo-SR. Three groups studying DNase II, an acidic endonuclease recently found to share several biochemical properties with Endo-SR (Baker et al., 1998; Wang et al., 1998; Yasuda et al., 1998), have also recently cloned the R31240-2 gene. The cloning of this gene by other groups searching for a acidic-nuclease activity, confirms the identification of R31240-2 as the human homologue of Endo-SR.

Efficient nuclear DNA degradation during apoptosis in a variety of cell types has recently been shown to require intracellular acidification (Gottlieb and Dosanjh, 1996; Gottlieb et al., 1996a; Meisenholder et al., 1996; Moore et al., 1993; Park et al., 1996; Sharma et al., 1996; Sharma and Srikant, 1998), and DNase II has now been proposed to be the major nuclease activated by this acidification event upon induction of apoptosis (Barry and Eastman, 1992; Eastman, 1995; Gottlieb et al, 1996b; Meisenholder et al., 1996; Walker and Sikorska, 1997). However, there is some controversy regarding the necessity of acidification in apoptosis (Walker and Sikorska, 1997), since at least four additional nucleases have also been implicated in apoptosis: a $Ca^{2+}/Mg^{2+}$ dependent endonuclease (see Walker and Sikorska, 1997 and refs. within), DNase I, Nuc-18, and a recently reported Caspase-activated Deoxyribonuclease (CAD; Enari et al., 1998). Due to the diversity of nuclease activities observed during apoptosis in different cell types, it has been proposed that more than one nuclease activity may be involved in nuclear DNA degradation during apoptosis (Walker and Sikorska, 1997).

Regulation of programmed cell death in C. elegans and mammals is highly similar and requires the activity of several highly homologous proteins (Driscoll, 1997; Hengartner, 1997). Nuclear DNA degradation during apoptosis in C. elegans appears to require an acid nuclease activity, since animals deficient in this activity (nuc-1 mutants) are viable but contain persistent apoptotic cells with undegraded nuclear DNA and are also deficient in metabolizing bacterial DNA (Hevelone and Hartman, 1988; Sulston, 1976). Nuclease assays performed with wild-type C. elegans protein extracts detected a potent endonuclease activity that readily degrades super-coiled plasmid DNA under mildly acidic conditions. The nuclease activity detected in these extracts was found to cleave a switch region DNA substrate in a pattern very similar to those produced by several mammalian Endo-SR activities. Specifically, the C. elegans acidic nuclease activity produces DNA breaks at each G-rich switch motif, roughly similar to species-specific breaks produced by several mammalian Endo-SR activities (Lyon and Aguilera, 1997; Lyon et al., 1998; Lyon et al., 1996), and strongly cleaves DNA at a TAGAG motif recognized by all mammalian enzymes. Nuclease assays performed with protein extracts derived from nuc-1 mutant worms detected extremely low levels of this acidic nuclease activity (<0.5% of wild-type), consistent with the leaky phenotype of the nuc-1 mutant allele examined (Hevelone and Hartman; 1988). Residual nuclease activity detected in these extracts demonstrated a specificity indistinguishable from that found in wild-type extracts, indicating that this activity was the only detectable acidic nuclease activity present in these animals.

EL-4 cells, which express very low levels of endogenous murine Endo-SR activity (Lyon et al., 1998), were co-transfected via electroporation with a constitutively active tetracycline receptor/VP16 (rTA) expression vector and a human Endo-SR expression vector under the control of the potent tetracycline-regulated rTA transactivator protein (Gossen et al., 1995). Recombinant protein expression was induced 48 h after transfection by shifting cells to a tetracycline-deficient culture medium. Specific Endo-SR nuclease activity present in these cells was determined by measurement of the amount of intact probe remaining after the nuclease assays (Lyon et al., 1996), and compared to values obtained in parallel assays with extracts from uninduced cells to determine induction ratios. Sequence specificity analysis of C. elegans and mammalian acid nuclease activities were performed and cell extracts were derived from human, mouse, cow and C. elegans (prepared as previously described (Lyon and Aguilera, 1997)) and analyzed for cleavage site specificity in standard nuclease assays using a consensus murine immunoglobulin switch region DNA substrate (Lyon et al., 1996). Sequence at DNA breaks generated by the C. elegans acidic nuclease activity were determined using known mammalian cleavage sites within this substrate (Lyon and Aguilera, 1997; Lyon et al., 1996). A comparison of the acid nuclease activity of C. elegans N2 wt (wild-type) and nuc-1 mutant animals was also performed. Nuclease assays were performed at pH 5.0 using ~300 ng of intact plasmid DNA and 0.01–1 mg of cell extract derived from N2wt or nuc-1 mutant C. elegans, allowed to proceed from 5 to 30 min, and then size-fractionated on a standard agarose gel. Reactions using 1 mg of nuc-1 mutant extracts demonstrate significantly less DNA degradation than comparable reactions using 0.01 mg of N2wt extract. Extracts from nuc-1 animals retain some residual acidic nuclease activity as seen by the conversion of supercoiled and nicked-circular plasmid DNA to linear DNA species. The inventors also determined the sequence specificity of acid nuclease activity in N2wt and nuc-1 mutant animals. Whole animal extracts derived from N2wt and nuc-1 mutant animals (0.1–10 mg) were generated as previously described (Lyon and Aguilera, 1997) and assayed for cleavage specificity in standard acidic nuclease assays using a consensus murine immunoglobulin switch region DNA substrate. N2wt and nuc-1 extracts demonstrated the same cleavage patterns, although nuc-1 extracts demonstrate <1% the activity found in N2wt extracts. N2wt extracts obliterate the reaction substrate when >0.1 mg is used in these assays.

Mammalian Endo-SR/DNase II proteins demonstrate a significant level of sequence similarity to the predicted C. elegans protein C07B5.5 [109/348 (31%) Identical, 158/348 (45%) Similar], and the C07B5.5 gene maps close to the putative nuc-1 locus on C. elegans chromosome X. The inventors have therefore amplified and sequenced C07B5.5 mRNA and germline DNA from wild-type and nuc-1 [nuc-1(e1392)X] mutant animals. C07B5.5 cDNA and DNA sequence derived from these animals has revealed that nuc-1(e1392)X mutant animals contain a nonsense mutation (TGG→TAG) within the first 60 aa of the C07B5.5 coding sequence, consistent with the expected defect in the nuc-1 (e1392)X mutant allele, which is suppressed by the sup-5 (e1464)III tRNA suppressor (UAG-Trp).

4.1 Molecular Studies on Antigen Receptor Gene Recombination

B lymphocytes generate a diverse repertoire of immunoglobulin (Ig) molecules during B cell development by specific rearrangement of Ig variable region gene segments that are widely separated along a germline chromosome (Tonegawa, 1983). Rearrangement of these gene segments by a lymphocyte-specific DNA rearrangement process called V-(D)-J recombination, generates the variable regions of both the Ig heavy- and light-chain genes (Alt et al., 1992; Tonegawa, 1983), which encode the antigen-binding region of the assembled Ig molecule. Receptor specificity is determined by the combinatorial association of individual Ig heavy- and light-chains (IgH and IgL, respectively), but the IgH constant region (CH) exons determine the receptor isotype, which specifies the tissue distribution and function of the secreted Ig receptor (Esser and Radbruch, 1990; Mond et al., 1995).

Murine B lymphocytes expressing IgM can be selectively induced to express IgG3, IgG1, IgG2b, IgG2a, IgE or IgA in response to stimuli resulting from different types of immune responses (Esser and Radbruch, 1990). Mature B lymphocytes are able to selectively "switch" their Ig isotype during an immune response by a site-specific DNA rearrangement process that deletes one set of $C_H$ exons and replaces them with one of six alternate sets of $C_H$ exons (Esser and Radbruch, 1990; Purkerson and Isakson, 1992; Snapper and Mond, 1993). Switch recombination thus allows an activated B lymphocyte to assign a new functional role to its Ig molecules without altering antigenic specificity. This process greatly increases the functional diversity of the immune system without requiring a corresponding increase in B lymphocyte production to independently generate Ig molecules carrying the necessary combination of antigenic specificity and isotype function.

Switch recombination leads to site-specific deletions that originate directly upstream of the initial $C_H$ gene segment and terminate just prior to the newly expressed cassette of $C_H$ exons. Switch recombination breakpoints primarily fall within large (1–10 kb), highly repetitive "switch" regions found directly upstream of all $C_H$ genes that undergo switch recombination (Esser and Radbruch, 1990). Switch regions are primarily composed of degenerate tandem repeats of G-rich motifs with each switch (S) region having a characteristic repeat structure (Dunnick et al., 1993; Esser and Radbruch, 1990; Petrini and Dunnick, 1989; Petrini et al., 1987; Sakano et al., 1980; Szurek et al., 1985). Despite the structural differences among switch regions, three common switch pentamer motifs (TGAGC, TGGGC and TGGGG) are frequently detected at or adjacent to all analyzed switch breakpoints (Lyon and Aguilera, 1997; and references within).

The inventors and others (Aguilera et al., 1985; Lyon et al., 1996; Wuerffel et al., 1990) have proposed that switch recombination should require at least three distinct activities: (i) sequence-specific binding of switch repeat/recombination sequence motifs (referred to as SRSs in this proposal), (ii) endonucleolytic cleavage of targeted SRSs, and (iii) ligation of SRS free DNA ends. Several DNA binding factors have been identified that form specific interactions with murine SRSs (Fukita et al., 1993; Hanakahi et al., 1997; Marcu et al., 1992; Mizuta et al., 1993; Waters et al., 1989; Williams et al., 1993; Wuerffel et al., 1990; Xu et al., 1992), although none of these factors have yet been shown to play a direct role in switch rearrangement.

4.2 Regulation of Endo-SR/DNase II and its Potential Role in Switch Recombination and Apoptosis Based on these results, the inventors have proposed models to reconcile the potentially disparate roles of Endo-SR activity in isotype class switching and apoptosis. In the simplest model, strong surface IgM signaling would directly induce Endo-SR activity by intracellular acidification and or other protein modification. Signaling through the CD40 receptor, known to induce isotype class switching and repress acidification and apoptosis, should repress Endo-SR activity, but might not be sufficient to prevent cleavage of accessible high-affinity SRS recognition sites within accessible switch region DNA. Scission of SRS motifs by Endo-SR could then activate pre-existing B-cell specific "switching" factors (Rolink et al. 1996) to recombine the cleaved SRS. Surface IgM signaling in the absence of CD40-mediated survival signals, however, could promote the continuous activation of Endo-SR/DNase II activity by persistent intracellular acidification, resulting in nuclear DNA fragmentation. Several groups have shown that acidification is a common feature of apoptosis programs induced by highly distinctive cellular insults (Eastman, 1995; Walker and Sikorska, 1997), and it is tempting to propose that Endo-SR activity is regulated solely by environmental pH. Nuclease activity, however, could also be regulated independent of, or in conjunction with, cellular pH changes through phosphorylation/dephosphorylation, proteolytic processing, and/or protein-protein interactions. Finally, although it is tempting to speculate that Endo-SR/DNase II plays a dual role in apoptosis and switch recombination, this enzyme may function solely as a degradative nuclease activity during apoptosis (as appears to be the case in *C. elegans*).

In order to address the potential role(s) of the Endo-SR gene product, the inventors have disrupted the expression of this gene in B-cell lines and mice via targeted gene disruption. The generation of these Endo-SR mutant cells and animals may facilitate a more accurate determination of the cellular role of Endo-SR in switch recombination and apoptosis.

4.3 Clinical Applications of Endo-SR

Failure to degrade high molecular weight DNA is known to worsen the outcome of at least one genetic disease, cystic fibrosis, where the undigested DNA of lysed lung cells contributes to the accumulation of thick mucosal deposits resulting in a life-threatening pathological condition. Cystic fibrosis patients are currently treated with recombinant DNase I (Pulmozyme or Dornase α, Genentech) to alleviate this condition. Due to the highly potent nuclease activity of Endo-SR, this enzyme appears to represent an effective therapeutic alternative to recombinant DNase I therapy.

Endo-SR overexpression in mammalian cells results in severe cell viability losses in preliminary studies, potentially through activation of apoptosis by deregulated nuclear DNA degradation. Mammalian gene defects that elevate, repress, or deregulate Endo-SR/DNase II activity could also lead to severe developmental abnormalities including embryonic lethality and cancer if this nuclease is required for normal apoptosis. Any significant degree of aberrant cell death or survival could dramatically alter the normal embryonic pattern leading to potential failures in cell commitment to differentiate to specific tissues, cell lineages and cell types. Elevated expression of Endo-SR nuclease activity could also lead to increased oncogenesis as increased DNA damage could lead to activation of proto-oncogenes and/or inactivation of tumor suppressor genes. Repression of Endo-SR activity with the use of specially-designed chemical inhibitors may result in inhibition of potential aberrant rearrangements in patients exhibiting abnormal expression of the Endo-SR gene/protein.

Although the function(s) of Endo-SR in cellular and systemic DNA metabolism has yet to be determined in mammals, the apparent *C. elegans* homolog of this activity is known to play an important role in apoptosis and DNA degradation. Significant levels of active Endo-SR enzyme have been detected in animal sera implying that this enzyme may play a role in systemic nucleic acid clearance. Release of this enzyme into the serum may inhibit nucleic acid clot formation and may ultimately prevent the integration of foreign DNA into the host genome.

Endo-SR overexpression in mammalian cells results in severe cell viability losses in the studies, potentially through activation of apoptosis by deregulated nuclear DNA degradation. Mammalian gene defects that elevate, repress, or deregulate Endo-SR/DNase II activity could also lead to severe developmental abnormalities including embryonic lethality and cancer if this nuclease is required for normal apoptosis. Any significant degree of aberrant cell death or survival could dramatically alter the normal embryonic pattern leading to potential failures in cell commitment to differentiate to specific tissues, cell lineages and cell types. Elevated expression of Endo-SR nuclease activity could also lead to increased oncogenesis as increased DNA damage could lead to activation of proto-oncogenes and/or inactivation of tumor suppressor genes.

Endo-SR may play a major role in foreign DNA destruction, thereby protecting the host against potentially pathogenic foreign DNA. Specifically, this enzyme may degrade free intracellular DNA preventing viral infection by clearance of viral DNA prior to replication and/or integration into the host genome. Inactivation of this nuclease in animal models or human syndromes could therefore lead to an increased susceptibility to viral infections. The Endo-SR gene may be essential for normal embryonic development due to its potential role in apoptosis or may be necessary for the normal function of the immune system due to its potential role in antibody gene rearrangement. Gene therapy with Endo-SR gene constructs may therefore result in reversal of embryonic lethality or a "cure" for a potential life-threatening immunodeficiency.

4.4 Important Features of the Present Invention

Protein microsequencing of Endo-SR enzyme fraction produced only five extended (>5 aa) peptide sequences, representing three independent Endo-SR peptides (Lyon et al., 1998). Sequence homology searches performed with these three Endo-SR peptide sequences in 1997, revealed that each peptide exhibited significant similarity to the predicted amino acid sequence of a hypothetical 40 kDa human protein, R31240-2, of previously unknown function.

Protein homology searches conducted with the predicted amino acid sequence of R31240-2 revealed that this protein demonstrated significant similarity ($P(N)2.0e^{-37}$) to a hypothetical *Caenorhabditis elegans* protein, C07B5.5. Similarities were also detected to several proteins of known function, including potentially relevant similarities to DNA binding proteins and several enzymes involved in the reduction of phosphodiester and/or phosphate bonds, but all such matches were found to be below the significance threshold of these databases. Sequence analysis of the NCBI database of expressed sequence tags (ESTs) revealed that R31240-2 (Endo-SR) mRNA is expressed in a variety of different human cell types, including cells derived from lymph node, ovarian, prostate, neuronal, epithelial, and endothelial tissues (Lyon et al., 1998). These findings are consistent with results showing that Endo-SR is expressed at variable levels in all human, murine and bovine cell lines and tissues analyzed to date (Lyon and Aguilera, 1997; Lyon et al., 1998; Lyon et al., 1996). Based on these data the inventors have proposed that Endo-SR plays a role in cellular processes, aside from switch recombination, that are not restricted to the lymphoid cell lineage (Lyon and Aguilera, 1997).

In order to further characterize the putative human endo-sr (R31240-2) gene, this gene was cloned from a human pre-B cell line and tested for its ability to express the Endo-SR activity in vitro and in vivo. Although recombinant Endo-SR generated in rabbit reticulocyte extracts or bacteria was determined to be enzymatically inactive (likely due to a missing subunit-see Section E), overexpression of this protein in mammalian cells lead to a moderate increase (~4–6 fold) in Endo-SR activity. These results coupled with the cloning of the same gene by a group studying an acidic endonuclease (DNase II; 97), strongly supports the contention that the R31240-2 gene encodes the Endo-SR activity. The biochemical characterization of DNase II has revealed that this enzyme exhibits very similar biochemical and physical properties (pH optima, cation-independence, inhibition by $Zn^{2+}$, and molecular mass, etc.,) as Endo-SR (Collins et al., 1996; Lyon et al., 1998; Torriglia et al., 1997). Interestingly, DNase II has been proposed to be the major nuclease activated by intracellular acidification upon induction of apoptosis (Barry and Eastman et al., 1992; Eastman, 1995; Gottlieb et al., 1996; Meisenholder et al., 1996; Walker and Sikorska, 1997). Although there is some controversy regarding the necessity for acidification in apoptosis (Walker and Sikorska, 1997), intracellular acidification is apparently essential for nuclear DNA degradation in a variety of cell types (Gottlieb and Dosanjh, 1996; Gottlieb et al., 1996; Li and Eastman, 1995; Meisenholder et al., 1996; Moore et al., 1993; Morana et al., 1996; Park et al., 1996; Perez-Sala et al., 1995; Rebollo et al., 1995; Reynolds et al., 1996; Sharma et al., 1996; Sharma and Srikant, 1998). At least four additional nucleases have also been implicated in apoptosis: DNase I, Nuc-18, a $Ca^{2+}/Mg^{2+}$ dependent endonuclease, and a recently reported Caspase Activated Deoxyribonuclease (CAD). Due to the diversity of nuclease activities observed during apoptosis in different cell types, it has been proposed that more than one nuclease activity may be involved in apoptotic nuclear DNA degradation (Walker and Sikorska, 1997). Studies described in this proposal will address the relevance of Endo-SR/DNase II to apoptosis.

Programmed cell death in *C. elegans* and mammals is highly similar involving ICE proteases (CED-3 in *C. elegans*), Bcl-2 (CED-9 in *C. elegans*), and most likely additional homologous or highly related proteins (Driscoll, 1997; Hengartne, 1997). Furthermore, an acidic endonuclease implicated in DNA degradation in *C. elegans* has strong biochemical similarities with mammalian Endo-SR/DNase II. *C. elegans* deficient in this acidic endonuclease activity (nuc-1 mutants) are viable but contain apoptotic cells with persistent undegraded nuclear DNA (Hevelone and Hartman, 1988; Sulston, 1976).

Since mammalian Endo-SR/DNase II proteins demonstrate significant sequence similarity to the predicted *C. elegans* protein C07B5.5, the inventors have tested protein extracts derived from wild-type *C. elegans* for an Endo-SR/DNase II-like activity. Wild-type *C. elegans* protein extracts contain a potent endonuclease activity that readily degrades supercoiled plasmid DNA under acidic pH conditions. Nuclease activity detected in these extracts was found to cleave a switch region DNA substrate in a pattern very similar to those produced by several mammalian Endo-SR/DNase II activities. Specifically, the *C. elegans* acidic nuclease activity produces DNA breaks at each G-rich switch motif, roughly similar to species-specific breaks produced by several mammalian Endo-SR/DNase II activities (Lyon and Aguilera, 1997; Lyon et al., 1998; Lyon et al., 1996), and generates an identical cleavage at a TAGAG motif recognized by all mammalian enzymes. Since nuc-1 mutant animals are known to be deficient (less than 1% of wild-type levels) in an acidic nuclease activity (Hevelone and Hartman, 1988), the inventors also tested protein extracts derived from these mutant animals for alterations in the Endo-SR/DNase II-like activity detected with wild-type extracts. Protein extracts derived from nuc-1 mutant worms contain extremely low levels of acidic nuclease activity (<0.5% of wild-type) and the residual endonuclease activity in these animals demonstrates a specificity indistinguishable from that found in wild-type extracts. These results not only confirm the results of Hevelone and Hartman (1988) regarding the leaky nature of the mutation but also strengthen the contention that only one acidic nuclease can be detected with a highly-sensitive nuclease assay.

Since nuc-1 and the putative *C. elegans* DNase II-like enzyme encoded by the C07B5.5 gene map to distinct positions on chromosome X (~7 map units apart), it seems unlikely that the C07B5.5 gene is the allele affected in nuc-1 mutant animals (Riddle et al., 1997). One possible explanation for this discrepancy is that the *C. elegans* acidic nuclease is a heterodimeric enzyme whose subunits are encoded by the C07B5.5 and nuc-1 genes. Mutations affecting the activity of either nuclease subunit would therefore be expected to result in highly similar if not identical phenotypes. Significantly, porcine and bovine spleen DNase II has been determined to exist as heterodimeric proteins in which both subunits are necessary for enzyme activity (Liao, 1985).

Surface IgM (sIgM) crosslinking stimulates B cells to initiate apoptosis, but can also induce these cells to proliferate or undergo switch recombination when combined with synchronous activation of additional signaling pathways (Purkerson and Isakson, 1992). Switch recombination, for example, can be efficiently induced by sIgM crosslinking in conjunction with cell-cell contact and cytokine stimulation (Esser and Radbruch, 1990; Mayumi et al., 1994; Purkerson and Isakson, 1992). One of the most important of these external signals is mediated by the interaction of the B lymphocyte receptor protein CD40 with its ligand, CD40L, on activated T-helper cells (Purkerson and Isakson, 1992; Tsubata et al., 1993). The CD40 mediated signal synergizes with signals provided by multivalent surface Ig crosslinking and specific cytokines (such as IL-4 and IL-5) to induce isotype class switching (Castigli et al., 1994; Kawabe et al., 1994; and references within). Signals through CD40 have been shown to inhibit sIgM-mediated apoptosis by inducing bcl-2 and/or bcl-$X_L$ expression (Aikifusa et al., 1998; Choi et al., 1995; Koizumi et al., 1996; Wilson et al., 1996). There is recent evidence that Bcl-2 expression blocks intracellular acidification generated in response to sIgM crosslinking, although the mechanism responsible for this interference is not yet known (Aikifusa et al., 1998).

4.5 Immune Response

The vertebrate immune system can recognize a vast array of potentially harmful foreign molecules, and as a consequence of this ability can often act to prevent damage caused by exposure to many foreign pathogens. Although a number of the "innate" mechanisms that contribute to this process are relatively non-specific, an "acquired" or "adaptive" immune response can be highly selective for a specific antigen. Adaptive immunity, however, requires the immune system to recognize, and differentiate among, a vast number of potential antigens, and in order to accomplish this task the immune system must produce a correspondingly large repertoire of antigen receptors.

Both B- and T-lymphocytes synthesize antigen receptors required for adaptive immunity, and the ability to mount an effective immune response depends upon the ability of each of these cell types to synthesize diverse populations of antigen receptors. In both cases, receptor diversity is generated by regulated, site-specific somatic recombination of a few antigen receptor genes, and further increased by the subsequent combinatorial association of these receptor subunits (Jessberger and Lieber Eds., 1996). Each B cell, for example, synthesizes a unique immunoglobulin heavy chain (IgH) and light chain (IgL) gene from an array of germline-encoded gene segments (FIG. 4A and FIG. 4B). Synthesis of the antigen binding or "variable" region of both of these receptors requires the site-specific recombination of variable (V), diversity (D) and/or a joining (J) gene segments. The IgH gene variable region is assembled from V, D and J gene segments, while the IgL gene is synthesized from V and J gene segments. All V(D)J rearrangements produce a "chimeric" antigen binding sight directly upstream of a constant region (C) gene segment, but only those that form functional IgH and IgL genes capable of surface expression result in differentiation to an antigen-responsive mature B cell stage (Kitamura et al., 1991; Young et al., 1994; Spanopoulou et al., 1994). Receptor diversity is generated, in part, by the junctional diversity introduced during the resolution of V(D)J recombination breakpoints within variable region gene elements and further increased by the random addition or deletion of nucleotides at these recombination junctions.

Immunoglobulin (Ig) molecules are assembled from rearranged IgH and IgL subunits, further increasing receptor diversity, to create a divalent receptor molecule containing two identical IgH and IgL subunits. Receptor specificity is determined by association of the IgH and IgL variable regions to form a unique antigen-binding site. However, antigen receptors do not demonstrate a restricted specificity for "foreign" antigens, and the precise discrimination between "self" and "non-self" antigens that is required for adaptive immunity is generated by the selective elimination of lymphocytes bearing "self-reactive" antigen receptors (Han et al., 1996). Lymphocytes that are not removed by this "self-tolerance" mechanism remain quiescent until they encounter antigens that match their receptor specificity.

Stimulation of B- and T-lymphocytes by antigen recognition results in the rapid clonal expansion of the affected cells. Stimulated B cell clones can differentiate to produce primary plasma cells that secrete relatively low-affinity IgM and IgD or germinal center B cells that are activated by future exposure to their specific antigen. Subsequent antigen exposure induces germinal center B cells to undergo somatic hypermutation of their Ig genes, resulting in increased receptor affinity. Secondary antigen exposure can also induce germinal center B cells to express an alternate Ig classes or "isotype" when coupled with exposure to certain cytokine signals.

4.6 Chromosomal Rearrangements Involved in Switch Recombination Events

Mature B lymphocytes are able to selectively "switch" Ig isotypes during the course of an adaptive immune response through a site-specific DNA rearrangement process that deletes one cassette of IgH constant-region ($C_H$) exons and replaces them with one of six different sets of $C_H$ exons (Honjo and Kataoka, 1978; Davis et al., 1980; Sakano et al., 1980). Naïve B lymphocytes initially express IgM, with or without IgD, but can be selectively induced to express IgG3, IgG1, IgG2b, IgG2a, IgE or IgA in response to stimuli resulting from different types of primary immune responses (Purkerson and Isakson, 1992a). Each Ig isotype has a specific distribution pattern and a distinctive role in the adaptive immune response. Switch recombination thus allows an activated B lymphocyte to assign a new functional role to the mature antigenic specificity of its Ig molecules.

This process greatly increases the functional diversity of the immune system without requiring a corresponding increase in B lymphocyte production to independently isolate Ig molecules carrying the necessary combination of antigenic specificity and isotype function.

Naïve B lymphocytes initially express only surface (s) IgM, but can subsequently express both sIgM and sIgD through alternate splicing of the primary IgH gene transcript (Blattner et al., 1984; Knapp et al., 1982; Maki et al., 1981). Significantly, however, the murine $C_H$ genes that encode the IgM and IgD isotypes ($C_\mu$ and $C_\delta$, respectively) are located almost directly adjacent to each other while those encoding alternate isotypes are located approximately 50–200 kb more distant along the germline chromosome (Shimizu et al., 1982). B-lymphocytes do not "switch" to IgD expression, and normally express sIgD only as a result of this alternate-splicing event (Blattner et al., 1984; Knapp et al., 1982; Maki et al., 1982; White et al., 1990; Owens et al., 1991). Switch rearrangement is, however, required for the expression of all other Ig isotypes. All mammalian IgH loci analyzed to date contain a tandem array of at least eight $C_H$ gene segments spanning a broad region of the germline chromosome. Murine $C_H$ gene segments, for example, are arranged 5'-$C_\mu$-$C_\delta$-$C_\gamma 3$-$C_\gamma 1$-$C_\gamma 2b$-$C_\gamma 2a$-$C_\epsilon$-$C_\alpha$-3', and span approximately 200 kb of the IgH gene locus (Shimizu et al., 1982). B-lymphocytes are able to "switch" their expressed isotype through the regulated and precise deletional rearrangement of the $C_H$ gene segments within these arrays (Purkerson and Isakson, 1992a; Davis et al., 1980; Sakano et al., 1980). Switch recombination events result in site-specific deletions that originate directly upstream of the initial $C_H$ gene segment and terminate just prior to the newly expressed cassette of $C_H$ exons (FIG. 5). Switch recombination can therefore result in variable degrees of B cell differentiation, since each isotype switch results in the deletion of a different number of $C_H$ gene segments, eliminating any possibility of their future expression.

Switch recombination breakpoints primarily fall within large (1–10 kb), highly repetitive "switch" regions found directly upstream of all IgH constant region genes that undergo switch recombination (Davis et al., 1980; Sakano et al., 1980). Switch regions are primarily composed of degenerate, G-rich variable-length repeat units that vary considerably both within and across species. The murine switch elements, for example, range from 20–80 nucleotides in length and are each associated with a single switch region (Nikaido et al., 1981; Stanton and Marcu 1982; Kataoka et al., 1981; Nikaido et al., 1982; Obata et al., 1981; Davis et al., 1980). Sequence analysis of murine switch region DNA has also revealed that, based upon their sequence composition, all switch (S) regions can be grouped into two distinct families; one containing S$\mu$, S$\epsilon$ and S$\alpha$ and the other composed of S$_\gamma$3, S$_\gamma$1, S$_\gamma$2b and Sy2a (Stanton and Marcu, 1982). Sequence homologies associated with each "family" of switch regions most likely reflect sequence divergence generated and preserved during duplication of the ancestral $C_H$ exons to create the tandem array of $C_H$ gene segments present in the modem IgH locus. Switch region composition does not appear to substantially influence switch rearrangement, since different switch region families can be rearranged in the same cell line (Lepse et al., 1994), indicating that these events may be regulated by the same "switch recombinase" components.

Sequence analysis of murine switch region sequence has shown that S$\mu$, the constitutively accessible "default" switch region, demonstrates the greatest sequence homology to S$\epsilon$, followed by S$\alpha$, S$\gamma$3, S$\gamma$1, S$\gamma$2b and finally by S$\gamma$2a (Stanton and Marcu., 1982; Nikaido et al., 1982). However, all switch regions reveal fundamental underlying similarities despite significant differences in the length and composition of their constituent repeat elements. For example, all switch regions contain disproportionate numbers of two pentamer motifs, TGGGN and TGAGC, which are found at or adjacent to the majority of analyzed switch recombination breakpoints (Stanton and Marcu, 1982; Petrini and Dunnick, 1989). Several switch regions (S$\mu$, S$\epsilon$ and S$\alpha$,) are almost exclusively composed of degenerate tandem repeats of these two motifs, while the remaining switch regions (S$\gamma$3, S$\gamma$1, S$\gamma$2b and S$\gamma$2a) contain scattered examples of these motifs within their switch repeat elements.

Recombination sites within murine S$\gamma$, S$\epsilon$ and S$\alpha$ region DNA, with few exceptions (<10%), occur within regions composed of tandemly repeated switch elements (Dunnick et al., 1993). S$\mu$ rearrangements do not appear to demonstrate this degree of specificity, since ~40% of all S$\mu$ recombination breakpoints fall outside S$\mu$ tandem repeat regions, and most of these sites fall 5' of S$\mu$ region DNA. Rearrangements at S$\mu$ thus appear to demonstrate a marked preference for the 5' region of S$\mu$, unlike the apparently random distribution of recombination sites detected within all other analyzed switch regions. Based on these differences, it seems likely that the switch recombination process either directly or indirectly differentiates between rearrangement events at S$\mu$ and those at other switch regions.

All initial switch recombination events proceed through recombination of S$\mu$ with one of the six downstream switch regions, and S$\mu$ can thus be considered the switch "donor" region for all primary switch recombination events. Switch rearrangements recombine a switch "donor" region with a selectively activated switch "acceptor" region resulting in the deletion of all intervening sequence and the creation of a switch region "chimera" derived from switch donor and acceptor sequence. Switch recombination is not necessarily a terminal differentiation step, however, and some B cells undergo "secondary" switch rearrangements (Petrini and Dunnick, 1989; Jabara et al., 1993; Mandler et al., 1993b; Jung et al., 1994; Zhang et al., 1994; Mills et al., 1995). Secondary or "sequential" switch rearrangements can fall within an existing switch region chimera or between this region and another activated switch region. Significantly, sequential switch recombination may explain the biased 5' distribution of S$\mu$ rearrangement breakpoints since secondary rearrangement of a S$\mu$L-Sx chimera would be expected to result in the progressive 3' deletion of S$\mu$ region DNA sequence. Sequential switching has also been proposed as a possible means of stabilizing the expression of a particular isotype (Zhang et al., 1995), since progressive deletion of a switch region chimera could be expected to reduce the ability of this region to support further switch rearrangements. Switch chimeras are also apparently able to function as switch donor regions in "secondary" recombination events, and secondary switch junctions do not always fall within S$\mu$ DNA, indicating that alternative switch region sequences can function as switch donors when fused to S$\mu$.

Surprisingly little is known about the precise mechanism of switch recombination. Switch recombination, like all site-specific rearrangement events, appears to require sequence-specific DNA binding, cleavage and ligation. Switch recombination appears to require a double strand break event, since switch breakpoint junctions sometimes contain short insertions of exogenous DNA sequence (Dunnick et al., 1993). Switch rearrangements also appear to require the specific synapsis of the two recombinationally active switch regions in order to promote efficient rearrangement, since switch recombination breakpoints may be separated by as much as 200 kb of intervening chromosomal DNA. Several lines of evidence suggest that chromosomal DNA looping and switch region synapsis occurs during recombination. Specifically, recombination can result in the deletion or inversion of the synapsed chromosomal DNA region, and both events are characteristic of the switch recombination process (Jäck et al., 1988; Siebenkotten et al., 1992). Switch deletions are required for expression of a secondary Ig isotype, but switch inversions disable IgH synthesis since all such rearranged alleles are unable to transcribe a functional $C_H$ gene segment (FIG. 6). Switch recombination appears to generate almost as many inversions as deletions in a pre-B cell line lacking selection for sIg expression (Jack et al., 1988), suggesting that the switch recombination process does not directly specify the orientation of the switch rearrangement.

Switch circles, the reciprocal deletion products of switch recombination, are associated with all deletional switch recombination events and are produced in direct correlation with switch recombination frequency (von Schwedler et al., 1990; Iwasato et al., 1990; Matsuoka et al., 1990). Switch junctions found in all analyzed switch circles strongly resemble those detected within switch region chimeras (Dunnick et al., 1993), suggesting that switch circle ends are not subjected to prolonged exposure to the highly active B cell nucleases. Significantly, however, both switch circle and chromosomal recombination breakpoints demonstrate frequent insertions, implying that all the free DNA ends generated during switch rearrangement are susceptible to modification during the recombination process (Dunnick et al., 1993).

Switch rearrangements, despite the fundamental sequence homologies of the rearranged switch regions, do not appear to be regulated by a homologous recombination mechanism, since switch breakpoints demonstrate very limited sequence homology. Specifically, at recombination sites where both donor and acceptor sequences are known, less than 8% share more than 3 bp, 25% share only a single bp and 39% do not share any sequence homology (Dunnick et al., 1993). Sequence analysis of these regions has, furthermore, demonstrated that this degree of sequence homology is consistent with that expected to result from chance alone (Dunnick et al., 1993). Nonhomologous DNA recombination does not require any breakpoint sequence homology in order to efficiently join free DNA ends, but this process has sometimes been shown to proceed through short internal or breakpoint sequence homologies (Roth and Wilson, 1986) and can produce sequence overlaps consistent with those detected at switch junction breakpoints. Significantly, resolution of non-homologous recombination intermediates sometimes requires single-strand DNA excision and repair, and results lend support to this mechanism of switch junction resolution in that asymmetric, directional mutation detected at switch junctions (Li et al., 1996a) appears likely to result from error-prone DNA synthesis.

Switch recombination appears to be directed by a highly imprecise mechanism that does not specify rearrangement orientation or exact recombination junctions. Switch recombination also fails to demonstrate absolute fidelity for switch region sequence, since several examples of aberrant switch rearrangements, primarily with proto-oncogene chromosomal loci, have been isolated from cultured B cell lines (Ohno et al., 1991; Janz et al., 1993; Kadowaki et al., 1995; Bergsagel et al., 1996; Chesi et al., 1996). Since switch recombination is thus potentially a highly mutagenic process, it seems reasonable that this process would be tightly regulated during B-lymphocyte development. Results support this contention, since efficient switch recombination appears to be not only B cell lineage-specific, but also B cell stage-specific; and is restricted to the late pre-B to mature-B stages of B-lymphocyte differentiation (Ballantyne et al., 1997). Stage- and lineage-specific switch recombination restriction appears to apply only to switch regions found within a chromosomal DNA context (Ott et al., 1987; Ott and Marcu, 1989; Ballentyne et al, 1995, 1997), since replicating extrachromosomal switch substrates demonstrate significant recombination in inappropriate cell types (Leung and Maizels, 1992, 1994; Daniels and Lieber 1995). Switch recombination specificity for a given DNA substrate thus appears to be primarily regulated by its accessibility to switch factors not restricted to the B lymphocyte cell lineage.

4.7 Regulation of Switch Recombination in B Lymphoctyes

Significantly more is known about the regulation of switch recombination than is known about its mechanism. A substantial body of evidence indicates that class switch recombination is regulated, in conjunction with the control of B lymphocyte proliferation and differentiation, by signal transduction pathways requiring contact-dependent interactions and/or adsorption of soluble factors. Efficient induction of switch recombination appears to require the synergistic action of at least three distinct signals: sIg crosslinking, CD40 engagement and lymphokine exposure (Purkerson and Isakson, 1992a). Substantial effort has been focused on determination of the specific signals resulting from these events, but while several events connected with the recombination process have been associated with individual signal transduction pathways very little is known about the intervening steps that produce these events.

Surface Ig cross-linking stimulates self-reactive B cells to initiate apoptosis and undergo programmed cell death (Nossal, 1994), but can also signal similar, "non-self" specific B cells to undergo a number of additional B cell proliferation and differentiation responses, including switch recombination. In order to permit B cells that recognize foreign antigens to proliferate and/or differentiate in response antigenic stimulation, secondary signals are required to offset the inhibitory signals initiated by sIg cross-linking. Switch induction, for example, is mediated by synchronous activation of the sIg and CD40 signal transduction pathways in conjunction with simultaneous or subsequent exposure to specific cytokines (Purkerson and Isakson, 1992a). Results from several groups have shown that stimulation of CD40 signaling alone is sufficient to counteract the induction of sIg-mediated cell cycle arrest and apoptosis (Tsubata et al., 1993).

CD40 is a 45–50 kDa transmembrane glycoprotein expressed on mature B cells (Paulie et al., 1985, Clark and Ledbetter, 1986) as well as certain accessory cells (Schriever et al., 1989; Hart and Mackenzie, 1988; Alderson et al., 1993; Galy and Spits, 1992). CD40 belongs to the same receptor family as Fas (Itoh et al., 1991), another protein directly involved in the regulation of programmed cell death, and specifically interacts with CD40 ligand (CD40L) present on activated $CD4^+$ helper T cells (Armitage et al., 1992). Stimulation of CD40 results in a complex pattern of secondary events including the activation or repression of several kinases and transcription factors. Specifically, CD40 activation has been reported to regulate the activity of several protein tyrosine kinases, including Lyn, Fyn and Syk; the activation of phosphatidyl-inositol-3 kinase; and the phosphorylation of phospholipase Cγ2 (Uckun et al., 1991; Faris et al., 1994; Ren et al., 1994b). CD40 stimulation has also been shown to result in the activation of the Rel/NFκB family of transcription factors (Berberich et al., 1994) and the induction of A20 (Sarma et al., 1995), a novel zinc-finger protein implicated in the regulation of apoptosis.

Stimulation of CD40 signaling by receptor cross-linking results in the rapid activation of several distinct signal transduction pathways, is independent of de novo protein synthesis, and can be efficiently blocked by prior exposure to specific kinase inhibitors (Knox and Gordon, 1993; Ren et al., 1994a; Loh et al., 1994b; Faris et al., 1994; Worm and Geha, 1995; Li et al., 1996c). Signal transduction through CD40 requires the conservation of a short region of the CD40 cytoplasmic tail, although this region does not contain any inherent phosphatase or kinase activities. Specific deletion of a region spanning amino acids 246–269 of the human CD40 cytoplasmic tail abolishes receptor-mediated repression of apoptosis and the specific activation of NFκB, JNK and ERK2 (Li et al., 1996c; Hara, 1997). Several proteins have recently been shown to form specific interactions with the CD40 cytoplasmic tail, and the majority of these belong to a family of TNF receptor associated factors (TRAFs). Several of these factors, including TRAF2, TRAF3 and TRAF5 have been shown to specifically bind a functionally important region spanning amino acids 246–269 of the CD40 cytoplasmic tail (Hu et al., 1994; Ishida et al., 1996b), while another related protein, TRAF6, has been shown to interact with a site immediately adjacent (aa's 230–245) to this site (Ishida et al., 1996a). Significantly, overexpression of TRAF2, TRAF5 or TRAF6, but not TRAF3, has been shown to activate NFκB, one of several proteins activated by CD40 cross-linking (Ishida et al., 1996b; Takeuchi et al., 1996; Aizawa et al., 1997), directly implicating these factors in at least one of the events activated regulated by signal transduction through the CD40 receptor. JAK3 has also recently been shown to be constitutively associated with a proline-rich region of the CD40 cytoplasmic tail, and specific deletion of this region has been shown to directly abolish the ability of CD40 to induce expression of CD23, ICAM-1 and the lymphotoxin-α genes in response to CD40 cross-linking (Hanissian and Geha, 1997). Signal transduction through CD40 thus appears to be a complex process involving specific recognition of at least three distinct sites within the CD40 cytoplasmic tail by at least two distinct families of signal transduction factors.

Signal transduction through the CD40 cytoplasmic tail has been shown to rapidly induce NFκB gene activity (Berberich et al., 1994), and several lines of evidence demonstrate that p50/NFκB expression plays an important role in the normal induction of switch recombination. p50-binding sites have been identified in the regulatory promoter regions of three $C_H$ genes (Iγ3, Iγ1 and Iε; Gerondakis et al., 1991; Lin and Stavnezer, 1996; Delphin and Stavnezer, 1995); in three 3' Cα enhancer elements (HS1, HS2 and HS4; Michaelson et al., 1996); and in Sγ3, Sγ1 and Sγ2b in proximity to known switch recombination sites (Wuerffel et al., 1990, 1992; Kenter et al., 1993). Recombinant mice deficient in p50/NFκB gene expression (p50$^{-/-}$) reveal selective defects in the activation, and subsequent rearrangement to, certain $C_H$ loci relative to wild-type controls (Snapper et al., 1996). Switch defects are detected at $C_H$ loci with (IgG3 and IgE) or without (IgA) significantly reduced $C_H$ expression, indicating that NFκB may regulate switch recombination through more than one mechanism. It has also been shown that the activation of A20 gene expression is mediated by the inducible binding of NFκB to two κB sites within the A20 promoter region (Sarma et al., 1995).

Significantly, the overexpression of A20 has been shown to render B cell lines resistant to the induction of programmed cell death (Sarma et al., 1995). Resistance to cell death conferred by A20 expression appears to be selective for certain apoptotic signals, however, since A20 expression protects B cell lines against apoptosis after serum starvation but not after glucocorticoid exposure. It has been demonstrated that A20 can specifically interact with the TRAF domains of TRAF1 and TRAF2 to block CD40 association and thereby prevent subsequent activation of NFκB in response to CD40 engagement (Song et al., 1996).

Stimulation of CD40 is required to counteract several of the inhibitory signals associated with sIg cross-linking. Specifically, CD40 signaling has been shown to block apoptosis, stimulate arrested cells to reenter the cell cycle, and synchronize with sIg activation to induce the activation of the NFκB transcription factor. Signals transmitted through CD40 appear to regulate sIg control of apoptosis and cell cycle arrest through the reactivation of Bcl-$x_L$ and Cdk2 or Cdk4/Cdk6 expression. Stimulation of A20 expression appears likely to be one of the initial steps in the restoration of Bcl-$x_L$ expression, due to this proteins known role in the prevention of apoptosis. However, the signal(s) required to directly restore Cdk2 activity and Cdk4/Cdk6 expression are as yet unknown.

Synchronous sIg and CD40 activation is required, but not sufficient, for efficient induction of switch recombination. Signals provided by cytokines are also necessary for efficient and selective induction of switch recombination events. Naïve B-lymphocytes can be selectively induced to switch to specific isotypes during in vitro culture in response to mitogen stimulation and exposure to specific lymphokines (Purkerson and Isakson, 1992a). For example, murine splenic B cells activated by in vitro culture with lipopolysaccharide (LPS) can be selectively induced to express IgG3 and IgG2a by addition of interferon γ (IFN-γ), IgG1 and IgE by addition of interleukin-4 (IL-4) or IgG2b and IgA by addition of transforming growth factor β (TGF-β). Sterile $C_H$ germline transcripts induced by these lymphokines directly corresponds with the subsequent preferential rearrangement of these genes (Gaff et al., 1992; Goodman et al., 1993). Selective rearrangement to a specific isotype, however, appears to require the integration of several distinct switch signals. For example, efficient induction of selective IgA expression appears to require sIg cross-linking, CD40 ligand (or LPS) exposure, IL-4, IL-5 and TGF-β (Shparago et al., 1996).

4.8 Regulatory Model for the Activation of Switch Recombination

Specific activation of a particular switch DNA region appears to selectively target switch rearrangement to that site, and has lead to the proposal of an "accessibility model" for switch recombination (Stavnezer-Nordgren and Sirlin, 1986; Yancopolous et al., 1986). In this model, alterations in switch region chromatin structure, resulting from de novo transcriptional activation, are proposed to increase the accessibility of switch region regulatory elements to "switch recombinase" factors. Significantly, a similar model of chromatin accessibility has been demonstrated to regulate the selective rearrangement of cell-type specific antigen receptor genes during V(D)J recombination (Stanhope-Baker et al., 1996). Studies have shown that recombinant mice with transcription defects at specific $C_H$ loci fail to rearrange the affected switch regions. Specific inactivation of Sμ transcription, for example, strongly represses Sμ rearrangement but does not appear to significantly affect Sγγ1 rearrangement (Zhang et al., 1993), while specific deletion of Iγ1 selectively abolishes Sγ1 rearrangement (Jung et al., 1993). Switch region transcription per se does not appear to activate switch recombination, since it has been shown (Bottaro et al., 1994) that specific replacement of Iϵ with an inducible Eμ/$V_H$ promoter construct dramatically reduces switch recombination to Cϵ despite significant levels of inducible Cϵ transcription.

Selective switch rearrangements also do not appear to result solely from cytokine-induced transcriptional activation of particular $C_H$ gene loci, since some lymphokines that have no significant demonstrable effect upon sterile transcript production, including IL-5 and IL-10, appear to strongly influence the efficiency of switch recombination events (Mandler et al., 1993a; Purkerson and Isakson, 1992b; Shparago et al., 1996). IL-5 was initially characterized by its ability to induce B-cell proliferation and stimulate Ig secretion, but studies have shown that IL-5 also stimulates switching to IgG1 and IgE without corresponding increases in the levels of Cγ1 and Cϵ germline RNA transcripts (Purkerson and Isakson, 1992b). Signals involved in specific switch induction events may also exert both positive and negative effects, significantly enhancing rearrangement to one $C_H$ loci while simultaneously repressing recombination to another. For example, addition of IL-10 to cultured murine B lymphocytes stimulated to switch to IgG3 or IgG1 appears to substantially enhance Sμ-Sγ3 and Sμ-Sγ1 rearrangements (Briere et al., 1994; Malisan et al., 1996), while similar addition of IL-10 to cells stimulated to switch to IgA expression can strongly inhibit Sμ-Sα rearrangement (Shparago et al., 1996). Inhibition of Sμ-Sα rearrangements by IL-10 may reflect antagonistic interference specific to a particular activation pathway, however, since another study demonstrates that IL-10 significantly enhances the ability of cultured murine B cells to switch to IgA expression (Defrance et al., 1992).

Research into the regulation of switch recombination, as discussed above, has demonstrated that switch induction requires the synchronous activation at least three different regulatory pathways. Switch recombination appears to require both active cell proliferation (Severinson et al., 1982; Kenter and Watson, 1987; Lundgren et al., 1995) and $C_H$ gene transcription. However, several events that have no discernable affects upon these processes have also been shown to effect recombination. Results have shown that several cytokines, including IL-5 and IL-10, regulate switch recombination in a manner that is independent of their ability to activate $C_H$ gene transcription or cell proliferation (Mandler et al., 1993a; Purkerson and Isakson, 1992b; Shparago et al., 1996). Switch recombination can also be directly regulated by at least two asthma drugs, disodium cromoglycolate (Loh et al., 1994a) and nedocromil sodium (Loh et al., 1995), that dramatically repress switch rearrangement without demonstrably affecting cell proliferation or specific induction of $C_H$ gene transcription.

Selective $C_H$ gene transcription has been proposed to regulate the switch region accessibility to switch recombinase factors (Stavnezer-Nordgren and Sirlin, 1986; Yancopolous et al., 1986), while de novo DNA synthesis associated with S phase reentry has been implicated in the error-prone resolution of switch recombination junctions (Li et al., 1996a). Significantly, these two events are likely the first and last steps, respectively, of a switch recombination event. Switch signals not associated with either of these two pathways thus appear likely to regulate the intermediate steps of switch recombination: site-specific DNA binding and/or cleavage. Signals affecting this process could directly activate switch recombination by regulating the de novo expression or activity of several as yet undefined switch recombinase factors.

Surprisingly, however, despite considerable effort, no one has yet identified any protein that is definitively associated with a proposed switch recombinase complex. Several groups have identified cell-specific and/or inducible switch DNA binding factors (Waters et al., 1989; Wuerffel et al., 1990; Williams and Maizels, 1991; Xu et al., 1992; Marcu et al., 1992; Fukita et al., 1993; Mizuta et al., 1993; Williams et al., 1993; Miranda et al., 1995), although many of these proteins have subsequently been shown to function as regulatory transcription factors through interaction with specific sites within individual $C_H$ promoter regions. None of these proteins have yet been shown to directly affect the switch recombination process. RAD51, a highly-conserved eukaryotic protein implicated in recombination-dependent double-strand break repair, has also recently been proposed as a switch recombinase component based on its specific spatial and temporal activation upon switch induction (Li et al., 1996b). Recombinant mice deficient in RAD51 expression die early in embryonic development (Tsuzuki et al., 1996), and no homozygous mutant (RAD51$^{-/-}$) B cell line mutants have yet been generated to address the relevance of RAD51 expression to switch recombination. Work, however, has demonstrated that another cellular housekeeping protein, the DNA-dependent serine/threonine protein kinase (p350/DNA-PK), is absolutely required for normal switch recombination (Rolink et al., 1996). Recombinant mice homozygous for the severe combined immune deficiency defect (SCID, p350$^{-/-}$) do not reveal detectable levels of switch rearrangement after switch induction, despite wild-type levels of $C_H$ gene transcription. Switch recombination does not appear likely to be directly mediated by DNA-PK, since the Ku76/Ku80 DNA binding proteins recruits this enzyme to various different DNA defects, including hairpins, nicks and double-strand breaks (Paillard and Strauss, 1991; Morozov et al., 1994). Due to this lack of specificity, it appears likely that DNA-PK is required for the resolution of switch breakpoint ends, but is not directly involved in the switch recombination process as a regulated switch recombinase component.

4.9 Pharmaceutical Compostions

In certain embodiments, the present invention also concerns formulation of one or more of the polynucleotide compositions disclosed herein in pharmaceutically-acceptable solutions for administration to a cell or an animal, either alone, or in combination with one or more other modalities of therapy.

It will also be understood that, if desired, the nucleic acid segment, RNA, DNA or PNA compositions disclosed herein may be administered in combination with other agents as well, such as, e.g., proteins or polypeptides or various pharmaceutically-active agents. As long as the composition comprises at least one Endo-SR composition, there is virtually no limit to other components which may also be included, given that the additional agents do not cause a significant adverse effect upon contact with the target cells or host tissues. The RNA, DNA, or PNA-derived sense or antisense compositions may thus be delivered along with various other agents as required in the particular instance. Such RNA, DNA, or PNA compositions may be purified from host cells or other biological sources, or alternatively may be chemically synthesized as described herein. Likewise, such compositions may comprise substituted or derivatized RNA, DNA, or PNA compositions. In the case of antisense therapies, such compositions may include modified peptide or nucleic acid substituent derivatives, as long as the base sequence of the RNA, DNA, or PNA molecule corresponds to one or more of the contiguous base sequences described herein that specifically bind to Endo-SR mRNA, and that reduce or inhibit the extent of translation of Endo-SR mRNA into biologically-active Endo-SR polypeptide.

The formulation of pharmaceutically-acceptable excipients and carrier solutions are well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

4.9.1 Oral Delivery

The pharmaceutical compositions disclosed herein may be delivered via oral administration to an animal, and as such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. No. 5,641,515; U.S. Pat. No. 5,580,579 and U.S. Pat. No. 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as those containing sodium borate, glycerin and potassium bicarbonate, or dispersed in a dentifrice, including: gels, pastes, powders and slurries, or added in a therapeutically effective amount to a paste dentifrice that may include water, binders, abrasives, flavoring agents, foaming agents, and humectants, or alternatively fashioned into a tablet or solution form that may be placed under the tongue or otherwise dissolved in the mouth.

4.9.2 Injectable Delivery

Alternatively, the pharmaceutical compositions disclosed herein may be administered parenterally, intravenously, intramuscularly, or even intraperitoneally as described in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g, glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

4.9.3 Nasal Delivery

The compositions of the invention may also be administered by intranasal sprays, inhalation, and/or other aerosol delivery vehicles. Methods for delivering genes, nucleic acids, and peptide compositions directly to the lungs via nasal aerosol sprays has been described e.g., in U.S. Pat. No. 5,756,353 and U.S. Pat. No. 5,804,212 (each specifically incorporated herein by reference in its entirety), and delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

4.9.4 Additional Modes of Delivery for Endo-SR Compounds

In addition to the methods of delivery described above, the following techniques are also contemplated as alternative methods of Endo-SR composition delivery. Sonophoresis (i.e., ultrasound) has been used and described in U.S. Pat. No. 5,656,016 (specifically incorporated herein by reference in its entirety) as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. No. 5,770,219 and U.S. Pat. No. 5,783,208) and feedback controlled delivery (U.S. Pat. No. 5,697,899), each specifically incorporated herein by reference in its entirety.

4.10 Delivery Methods and Compositions 4.10.1 Liposome-, Nanocapsule-, and Microparticle-Mediated Delivery In certain embodiments, the inventors contemplate the use of liposomes, nanocapsules, microparticles, microspheres, lipid particles, vesicles, and the like, for the introduction of the polynucleotide and/or polypeptide compositions of the present invention into suitable host cells. In particular, the oligonucleotide or polypeptide compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids and polypeptides disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon and Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., 1990; Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989; Fresta and Puglisi, 1996), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b;

Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins such as cytochrome c bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the polynucleotide compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1980; 1988; zur Muhlen et al., 1998; Zambaux et al. 1998; Pinto-Alphandry et al., 1995 and U.S. Pat. No. 5,145,684, specifically incorporated herein by reference in its entirety). In particular, methods of antisense oligonucleotide delivery to a target cell using either nanoparticles or nanospheres (Schwab et al., 1994; Truong-Le et al., 1998) are also particularly contemplated to be useful in formulating the disclosed compositions for administration to an animal, and to a human in particular.

4.10.2 Peptide Vectors

The development of an antisense delivery method based on the use of a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., 1997). It was demonstrated in that several molecules of the MPG peptides coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane (Morris et al., 1997).

4.11 Therapeutic Kits Comprising Endo-SR Compositions

In certain embodiments, the inventors contemplate that the methods disclosed herein may be accomplished through the introduction of a pharmaceutical composition comprising an Endo-SR composition into a host cell, and particularly, into an animal such as a mammal either for diagnostic or treatment purposes. As such, one embodiment of the invention concerns the compositions disclosed herein provided in either a therapeutic or diagnostic kit. Such kits typically comprise, in one or more suitable container means, one or more Endo-SR compositions of the present invention in a pharmaceutically acceptable formulation.

The kit may comprise a single container means that contains the Endo-SR composition(s). The container means may, if desired, contain a pharmaceutically acceptable sterile excipient, having associated with it, the Endo-SR composition(s) and, optionally, a detectable label or imaging agent. The formulation may be in the form of a gelatinous composition (e.g., a collagenous composition), a powder, solution, matrix, lyophilized reagent, or any other such suitable means. In certain cases, the container means may itself be a syringe, pipette, or other such like apparatus, from which the composition(s) may be applied to a tissue site, skin lesion, or wound area. However, the single container means may contain a dry, or lyophilized, mixture of one or more Endo-SR composition(s), which may or may not require pre-wetting before use.

Alternatively, the kits of the invention may comprise distinct container means for each component. In such cases, one or more containers would contain each of the Endo-SR composition(s), either as sterile solutions, powders, lyophilized forms, etc., and the other container(s) would include a matrix, solution, or other suitable delivery device for applying or administering the composition to the body, bloodstream, or to a tissue site, skin lesion, wound area, tumor, vasculature or other sites. Such delivery device may or may not itself contain a sterile solution, diluent, gelatinous matrix, carrier or other pharmaceutically-acceptable components.

The kits may also comprise a second or third container means for containing a sterile, pharmaceutically acceptable buffer, diluent or solvent. Such a solution may be required to formulate the Endo-SR composition into a more suitable form for application to the body, e.g., as a topical preparation, or alternatively, in oral, parenteral, or intravenous forms. It should be noted, however, that all components of a kit could be supplied in a dry form (lyophilized), which would allow for "wetting" upon contact with body fluids. Thus, the presence of any type of pharmaceutically acceptable buffer or solvent is not a requirement for the kits of the invention. The kits may also comprise a second or third container means for containing a pharmaceutically acceptable detectable imaging agent or composition.

The container means will generally be a container such as a vial, test tube, flask, bottle, syringe or other container means, into which the components of the kit may placed. The matrix and Endo-SR composition compositions may also be aliquoted into smaller containers, should this be desired. The kits of the present invention may also include a means for containing the individual containers in close confinement for commercial sale, such as, e.g., injection or blow-molded plastic containers into which the desired vials or syringes are retained.

Irrespective of the number of containers, the kits of the invention may also comprise, or be packaged with, an instrument for assisting with the placement of the ultimate matrix-Endo-SR composition within the body of an animal. Such an instrument may be a syringe, pipette, forceps, or any such medically approved delivery vehicle.

4.12 Methods for Generating an Immune Response

Also disclosed in a method of generating an immune response in an animal. The method generally involves administering to an animal a pharmaceutical composition comprising an immunologically effective amount of a composition as disclosed herein, and particularly those which encompass an Endo-SR composition.

The detection of immunocomplex formation is well known in the art and may be achieved through the application of numerous approaches known to the skilled artisan and described in various publications, such as, e.g., Nakamura et al. (1987), incorporated herein by reference. Detection of primary immune complexes is generally based upon the detection of a label or marker, such as a radioactive, fluorescent, biological or enzymatic label, with enzyme tags such as alkaline phosphatase, urease, horseradish peroxidase and glucose oxidase being suitable. The particular antigen employed may itself be linked to a detectable label, wherein one would then simply detect this label, thereby allowing the amount of bound antigen present in the composition to be determined.

Alternatively, the primary immune complexes may be detected by means of a second binding ligand that is linked to a detectable label and that has binding affinity for the first protein or peptide. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labelled secondary antibodies and the remaining bound label is then detected.

The container means will generally include at least one vial, test tube, flask, bottle, syringe or other container means, into which the antigen may be placed, and preferably suitably allocated. Where a second binding ligand is provided, the kit will also generally contain a second vial or other container into which this ligand or antibody may be placed. The kits of the present invention will also typically include a means for containing the vials in close confinement for commercial sale, such as, e.g., injection or blow-molded plastic containers into which the desired vials are retained.

4.13 Peptide Nucleic Acid Compositions

In certain embodiments, the inventors contemplate the use of peptide nucleic acids (PNAs) in the practice of the methods of the invention. PNA is a DNA mimic in which the nucleobases are attached to a pseudopeptide backbone (Good and Nielsen, 1997). PNA is able to be utilized in a number methods that traditionally have used RNA or DNA. Often PNA sequences perform better in techniques than the corresponding RNA or DNA sequences and have utilities that are not inherent to RNA or DNA. An excellent review of PNA including methods of making, characteristics of, and methods of using, is provided by Corey (1997) and is incorporated herein by reference. As such, in certain embodiments, one may prepare PNA sequences that are homologous to, or complementary to one or more portions of the Endo-SR mRNA sequence, and such PNA compositions may be used to regulate, alter, decrease, or reduce the translation of Endo-SR-specific mRNA, and thereby alter the level of Endo-SR activity in a host cell to which such PNA compositions have been administered.

4.13.1 Methods of Making PNAs

PNAs have 2-aminoethyl-glycine linkages replacing the normal phosphodiester backbone of DNA (Nielsen et al., 1991; Hanvey et al., 1992; Hyrup and Nielsen, 1996; Neilsen, 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc (Dueholm et al., 1994) or Fmoc (Thomson et al., 1995) protocols for solid-phase peptide synthesis, although other methods, including a modified Merrifield method, have been used (Christensen et al., 1995).

PNA monomers or ready-made oligomers are commercially available from PerSeptive Biosystems (Framingham, Mass., USA). PNA syntheses by either Boc or Fmoc protocols are straightforward using manual or automated protocols (Norton et al., 1995). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography (Norton et al., 1995) providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (Norton et al., 1995; Haaima et al., 1996; Stetsenko et al., 1996; Petersen et al., 1995; Ulmann et al., 1996; Koch et al., 1995; Orum et al., 1995; Footer et al., 1996; Griffith et al., 1995; Kremsky et al., 1996; Pardridge et al., 1995; Boffa et al., 1995; Landsdorp et al., 1996; Gambacorti-Passerini et al., 1996; Armitage et al., 1997; Seeger et al., 1997; Ruskowski et al., 1997). U.S. Pat. No. 5,700,922 discusses PNA-DNA-PNA chimeric molecules and their uses in diagnostics, modulating protein in organisms, and treatment of conditions susceptible to therapeutics.

4.13.2 Physical Properties of PNAs

In contrast to DNA and RNA, which contain negatively charged linkages, the PNA backbone is neutral. In spite of this dramatic alteration, PNAs recognize complementary DNA and RNA by Watson-Crick pairing (Egholm et al., 1993), validating the initial modeling by Nielsen et al. (1991). PNAs lack 3' to 5' polarity and can bind in either parallel or antiparallel fashion, with the antiparallel mode being preferred (Egholm et al., 1993).

Hybridization of DNA oligonucleotides to DNA and RNA is destabilized by electrostatic repulsion between the negatively charged phosphate backbones of the complementary strands. By contrast, the absence of charge repulsion in PNA-DNA or PNA-RNA duplexes increases the melting temperature ($T_m$) and reduces the dependence of $T_m$ on the concentration of mono- or divalent cations (Nielsen et al., 1991). The enhanced rate and affinity of hybridization are significant because they are responsible for the surprising ability of PNAs to perform strand invasion of complementary sequences within relaxed double-stranded DNA. In addition, the efficient hybridization at inverted repeats suggests that PNAs can recognize secondary structure effectively within double-stranded DNA. Enhanced recognition also occurs with PNAs immobilized on surfaces, and Wang et al. have shown that support-bound PNAs can be used to detect hybridization events (Wang et al., 1996).

One might expect that tight binding of PNAs to complementary sequences would also increase binding to similar (but not identical) sequences, reducing the sequence specificity of PNA recognition. As with DNA hybridization, however, selective recognition can be achieved by balancing oligomer length and incubation temperature. Moreover, selective hybridization of PNAs is encouraged by PNA-DNA hybridization being less tolerant of base mismatches than DNA-DNA hybridization. For example, a single mismatch within a 16 bp PNA-DNA duplex can reduce the $T_m$ by up to 15° C. (Egholm et al., 1993). This high level of discrimination has allowed the development of several PNA-based strategies for the analysis of point mutations (Wang et al., 1996; Carlsson et al., 1996; Thiede et al., 1996; Webb and Hurskainen, 1996; Perry-O'Keefe et al., 1996).

High-affinity binding provides clear advantages for molecular recognition and the development of new applications for PNAs. For example, 11–13 nucleotide PNAs inhibit the activity of telomerase, a ribonucleo-protein that extends telomere ends using an essential RNA template, while the analogous DNA oligomers do not (Norton et al., 1996).

Neutral PNAs are more hydrophobic than analogous DNA oligomers, and this can lead to difficulty solubilizing them at neutral pH, especially if the PNAs have a high purine content or if they have the potential to form secondary structures. Their solubility can be enhanced by attaching one or more positive charges to the PNA termini (Nielsen et al., 1991).

4.13.3 Applications of PNAs

Findings by Allfrey and colleagues suggest that strand invasion will occur spontaneously at sequences within chromosomal DNA (Boffa et al., 1995; Boffa et al., 1996). These studies targeted PNAs to triplet repeats of the nucleotides CAG and used this recognition to purify transcriptionally active DNA (Boffa et al., 1995) and to inhibit transcription (Boffa et al., 1996). This result suggests that if PNAs can be delivered within cells then they will have the potential to be general sequence-specific regulators of gene expression. Studies and reviews concerning the use of PNAs as anti-sense and anti-gene agents include Nielsen et al. (1993b), Hanvey et al. (1992), and Good and Nielsen (1997). Koppelhus et al. (1997) have used PNAs to inhibit HIV-1 inverse transcription, showing that PNAs may be used for antiviral therapies.

Methods of characterizing the antisense binding properties of PNAs are discussed in Rose (1993) and Jensen et al.

(1997). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et al., 1995), isolation of transcriptionally active genes (Boffa et al., 1995), blocking of transcription factor binding (Vickers et al., 1995), genome cleavage (Veselkov et al., 1996), biosensors (Wang et al., 1996), in situ hybridization (Thisted et al., 1996), and in a alternative to Southern blotting (Perry-O'Keefe, 1996).

4.14 Methods of Nucleic Acid Delivery and DNA Transfection

In certain embodiments, it is contemplated that one or more RNA, DNA, PNAs and/or substituted polynucleotide compositions disclosed herein will be used to transfect an appropriate host cell. Technology for introduction of PNAs, RNAs, and DNAs into cells is well-known to those of skill in the art.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Wong and Neumann, 1982; Fromm et al., 1985; Tur-Kaspa et al., 1986; Potter et al., 1984; Suzuki et al., 1998; Vanbever et al., 1998), direct microinjection (Capecchi, 1980; Harland and Weintraub, 1985), DNA-loaded liposomes (Nicolau and Sene, 1982; Fraley et al., 1979; Takura, 1998) and lipofectamine-DNA complexes, cell sonication (Fechheimer et al., 1987), gene bombardment using high velocity microprojectiles (Yang et al., 1990; Klein et al., 1992), and receptor-mediated transfection (Curiel et al., 1991; Wagner et al., 1992; Wu and Wu, 1987; Wu and Wu, 1988). Some of these techniques may be successfully adapted for in vivo or ex vivo use.

Moreover, the use of viral vectors (Lu et al., 1993; Eglitis and Anderson, 1988; Eglitis et al., 1988), including retroviruses, baculoviruses, adenoviruses, adenoassociated viruses, vaccinia viruses, Herpes viruses, and the like are well-known in the art, and are described in detail herein.

4.15 Expression Vectors

The present invention contemplates an expression vector comprising at least one polynucleotide of the present invention. Thus, in one embodiment an expression vector is constructed with a specific DNA molecule orientated in the antisense direction. In another embodiment, a promoter is operatively linked to a sequence region that encodes a functional RNA such as a tRNA, a ribozyme or an antisense RNA. In still other embodiments, a promoter is operatively linked to a sequence region that encodes a functional Endo-SR polypeptide.

As used herein, the term "operatively linked" means that a promoter is connected to a functional DNA, RNA or PNA in such a way that the transcription of that functional DNA, RNA or PNA, is controlled and regulated by that promoter. Means for operatively linking a promoter to a functional DNA, RNA or PNA are well known in the art.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the functional RNA to which it is operatively linked.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

4.16 Transgenic Animals

It is contemplated that in some instances the genome of a transgenic non-human animal of the present invention will have been altered through the stable introduction of one or more of the Endo-SR-encoding, or Endo-SR-specific antisense oligonucleotide compositions described herein, either native, synthetically modified, or mutated. As used herein, the term "transgenic animal" is intended to refer to an animal that has incorporated one or more exogenous selected polynucleotide sequences into its genome. In designing a heterologous gene for expression in animals, sequences which interfere with the efficacy of gene expression, such as polyadenylation signals, polymerase II termination sequences, hairpins, consensus splice sites and the like, are eliminated. Current advances in transgenic approaches and techniques have permitted the manipulation of a variety of animal genomes via gene addition, gene deletion, or gene modifications (Franz et al., 1997). For example, mosquitos (Fallon, 1996), trout (Ono et al., 1997), zebrafish (Caldovic and Hackett, 1995), pigs (Van Cott et al., 1997) and cows (Haskell and Bowen, 1995), are just a few of the many animals being studied by transgenics. The creation of transgenic animals that express human proteins such as $\alpha$-1-antitrypsin, in sheep (Carver et al., 1993); decay accelerating factor, in pigs (Cozzi et al., 1997); and plasminogen activator, in goats (Ebert et al., 1991) have previously been demonstrated. The transgenic synthesis of human hemoglobin (U.S. Pat. No. 5,602,306) and fibrinogen (U.S. Pat. No. 5,639,940) in non-human animals have also been disclosed, each specifically incorporated herein by reference in its entirety. Further, transgenic mice and rat models have recently been described as new directions to study and treat cardiovascular diseases such as hypertension in humans (Franz et al., 1997; Pinto-Siestma and Paul, 1997). The construction of a transgenic mouse model has recently been used to assay potential treatments for Alzheimer's disease (U.S. Pat. No. 5,720,936, specifically incorporated herein by reference in its entirety). It is contemplated in the present invention that transgenic animals contribute valuable information as models for studying the effects of Endo-SR-specific AS-ODN compositions, and the activity and regulation of Endo-SR in vivo.

4.17 DNA Integration, RNA Expression and Inheritance

Genomic DNA may be isolated from animal cell lines or any animal parts to determine the presence of the exogenous gene through the use of techniques well known to those skilled in the art. Note, that intact sequences will not always be present, presumably due to rearrangement or deletion of sequences in the cell.

The presence of DNA elements introduced through the methods of this invention may be determined by polymerase chain reaction (PCR™). Using this technique discreet fragments of DNA are amplified and detected by gel electrophoresis. This type of analysis permits one to determine whether a gene is present in a stable transforrnant, but does not prove integration of the introduced gene into the host cell genome. It is the experience of the inventors, however, that DNA has been integrated into the genome of all transformants that demonstrate the presence of the gene through PCR™ analysis (Wu et al., 1998). In addition, it is not possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™ e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Whereas DNA analysis techniques may be conducted using DNA isolated from any part of an animal., RNA will only be expressed in particular cells or tissue types and hence it will be necessary to prepare RNA for analysis from these tissues. PCR™ techniques may also be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

4.18 Vector Backbone

Throughout this application, the term "expression construct" is meant to include any type of genetic construct containing a nucleic acid comprising a sequence that encodes Endo-SR polypeptide, or an antisense sequence that is capable of interacting with the mRNA of Endo-SR and affecting its expression, and/or translation into mature Endo-SR polypeptide.

In certain embodiments, when the polynucleotide construct is placed under the control of a promoter for expression in a transformed host cell, the presence of one or more enhancer elements may be desirable in the vector constructs that comprise the Endo-SR-specific oligonucleotide sequence.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

In one embodiment, the expression construct of the present invention may be comprised within a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Temin, 1986). The first viruses used as gene vectors were DNA viruses including the papovaviruses (simian virus 40, bovine papilloma virus, and polyoma) (Ridgeway, 1988) and adenoviruses (Ridgeway, 1988). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Characterization of an Endonuclease Activity which Preferentially Cleaves the G-Rich Immunoglobulin Switch Repeat Sequences This example describes the characterization of a novel endonuclease activity, Endo-SR, which is a likely candidate for the nuclease activity required for isotype switch recombination.

5.1.1 Materials and Methods
5.1.1.1 Cells and Culture Conditions

The murine 38B9 pre-B cell line (Alt et al., 1981), was grown in RPMI 1640 media supplemented with 10% newborn calf serum, 10 mM HEPES, 10 mM β-mercaptoethanol, 50 µg/ml penicillin, and 130 µg/ml streptomycin. Cells were maintained at greater than 90% viability and grown to an average density of $5\times10^6$ cells/ml in 8 l spinner flasks. After reaching a maximum viable concentration, cells were spun down at 1,500×g (4° C.), washed twice in ice cold PBS, and frozen in liquid nitrogen prior to long-term storage at −70° C.

5.1.1.2 Nuclear Extract Preparation

Nuclear extracts were prepared by a modification (Aguilera et al., 1987) of the procedure as described (Dignam et al., 1983). Frozen cell pellets (~$1\times10^{11}$ cells) were resuspended in Buffer A (10 mM HEPES (pH 7.9), 1.5 mM $MgCl_2$, 10 mM KCl, 0.5 mM PMSF, and 0.2% sucrose), incubated on ice for 10 min, and then dounced with a B-type glass pestle until cells were clearly lysed when examined by microscopy. Cell lysates were centrifuged for 10 min at 1500 g (4° C.) to selectively pellet nuclei from other cellular debris. Nuclei were resuspended in Buffer A, recentrifuged to reduce cytoplasmic protein contamination, and then resuspended in two volumes of Buffer B (20 mM HEPES (pH 7.9), 25% glycerol, 420 mM NaCl, 1.5 mM $MgCl_2$, 0.2 mM EDTA, 0.5 mM PMSF, 0.5 mM DTT, 1 µg/ml antipain and pepstatin, and 0.3 µg/ml leupeptin). Resuspended nuclei were homogenized with a type-A glass pestle then incubated on ice for 30 min with constant stirring. Nuclei were subsequently removed by centrifugation at 10,000 g for 30 min at 4° C. and the nuclear extracts were stored at −70° C.

5.1.1.3 Endonucleolytic Assay and DNA Substrates

Endonuclease assays were conducted in 10 µl reaction volumes containing 10 mM bis-Tris (pH6.5), 5 mM $MgCl_2$, ~250 pmoles of an end-labeled ($^{32}P$) DNA substrate, 1 µg of calf-thymus DNA, and 1 µl of an active Endo-SR fraction. Lower pH buffers (pH 4.5–5.5) were subsequently demonstrated to enhance cleavage activity. Futhermore, MgCl was removed from these assays as it was shown to interfere with the cleavage assay (Lyong and Aguilera, 1997). All nuclease assays were performed with Fraction IV enzyme (see below) as the source for Endo-SR activity, unless otherwise specified. Nuclease assays performed for biochemical analysis of Endo-SR activity were conducted as described except for the addition or substitution of the test material. Reactions were incubated at 37° C. for 30 min, then mixed with an equal volume of formamide dye (Ausubel et al., 1987) and heated to 95° C. for 5 min prior to electrophoresis on an appropriate percentage (8–15%) sequencing gel. After electrophoresis, these gels were transferred to Whatman paper, dried, and exposed to film for 12–48 h. All detected cleavage products were compared to adjacent Maxam-Gilbert sequencing reactions, and adjusted one nucleotide 3' to compensate for the removed base (Ausubel et al., 1987). After autoradiographic analysis, endonuclease activity was assayed by scintillation counting of intact substrate and specific cleavage products excised from the dried gel. End-labeled DNA substrates were prepared according to previously described methods (Hope et al., 1986).

A series of end-labeled DNA substrates were prepared from Sµ, Sα, and plasmid DNA: a 253 bp SacI-MspI murine Sµ fragment derived from a 1 kb HindIII clone (Aguilera et al., 1985; Sakano et al., 1980), a 1.7 kb SacI-PstI fragment (Sα-1) and a ~625 bp XbaI-PstI fragment (Sα-2) derived from a full-length murine Sα clone (Aguilera et al., 1985), and a 2.5 kb NdeI-EcoR I fragment derived from pUC18 plasmid DNA.

A series of oligonucleotides were synthesized, annealed, and subcloned into pUC18 as substrates for the characterization of sense and antisense Endo-SR cleavages within Sµ consensus sequence. The oligonucleotides used are as follows:

SµO-5R1 (5'-CTAGAGCTGGGGTGAGCTGAGCTGAGCT-3' (SEQ ID NO:5)/5'-CTAGAGCTCAGCTCAGCTCACCCCAGCT-3') (SEQ ID NO:6); and SµO-5R2 (5'-CTAGAGCTGAGCTGAGCTGAGCTGAGCT-3' (SEQ ID NO:7)/5'-CTAGAGCTCAGCTCAGCTCAGCTCAGCT-3') (SEQ ID NO:8).

The oligonucleotides were synthesized with XbaI cohesive ends, annealed, and ligated into the XbaI site of pUC18. SµO-2R (5'-TGGGGTGAGCTGCA-3' (SEQ ID NO:9) and 5'-GCTCACCCCAGTAC-3') (SEQ ID NO:10) oligonucleotides were made with KpnI and PstI cohesive ends, annealed, and ligated into the KpnI-PstI sites of pUC18.

5.1.1.4 Protein Purification and Detection

Crude 38B9 nuclear extracts (Fraction I, 420 mM NaCl) were diluted to 200 mM NaCl with Buffer C (20 mM HEPES (pH 7.9), 0.5 mM PMSF, and 10% glycerol) and fractionated on a heparin-agarose column (25 ml bed volume, BioRad). Approximately 50% of nuclear protein, and greater than 95% of detected Endo-SR activity, flowed through this column. This material (Fraction II) was dialyzed extensively against Buffer D (10 mM bis-Tris (pH 6.5), 200 mM NaCl, 0.5 mM PMSF, and 10% glycerol), and subsequently fractionated on an Affi-gel Blue dye affinity column (15 ml bed volume, BioRad) with 200, 500, 1000 mM NaCl elution steps. All detectable enzyme activity eluted in 500 mM NaCl (Fraction III).

After dilution to 100 mM NaCl with Buffer D (0 mM NaCl), Fraction III material was fractionated on a BioRex 70 weak cation exchange column (15 ml bed volume, BioRad), with stepped 100, 300, 1000 mM NaCi elutions. Fraction IV, the 300 mM NaCl step, contained all detectable Endo-SR activity. Fraction IV was diluted to 100 mM NaCl with Buffer D (0 mM NaCl) and fractionated on a Mono S strong cation exchange column (1 ml bed volume, Pharmacia) with a 100–400 mM NaCl linear salt gradient. All detectable Endo-SR activity eluted in two sequential 0.5 ml fractions (Fraction V) at ~235 mM NaCl. Aliquots from each purification fraction were assayed for Endo-SR activity as described above, and protein concentrations were determined by the Micro BCA protein assay (Pierce).

An aliquot of each fraction was also denatured under reducing conditions and size-fractionated on a 20% SDS-polyacrylamide gel (30:1 acrylamide:bis-acrylamide; (Ausubel et al., 1987) and stained with commercial silver stain reagents (Gelcode™, Pierce). The native molecular mass of Endo-SR (Fraction IV) was determined by size exclusion chromatography on a prepacked Superose 12 HR 10/30 column (Pharmacia) equilibrated against Buffer E (10 mM Tris (pH 7.0), 100 mM NaCl, 1 mM DTT, 0.1% NP-40, 10% glycerol) and calibrated with a set of commercial gel filtration protein standards (Bio-Rad).

Endo-SR activity values (fmol/min) were determined by quantitation of the radioactivity present in specific nuclease cleavage products and intact substrate (negative control) excised from the dried gel (Lyon et al. 1996). Nuclease activity determined for a pure bovine Endo-SR fraction demonstrated that 1 µg of this material could generate >100 picomoles of specific cleavages/ minute. In this analysis, the amount of enzyme required to generate 1 fmol of cuts/min within the assayed substrate was defined as one unit of Endo-SR (Lyon et al. 1997).

5.1.2. Results

5.1.2.1 Endonucleolytic Cleavage of S Region DNA Substrates

A potential switch endonuclease activity was first detected during the purification of a putative switch DNA binding protein from nuclei of a murine pre-B cell line (Miranda et al., 1995). Murine switch region DNA substrates incubated with this nuclear extract were reproducibly cleaved at internal sites, and strong cleavages were primarily localized to G-rich S motifs. However, accurate characterization of the responsible enzyme, Endo-SR, was severely hampered due to the presence of high levels of contaminating exonucleases in crude nuclear extracts. In order to better characterize this nuclease activity, all subsequent analyses were performed with partially purified Endo-SR activity (Fraction IV, see below) which contained no detectable exonuclease activity.

Partially purified Endo-SR activity generated strong, reproducible cleavages on several germline S region DNA substrates, and differential cleavages were detected at the variable S pentamer repeats in each analyzed S region DNA substrate. A series of germline $S\mu$ repeats were cleaved in a reproducible, repetitive pattern. Strong double cleavages were detected at each TGGGG motif, and fainter single cleavages were detected at each TGAGC motif. These cleavages occurred at precise sites within each motif: after the first nucleotide in TGAGC motifs, and after the first and second nucleotides in TGGGG motifs. Endo-SR activity thus generated a highly distinctive $S\mu$ cleavage pattern in which a cleavage site was detected at every fifth nucleotide with an additional, adjacent cleavage at every TGGGG motif.

Nuclease assays performed with a germline Sα substrate (Sα-1) detected cleavages which superficially resembled those determined for the $S\mu$ DNA substrate. Strong multiple cleavage sites were again primarily localized to G-rich pentamer motifs, but cleavage sites varied dramatically among themselves and with sites determined for the $S\mu$ substrate. Strong multiple cleavages were detected at single (TGGGC and TGGGA) and double (TAGGA) nucleotide variants of the consensus $S\mu$ TGGGG motif.

Double cleavages detected within TGGGC and TAGGA motifs occurred at the same positions as cleavages detected within consensus $S\mu$ TGGGG motifs. Strong multiple cleavages detected at two TGGGA motifs diverged from this consensus double cleavage pattern. Each of these two identical TGGGA motifs was selectively cleaved to produce a unique double or triple cleavage site. Single cleavage sites also revealed a greater sequence variability than demonstrated within the $S\mu$ DNA substrate, and were detected even at highly degenerate "TGAGC" motifs upon prolonged exposure. All detected single cleavage sites occurred after the first nucleotide in a targeted pentamer motif and matched the consensus single cleavage site detected at $S\mu$ TGAGC motifs. Nuclease activity at these motifs did, however, demonstrate significant differences in cleavage strength, and selective cleavages were detected even at identical "TGAGC" motifs (TGAGC, TAGGC).

Additional sequence context adjacent to the cleaved pentamer motif appears to be the most likely explanation for differential or selective cleavage of otherwise identical pentamer motifs, and nuclease assays performed with a second germline Sα substrate (Sα-2) appear to support this contention. Nuclease assays performed with the Sα-2 substrate revealed a repetitive cleavage pattern in which the strongest cleavages were found within a perfect hexad direct repeat of TGGGA pentamers. Strong single cleavages were detected at each TGGGA motif within this direct repeat, and cleavage strength appeared to increase at each successive site within the repeat. Much weaker single and double cleavage sites were detected within adjacent DNA sequence. Single cleavages within direct repeat TGGGA motifs also appear to demonstrate a marked increase in cleavage strength and precision relative to similar cleavages detected with the Sα-1 DNA substrate.

In contrast, nuclease assays performed with a pUC18 DNA substrate revealed only sporadic weak cleavages at degenerate pentamer motifs or cryptic sites. Nuclease assays performed with other regions of pUC18 DNA revealed similar sporadic cleavages primarily at G-rich sequences. No double cleavages were detected in any of the pUC18 substrates assayed, in contrast to strong double cleavages detected within S region DNA substrates. Cleavage sites often demonstrated complete or partial homology to S pentamer motifs, although cleavages at these altered motifs often did not match consensus cleavage positions. Among the cleavages observed, for example, a degenerate TGGAA motif was cleaved at the consensus site, while a canonical TGAGC motif was cleaved at an aberrant site adjacent to this motif. Additional weak cleavages were detected at cryptic sequence motifs with no apparent homology to previously observed S region cleavage sites. Although these nuclease assays were performed with highly purified enzyme activity (Fraction IV; see Table 4), it is possible that some of the observed cleavages could be produced by minor nuclease contaminants in the purified fractions. However, nuclease assays performed under alternate assay conditions have not demonstrated selective enhancement of a subset of cleavages, as might be expected for discrete enzyme activities.

As shown above, Endo-SR activity detected within the analyzed S region DNA substrates appears to be consistent with a putative switch endonuclease activity. Endo-SR recognizes sites composed of the two common S pentamer motifs, cleavage affinity and specificity are apparently influenced by sequence context, and S region DNA is preferentially cleaved. Endonucleolytic cleavages generated by a putative switch endonuclease should also produce double-stranded breaks within S region DNA. However, due to the repetitive nature and large size of the analyzed germline S DNA substrates, accurate Endo-SR cleavage sites could not be determined for the appropriate complementary strand regions.

TABLE 4

PURIFICATION OF ENDO-SR FROM 38B9 PRE-B CELL NUCLEAR EXTRACTS

| | Protein (µg) | Activity (units) | Specific Activity (units/µg) | Purification | Yield (%) |
|---|---|---|---|---|---|
| I. Nuclear Extract | $25.2 \times 10^3$ | $9.1 \times 10^{6*}$ | $3.6 \times 10^2$ | 1 | — |
| II. Herapin | $12.4 \times 10^3$ | $4.2 \times 10^{7*}$ | $3.4 \times 10^3$ | 9.4 | — |
| III. Affi-Gel Blue | $1.25 \times 10^3$ | $5.4 \times 10^7$ | $4.3 \times 10^4$ | 120 | 100** |

TABLE 4-continued

PURIFICATION OF ENDO-SR FROM 38B9 PRE-B CELL NUCLEAR EXTRACTS

|   | Protein (µg) | Activity (units) | Specific Activity (units/µg) | Purification | Yield (%) |
|---|---|---|---|---|---|
| IV. BioRex 70 | $2.4 \times 10^2$ | $1.6 \times 10^7$ | $6.7 \times 10^4$ | 190 | 29 |
| V. MonoS | 3.5 | $8.4 \times 10^5$ | $2.4 \times 10^5$ | 670 | 2*** |

*Underestimated due to degradation of Endo-SR cleavage products by contaminating nuclease activities.
**Assigned 100% yield, since removal of additional nucleaes activities resulted in a >100% yield by this step.
***Substantial activity losses during this purification resulted in a poor purification by specific activity.

5.1.2.2 Endonucleolytic Cleavage of S Repeat Oligonucleotide Substrates

A series of oligonucleotide substrates were synthesized to address the double strand cleavage specificity of this enzyme. Nuclease assays performed with the SµO-5R1 oligonucleotide substrate, which contains a consensus Sµ repeat structure (TGGGGTGAGCTGAGCTGAGC) (SEQ ID NO:11), revealed a cleavage pattern virtually identical to that observed with germline Sµ DNA. In this assay, a strong double cleavage site was detected at the TGGGG motif, and single weaker cleavages were observed at all TGAGC motifs. The double cleavage site and those cleavage sites directly flanking it precisely matched corresponding germline Sµ DNA cleavage sites. Single cleavages at SµO-5R1 TGAGC motifs also precisely matched germline cleavages down to a faint secondary cleavage trailing the "standard" TGAGC single cleavage site. Analysis of the antisense strand of the SµO-5R1 substrate revealed a single strong cleavage site opposite the sense strand TGGGG motif. No other cleavages were detected on this strand. Alignment of the SµO-5R1 sense and antisense strand cleavage sites revealed a potential double strand cleavage within the TGGGG motif, which should produce blunt ended and/or 3' nucleotide overhanging DNA fragments.

Nuclease assays performed with the SµO-5R2 oligonucleotide substrate, which contained an altered Sµ repeat structure (TGAGCTGAGCTGAGCTGAGC) (SEQ ID NO:12), revealed a significantly different cleavage pattern. Replacement of the consensus Sµ TGGGG motif by a TGAGC motif abolished the strong double cleavage previously detected at this site. Standard single cleavage sites were detected at every TGAGC motif within this substrate, consistent with those detected at germline TGAGC motifs. No antisense strand cleavages were detected within SµO-5R2 DNA.

Nuclease assays performed with germline and oligonucleotide Sµ DNA substrates have shown that Endo-SR recognizes and cleaves at least two different sequences with different affinity and cleavage specificity. Additionally, as described above, these differential cleavage activities appear to correlate with single- or double-stranded DNA cleavages. Endo-SR recognizes and avidly cleaves a TGGGG motif within the consensus Sµ repeat structure to produce double stranded breaks. Endo-SR also recognizes and cleaves TGAGC motifs within Sµ sequence to produce single-stranded nicks. Although strong double-stranded Sµ DNA cleavages appear to require a TGGGG motif, this sequence alone may not be sufficient to specify these cleavages.

In order to further characterize the sequence specificity of Endo-SR, a double-stranded oligonucleotide containing a single copy of each of the Sµ repeats (SµO-2R) was also synthesized and tested with partially purified Endo-SR. This truncated Sµ substrate was found to be cleaved at the same sites as previous germline and synthetic Sµ substrates. An intense double cleavage site was readily detected within the TGGGG pentamer motif, and a faint single cleavage site was detected within the downstream TGAGC motif upon prolonged exposure. Both cleavage sites precisely matched previously determined S pentamer cleavage sites. A cleavage site on the antisense strand also matched the previously detected Sµ antisense strand cleavage site, although a series of progressively fainter cleavages trailed this site. Additional DNA sequence not contained in this substrate thus appears necessary to specify the precise antisense strand single cleavage site detected with the SµO-5R1 oligonucleotide. A new antisense strand cleavage detected with this substrate may reveal sporadic enzyme activity or a cryptic recognition site caused by adjacent polylinker sequence.

5.1.2.3 Tissue Specificity of Endo-SR Activity

An endonuclease activity involved in switch recombination should be highly restricted in its expression, since switch recombination is a cell-specific process restricted to mature B-lymphocytes. In order to address this requirement, nuclear extracts were prepared from a series of murine organs, partially purified to remove contaminating nucleases, and analyzed for Endo-SR activity. Among the extracts tested only spleen and thymus contained detectable activity, as consistent with a lymphoid-specific Endo-SR expression pattern. Brain and liver extracts were subsequently shown to contain lower but detectable levels of Endo-SR activity (Lyon and Aguilera, 1997).

5.1.2.4 Purification of the Endo-SR Nuclease

In order to accurately characterize the Endo-SR activity, the inventors have attempted to purify this activity to homogeneity by column chromatography. As previously mentioned, this activity was first detected in murine 38B9 pre-B cell crude nuclear extracts during the purification of a DNA binding protein with strong affinity for G-rich S pentamer motifs (Miranda et al., 1995). Accordingly, this material was chosen as the source material for a purification of the observed endonuclease activity. Nuclei were isolated from large-scale cultures of this cell line and extracted with a stepped increase in NaCl concentration. Nuclear extracts (Fraction I) obtained at 420 mM NaCl contained the vast majority of detectable Endo-SR activity. Unfortunately, Fraction I enzyme contained high levels of contaminating nucleases which partially masked the specific endonuclease activity. At this stage, specific S region cleavage sites could be detected only by addition of high concentrations of non-specific competitor DNA. After fractionation on a heparin-agarose column, the Endo-SR enriched fractions (Fraction II) demonstrated a significant reduction in contaminating nuclease activity, and dramatic increases in specific and total enzyme activity (Table 2). Endo-SR specific activity increased more than nine-fold during this purification, while total enzyme activity increased nearly five-fold. Fractionation on an Affi-Gel Blue dye affinity column generated Endo-SR fractions (Fraction III) essentially devoid of contaminating exonuclease activity. This material displayed an approximate twelve-fold increase over Fraction II Endo-SR specific activity.

Fraction III also displayed the most Endo-SR activity of any purification step, and was thus designated the source fraction for calculation of enzymatic yield (Table 2).

Subsequent fractionation on a BioRex 70 weak cation exchange column produced enzyme (Fraction IV) which displayed only a moderate (~56%) increase in specific activity despite a greater than five-fold protein purification. Endo-SR fractionation on a Mono S strong cation exchange column also demonstrated dramatic differences between protein and enzyme purification yields. All Endo-SR activity eluted in two sequential fractions (Fraction V) from this column. Although this step resulted in an approximate seventy-fold purification by protein yield, this step resulted in only a three-fold enzyme purification by enzymatic activity. No further purification of Fraction V was attempted due to the rapid loss of activity on the final two purification columns.

Activity losses during column chromatography dramatically affected enzymatic purification. After the final column, a greater than 7000-fold protein purification had resulted in less than a 700-fold enzymatic purification. Activity losses during this process accounted for almost 98% of detected Endo-SR activity. Additional activity losses were detected during short term storage of Fraction V. Rapid Endo-SR inactivation in the final stages of this purification could be caused by a number of factors: instability in dilute protein solutions, removal of a stabilizing protein or cofactor, or copurification with an active protease. Concentration of active fractions had no apparent effect upon enzyme instability, however, and the enzyme retained greater than 96% activity after four h at 37° C. Thus, it does not appear that a dilution effect or a protease contaminant are responsible for Endo-SR instability in purified fractions.

Analysis of Fractions II–V by SDS-PAGE revealed an enrichment of a 20 kDa protein in Fractions IV and V, which correlated well with a 20–25 kDa size range previously determined for Endo-SR activity by native size exclusion chromatography. An 18 kDa protein was also detected in Fractions IV and V, although peak Endo-SR activity did not correlate with the relative abundance of this protein, and gradient fractions selectively enriched for the 18 kDa, but not the 20 kDa, protein revealed no detectable activity. Mixture of selectively enriched 18 and 20 kDa fractions did not result in significant enhancement or suppression of Endo-SR activity. Accordingly, the inventors believe that the detected 20 kDa protein is the Endo-SR protein. It is possible that the detected protein was a processed version of the ~40 kDa Endo-SR protein or a contaminant of this preparation.

Analysis of Fractions I–V in standard nuclease assays revealed a conservation of detected cleavages throughout the purification process. Nuclease assays were performed with diluted enzyme fractions in order to normalize Endo-SR activity across the assayed samples. Early samples (Fractions I–III) contained roughly equivalent amounts of enzymatic activity upon assay, but Fractions IV and V demonstrated substantially reduced enzyme activities. Reduced Endo-SR activity in these fractions appeared to result from progressive activity losses in these fractions, since attempts to repeat these assays with adjusted activity values yielded similar results. A strong double cleavage site (double arrows) was readily detectable in all samples while a fainter single cleavage (arrow) was greatly diminished in Fractions IV and V (clearly detectable upon over exposure). Reduction of this cleavage correlated with a progressive loss of activity in these fractions and did not appear to result from reduction of a separate enzymatic activity. A weak exonucleolytic activity which leads to the production of multiple cleavages below the major cleavages was observed in the early steps in the purification process (Fractions I–III).

5.1.2.5 Biochemical Characterization of Endo-SR Activity

In order to distinguish the detected Endo-SR activity from previously characterized endonucleases common nuclease parameters were analyzed to determine optimal conditions for enzyme activity. As the initial step in this process, the pH optimum was determined for partially purified Endo-SR activity. As shown in FIG. 3A, this enzyme demonstrated maximal specific activity in a narrow pH range. Maximal activity was detected at pH 5.5, and decreased ~50% within ±0.5 pH units. Beyond this range, however, activity losses were dramatic and asymmetric. At two pH units below its optimum pH Endo-SR still retained ~9% activity, while at two pH units above its optimum pH only ~1% activity remained.

Most previously reported mammalian endonuclease activities demonstrate a requirement for $Mg^{2+}$ as either the sole required cation (McKenna et al., 1981; Low et al., 1987; Kataoka et al., 1984; Cote et al., 1989; Gottlieb and Muzyczka, 1990; Hibino et al., 1988; Wang et al., 1978; Wang and Furth, 1977; Fischman et al., 1979; Tomkinson and Linn, 1986) or as a synergistic partner with $Ca^{2+}$ (Hibino et al., 1989; Hashida et al., 1982; Yoshihara et al., 1982; Stratling et al., 1984; Gaido and Cidlowski, 1991; Montague et al., 1994; Ribeiro and Carson, 1993; Yashihara et al., 1974; Ishida et al., 1974; Hewish and Burgoyne, 1973; Nakamura et al., 1981). Analysis of Endo-SR activity revealed this enzyme was active in the absence of added $M^{2+}$. However, Endo-SR activity detected in these assays appeared to require a $M^{2+}$ cofactor, since addition of $Mg^{2+}$ or $Ca^{2+}$ significantly enhanced enzyme activity while addition of EDTA strongly inhibited this activity (FIG. 3B). As shown in FIG. 3B, Endo-SR activity in the presence of 500 μM $Mg^{2+}$ or $Ca^{2+}$, but not $Mn^{2+}$, was significantly enhanced. Assays performed with 50 μM concentrations of these $M^{2+}$ species showed no significant differences from unsupplemented assays, and higher cation concentrations were inhibitory. Furthermore, assays performed with both $Ca^{2+}$ and $Mg^{2+}$ did not demonstrate synergistic activation. However, addition of $Zn^{2+}$ to a concentration of 50 μM resulted in ~50% inhibition, and ~95% inhibition was observed at a 500 μM concentration. As mentioned earlier, addition of EDTA also inhibited Endo-SR activity, such that ~40% inhibition was observed with 5 mM EDTA, while 50 mM EDTA completely inhibited all detectable enzyme activity.

5.1.3 Discussion

Although the proteins directly involved in switch recombination have not yet been identified, it appears likely that a multi-subunit protein complex is required to mediate this process. A putative switch recombinase complex must specifically recognize, cleave, and rejoin targeted S DNA substrates during the course of a normal rearrangement event. Recently, several potential candidates for the DNA binding component(s) of such a switch recombinase complex have been described (Waters et al., 1989; Wuerffel et al., 1990; Xu et al., 1992; Marcu et al., 1992; Fukita et al., 1993; Mizuta et al., 1993; Miranda et al., 1995).

A potential switch endonuclease (Endo-SR) activity was first detected in pre-B cell crude nuclear extracts during the purification of a putative switch DNA binding protein (Miranda et al., 1995). Nuclease activity isolated from these extracts readily cleaved all analyzed S DNA substrates. Nuclease assays performed with germline Sµ DNA revealed a repetitive cleavage pattern in which strong double cleavages were detected at TGGGG motifs and weaker single cleavages were detected at TGAGC motifs. Subsequent nuclease assays performed with Sµ oligonucleotide substrates revealed that both full-length (SµO5R1) and truncated (SµO2R) Sµ repeat structures were cleaved in a manner virtually identical to Sµ germline DNA. Nuclease assays performed with a third oligonucleotide substrate, containing an altered Sµ repeat structure, demonstrated that both Sµ pentamer motifs were required to generate the cleavages detected within germline Sµ DNA.

Nuclease assays performed with Sα germline DNA revealed a more degenerate cleavage pattern than observed for analyzed Sµ DNA substrates. Analogous to cleavages observed with Sµ DNA substrates, strong multiple cleavages were primarily localized to "degenerate" TGGGG motifs, while weak single cleavages were detected at "degenerate" TGAGC motifs. However, cleavages detected at identical Sα motifs sometimes demonstrated different cleavage affinities or altered positions. Strict cleavage patterns determined for the consensus S motifs were found only when the motifs shared common flanking sequences.

Nuclease assays conducted with Sµ and Sα DNA substrates have thus demonstrated that Endo-SR activity recognizes and cleaves consensus and degenerate switch motifs, and that adjacent DNA sequence influences recognition and/or cleavage at these sites. Endo-SR activity, however, is not restricted to S region DNA. Nuclease assays performed with an unrelated DNA substrate (pUC18) have also detected sporadic weak cleavage of this DNA. Nuclease cleavage sites primarily map to "degenerate" pentamer motifs found within this DNA, although rare cleavages have been detected at cryptic sites which bear no apparent resemblance to S pentamer sequences. Nuclease activity detected within this non-switch DNA substrate indicates a potential for Endo-SR-mediated cleavages outside switch region DNA.

Nuclease assays performed with Sµ oligonucleotide substrates, however, have demonstrated that double-strand cleavages do not occur at every Sµ sense-strand cleavage site. Antisense strand cleavages were only detected opposite the sense strand TGGGG motif, and replacement of this motif was shown to abolish all antisense strand cleavages.

Adjacent sequence also appeared to influence antisense strand cleavages, since assay of an abbreviated Sµ repeat structure (SµO-2R) detected an additional antisense cleavage site and diminished precision at the previously detected site.

Analysis of Endo-SR cleavages has revealed a correlation among cleavage strength and character (single- vs double-stranded). Strong cleavage sites at "TGGGG" motifs primarily result in double-stranded DNA breaks, while weak cleavage sites at "TGAGC" motifs appear to result exclusively in single-stranded DNA nicks. However, these two motifs differ at only two positions, and Endo-SR cleavages at degenerate motifs of each type demonstrates that strict adherence to a TGGGG or TGAGC consensus sequence is not required for precise cleavage. As discussed previously, adjacent sequence also appears to influence Endo-SR cleavage of these motifs. Thus, it seems likely that Endo-SR recognizes a single degenerate recognition sequence which overlaps multiple S motifs, and that cleavage strength, character, and precision at a particular site is highly sensitive to the sequence at that site.

Most previously reported mammalian endonucleases require $Mg^{2+}$ alone (McKenna et al., 1981; Low et al., 1987; Kataoka et al., 1984; Cote et al., 1989; Gottlieb and Muzyczka, 1990; Hibino et al., 1988; Wang et al., 1978; Wang and Furth, 1977; Fischman et al., 1979; Tomkinson and Linn, 1986) or in combination with $Ca^{2+}$ for activity (Hibino et al., 1989; Hashida et al., 1982; Yoshihara et al., 1982; Stratling et al., 1984; Gaido and Cidlowski, 1991; Montague et al., 1994; Ribeiro and Carson, 1993; Yashihara et al., 1974; Ishida et al., 1974; Hewish and Burgoyne, 1973; Nakamura et al., 1981; Shiokawa et al., 1994). Nucleases of the latter group demonstrate a strict $Ca^{2+}$ requirement, and require relatively high $Ca^{2+}$ (1 mM) and $Mg^{2+}$ (1–5 mM) concentrations for optimal enzyme activity (Stratling et al., 1984; Shiokawa et al., 1994). In contrast, Endo-SR retained activity in the absence of added $Ca^{2+}$ or $Mg^{2+}$, but exhibited maximal activity when supplemented with 500 µM $Mg^{2+}$ (FIG. 3B). Nuclease assays supplemented with both $Ca^{2+}$ and $Mg^{2+}$ demonstrated no additional increase in Endo-SR activity. Thus, Endo-SR activity does not conform to previously characterized $Ca^{2+}/Mg^{2+}$-dependent endonuclease activities. However, Endo-SR activity appears to require a $M^{2+}$ cofactor, since addition of EDTA to $\geq$50 mM resulted in complete inhibition of Endo-SR activity (FIG. 3B). Endo-SR thus appears to represent a novel $Mg^{2+}$-dependent endonuclease, since comparison with previously reported $Mg^{2+}$-dependent nucleases have demonstrated significant differences.

All other $Mg^{2+}$-dependent endonucleases examined demonstrated $Ca^{2+}$ inhibition (McKenna et al., 1981; Gottlieb and Muzyczka, 1990; Hibino et al., 1988; Wang et al., 1978; Fischman et al., 1979; Tomkinson and Linn, 1986), or different sequence (Kataoka et al., 1984; Cote et al., 1989; Gottlieb and Muzyczka, 1990; Wang and Furth, 1977) and/or tissues specificities (Cummings et al., 1987; Kataoka et al., 1984; Hibino et al., 1988; Tomkinson and Linn, 1986) than determined for Endo-SR activity. The endonuclease activity reported in this study therefore appears to represent the newly detected activity of a novel endonuclease, rather than an undescribed activity of a previously reported enzyme.

Characterized sequence- and tissue-specificity strongly suggest that this enzyme activity may play a central role in switch recombination events. Although lymphoid-restricted expression of Endo-SR activity supports a potential role for Endo-SR activity in a lymphoid-specific DNA rearrangement or repair pathway, a putative switch endonuclease activity should theoretically be restricted to differentiating B cells.

Prior to activation of a switch recombination pathway, most S region DNA is probably protected from nuclease attack by nucleosomal protein complexes or other specific DNA binding proteins. Several reports have shown that activation of switch recombination results in decondensation of local chromatin structure (Berton and Vitetta, 1990) and transcriptional activation of a particular S region in response to lymphokine- and contact-mediated stimuli (Goodman et al., 1993; Gaff et al., 1992). Activation of switch recombination may therefore result from increased accessibility of an endogenous switch endonuclease activity and other "switch" factors to a newly activated S region. A different mechanism, however, must protect exposed S region DNA before and after switch recombination to prevent the rapid destruction of these sequences.

As mentioned previously, switch nuclease/recombinase activity must be strictly regulated in lymphoid tissues due to the potential for premature and/or deleterious rearrangements within S$\mu$, within fused S regions, or with cryptic recognition sites outside the IgH gene locus. Several common lymphoid DNA rearrangements are suggestive of aberrant switch recombinase activity. Activation of resting B lymphocytes with LPS, for example, has been shown to cause internal S$\mu$ rearrangements (Wuerffel et al., 1990; Kenter and Watson, 1987). Furthermore, S$\mu$ DNA has been shown to participate in chromosomal translocations with the myc gene locus, and several translocation breakpoints within myc resemble G-rich S motifs (Aguilera et al., 1985; Gerondakis et al., 1984; Bernard et al., 1983). Analysis of several non homologous recombination breakpoints has also recently detected a CTGG tetramer motif at or near translocation breakpoints at switch regions, $V_H$ replacements, and other illegitimate recombination events involving the Ig loci (Chou and Morrison, 1993). This motif can also be found within the canonical mammalian $\chi$-like recombination hotspot (CC[T/A]GG[T/A]GC) detected at the bcl-2 gene breakpoint region (Wyatt et al., 1992; Krowczynska et al., 1990). Strong endonucleolytic cleavages were detected at all CTGG motifs within all the S probes tested, although it appears that cleavage activity at these motifs greatly depends upon adjacent DNA sequence.

5.2 Example 2

Purification and Characterization of the Immunoglobulin Switch Sequence-Specific Endonuclease (Endo-SR) from Bovine Spleen This example describes purification of the bovine enzyme to homogeneity. The nuclease cleaved all analyzed switch regions, and was found to demonstrate distinctive switch sequence affinities, which appear to be modulated by adjacent DNA sequence.

5.2.1 Materials and Methods 5.2.1.1 Preparation of Nuclear Extracts of Bovine Tissues Nuclear extracts were prepared from bovine tissues using a modified version of the method described by Dignam et al. (1983). Bovine tissue samples (~50 g) were homogenized for 15 sec in ~2 volumes of cold Buffer A [10 mM sodium phosphate (pH 6.8), 1.5 mM $MgCl_2$, 0.5 mM DTT, 0.5 mM PMSF] using a Waring blender, filtered through two layers of coarse-mesh cheesecloth and then centrifuged for 10 min at 1000 g. Nuclear pellets were homogenized in ~2 volumes of cold Buffer A with 10 strokes of a B-type glass pestle, and centrifuged as above. Nuclear pellets were homogenized with 10 strokes of an A-type glass pestle in ~2 volumes of cold Buffer A* (supplemented with 200 mM NaCl and 0.2 mM EDTA), incubated on ice for 30 min, and then centrifuged at 2500 g for 15 min. Nuclear extracts derived from these supernatants were stored at −70° C. until use, and aliquots were assayed for specific endonuclease activity as described below.

Nuclear extracts for enzyme purification were generated from bovine spleen. Spleens were dissected to remove membranes and major blood vessels, and then homogenized with an equal volume of cold Buffer B [20 mM Tris-HCl (pH 7.4), 140 mM ammonium chloride], filtered, and precipitated as described above. Cell pellets were resuspended and repelleted three times to remove contaminating red blood cell debris. Splenocytes were resuspended in ~2.5 volumes of cold Buffer A and stirred for 10 min on ice, then homogenized and centrifuged as described above. This procedure was repeated an additional three times in order to reduce cytoplasmic contamination of the nuclear pellet. Resulting nuclear pellets were resuspended in ~2 volumes of cold Buffer A*, homogenized, stirred for 30 min on ice, and centrifuged as described above. Supernatant from this step was pooled as nuclear extract (Fraction I). Nuclear extract and all subsequent chromatographic fractions were stored at −70° C. until required for analysis or further fractionation.

5.2.1.2 Purification of Bovine Endo-SR

All purification steps, unless indicated otherwise, were performed at ~4° C. Spleen crude nuclear extract (Fraction I) was clarified/fractionated by selective precipitation with sequential 30, 60 and 95% saturated ammonium sulfate precipitations. All precipitates were resuspended in ~10 volumes of cold Buffer C [20 mM sodium phosphate (pH 6.8), 0.5 mM $MgCl_2$, 0.5 mM DTT, 0.5 mM PMSF], centrifuged to remove insoluble protein aggregates, and assayed for nuclease activity as described below. Specific nuclease activity was predominantly localized to the final (60–95% saturation) precipitate. This material (Fraction II, 41 ml) was dialyzed against two sequential 1 liter volumes of cold Buffer C* (5 mM $NaHPO_4$) then supplemented with 0.6 g Betaine, 0.6 ml Nonidet P-40 (10%), 3 ml carrier ampholytes (pH 5–8, 40%; Bio-Rad), and adjusted to 60 ml with ultrapure water. Adjusted Fraction 11 material was fractionated for 3 hr in a Rotofor™ preparative isoelectric focusing cell (Bio-Rad). Peak enzyme activity focused to a pH 7.3~7.7 gradient fraction, although significant activity was detected in flanking pH fractions. Active fractions (pH 6.9–8.9, 12.4 ml) were pooled and dialyzed against two sequential 250 ml volumes of cold Buffer D [50 mM sodium acetate (pH 5.5), 100 mM NaCl, 0.5 mM $MgCl_2$, 0.5 mM DTT, 0.1% Betaine, 0.5 mM PMSF] to remove contaminating ampholytes. This material (Fraction III, 12.4 ml) was loaded onto a pre-packed Mono S strong cation exchange column (Pharmacia; 1 ml), and eluted with a linear NaCl concentration gradient (100–600 mM). Enzyme activity (Fraction IV, 2.5 ml) eluted at ~450 mM NaCl in five sequential 0.5 ml fractions. Fraction IV was concentrated to ~0.35 ml with a Microcon-3 concentrator (Amicon), then size-fractionated on a pre-packed Superose-12 size exclusion column (Pharmacia; 25 ml) previously equilibrated with Buffer E [20 mM Tris-HCl (pH 8.0), 100 mM NaCl, 0.5 mM DTT, 0.1% Betaine, 0.5 mM PMSF]. Nuclease activity eluted from this column in four sequential 0.25 ml fractions (Fraction V), corresponding to an apparent native molecular mass of ~35 000 relative to the elution profiles of bovine serum albumin (67 kDa), ovalbumin (43 000), and cytochrome C (12 400). Fractions I–V aliquots were size-fractionated on a 15% SDS-polyacrylamide gel (Coligan et al., 1991), and protein bands were visualized by ammoniacal silver staining essentially as previously described (Giulian et al., 1983). Fraction V aliquots were found to contain a single band of $M_r$~32 000, whose relative abundance directly correlated with enzymatic activity. Severe cumulative activity losses encountered during this purification process greatly reduced the specific activity and purification values determined for the final Endo-SR purification steps (Table 2). It is important to note that murine Endo-SR experienced similar activity losses during the purification process, and these cumulative losses have prevented the isolation of a pure sample of the murine enzyme (Lyon et al., 1996).

5.2.1.3 Endonucleolytic Assay and DNA Substrates

Endo-SR activity was assayed in 10 $\mu$l reactions containing 50 mM sodium acetate (pH 5.5), ~150 mM NaCl, 0.5 mM $MgCl_2$, ~250 fmoles of end-labeled DNA substrate (see below), 1 $\mu$g sheared salmon sperm DNA, and 1 $\mu$l of a diluted Endo-SR fraction. All reactions performed with bovine Endo-SR used Fraction V material (Table 2). Murine Endo-SR used in these assays was purified essentially as previously described (Lyon et al., 1996). All nuclease assays were incubated at 37° C. for 30 min, then mixed with 10 μl of formamide dye and denatured at 95° C. for 5 min prior to size-fractionation on standard sequencing gels. Endo-SR activity values (fmol/min) were determined by quantitation of the radioactivity present in specific nuclease cleavage products and intact substrate (negative control) excised from the dried gel (Lyon et al., 1996). Nuclease assays used to characterize the activity parameters of murine and bovine Endo-SR were performed essentially as previously described (Lyon et al., 1996).

End-labeled DNA substrates were prepared from plasmid DNA subclones essentially as previously described (Lyon et al 1996). DNA substrates used in this study were generated from a 253 bp murine Sμ DNA SacI-MspI subclone (Sakano et al., 1980), a 1.7 kb SacI-PstI subclone derived from a full-length Sα germline DNA clone (Aguilera et al., 1985), a 2.5 kb NdeI-EcoRI fragment of pUC-18 plasmid DNA (Vieira and Messing, 1982), and a 900 bp human Sμ DNA subclone (bp 1-900 of X56795; obtained from Drs. Zhang Ke and Andrew Saxon, Dept. of Clinical Immunology, UCLA).

5.2.1.4 DNA Sequence Analysis

All DNA sequences examined in this study were obtained from the databases of the National Center for Biotechnology Information (NCBI), as follows: MUSIGCD09 (murine Sμ; 1461 nt), X56795 (human Sμ, 4452 nt), U50149 (porcine Sμ, 4025 nt), and X13919 (shrew Sμ, 475 nt). Sμ sequence composition was analyzed with the IBI Pustell™ Sequence Analysis Software (IBI-Kodak), and switch motif frequencies were calculated by their contribution to the switch region DNA content.

5.2.2 Results 5.2.2.1 Detection of an Endo-SR-Like Activity in Bovine Tissues

A bovine endonuclease activity was identified that, similar to murine Endo-SR (Lyon et al., 1996), specifically cleaves TGGGG and TGAGC switch pentamer motifs (FIG. 1). Specific nuclease activity was detected in the nuclear extracts of all analyzed bovine tissues, but was preferentially enriched in splenic nuclear extracts. Nuclear extracts of other bovine tissues contained significantly lower levels of specific enzyme activity. Nuclear extracts derived from thymus and liver revealed ~30%, kidney ~20%, and heart and brain ≦10% of the specific activity detected in splenic extracts. Specific single cleavages were detected at TGGGG and TGAGC motifs present in a murine Sμ consensus sequence substrate. Significantly, a similar sequence motif AGAGC, located immediately upstream of these motifs was not cleaved by these extracts, suggesting specificity for consensus switch motifs. Furthermore, nuclease activity detected in these extracts appeared to be mediated by a single enzyme, since identical cleavage patterns were detected with crude nuclear extract and a pure enzyme fraction.

5.2.2.2 Purification of the Bovine Endo-SR Nuclease

Specific bovine endonuclease activity detected in these assays was subsequently purified to homogeneity from bovine spleen nuclear extracts in order to more accurately characterize the responsible enzymatic activity. Splenic nuclear extracts were sequentially fractionated by selective precipitation, isoelectric focusing, strong cation exchange chromatography, and size-exclusion chromatography (summarized in Table 2). Specific bovine nuclease activity eluted from the final purification column in a well defined peak (Fraction V, FIG. 1) with an apparent molecular weight of ~35 000, and demonstrated a ~2500-fold increase in specific activity versus crude nuclear extract (Fraction I). It is important to note that progressive losses in enzymatic activity resulted in a severe underestimate of this enzyme's purification. Silver stain analysis of SDS-PAGE fractionated purification samples detected the enrichment of a single ~32 000 protein species which directly correlated with enzymatic activity. Similarly, size-exclusion chromatography of partially purified murine Endo-SR under these conditions also revealed a roughly analogous 25~35 kDa range for murine Endo-SR activity.

TABLE 2

ENDO-SR PURIFICATION FROM BOVINE SPLENIC NUCLEAR EXTRACTS

| Fraction | Protein (μg) | Activity (units) | Specific activity (units/μg) | Purification (fold) | Yield (%) |
| --- | --- | --- | --- | --- | --- |
| I. Nuclear Extract | $7.10 \times 10^6$ | $29.3 \times 10^6$ | 4 | 1 | 100 |
| II. (NH$_4$)$_2$SO$_4$ ppt | $1.35 \times 10^5$ | $22.6 \times 10^6$ | $1.67 \times 10^2$ | 42 | 77 |
| III. Rotofor IEF | $1.96 \times 10^4$ | $6.83 \times 10^6$ | $3.48 \times 10^2$ | 87 | 23 |
| IV. Mono S | $1.26 \times 10^2$ | $4.15 \times 10^5$ | $3.29 \times 10^3$ | 824 | 1.4 |
| V. Superose 12 | 29 | $2.97 \times 10^5$ | $1.02 \times 10^4$ | 2560* | 1.0 |

*Severely underestimated value due to substantial activity losses during the purification process.

5.2.2.3 Comparison of Bovine and Murine Endo-SR Activities

Nuclease assays were performed with purified bovine nuclease (Fraction V) and partially purified murine Endo-SR (Lyon et al., 1996) to compare the activity parameters of these enzymes. As depicted in FIG. 2A, both enzymes were found to demonstrate maximal specific activity at pH 5 and pH 5.5, respectively. However, nuclease activity was significantly reduced within ±0.5 pH of these conditions, and was almost completely inhibited (≧90) by greater (±1) pH changes. Specific activity losses detected in these assays did not reflect progressive denaturation at extreme pH, since both enzymes were found to retain almost full activity after exposure to strongly acidic (pH 2) or mildly alkaline (pH 8) reaction conditions (tested at pH 5.5).

Similar assays were subsequently performed to address the potential $M^{2+}$ cofactor requirement(s) of these enzymes. As shown by FIG. 2B, neither the murine nor the bovine nuclease required supplemental $M^{2+}$ for full specific activity, and both enzymes were relatively resistant to low concentrations (≦50 μM) of EDTA and most common $M^{2+}$ cofactors. At these low concentrations, only Zn and Mg were found to produce any significant degree of enzyme inhibition. However, at higher ($\geq 500$ $\mu$M) concentrations, all M$^{2+}$ cofactors (and EDTA) resulted in some degree of enzyme inhibition. Both nucleases revealed roughly similar inhibition profiles (Zn>EDTA>Ca), and differed primarily in their response to Mg. Specifically, the murine enzyme demonstrated a greater sensitivity to Mg than to EDTA (Zn>Mg>EDTA>Ca), while the bovine enzyme revealed greater inhibition by EDTA than by Mg (Zn>EDTA>Mg>Ca). Additionally, while both nucleases demonstrated roughly similar inhibition profiles, murine nuclease activity was more readily inhibited than bovine nuclease activity at all inhibitor concentrations. Enzyme activity losses detected at high ($\geq 5$ mM) M$^{2+}$ or EDTA concentrations did not appear to result from ionic strength effects, since neither enzyme was significantly effected by equivalent changes ($\geq 250$ mM) in buffer NaCl concentration.

5.2.2.4 Endonucleolytic Cleavage of Consensus Murine S$\mu$ Repeat Substrates

Nuclease assays were performed with subcloned oligonucleotides containing short regions of murine S$\mu$ DNA consensus sequence in order to accurately characterize and compare the double-stranded cleavage specificities of the murine and bovine nucleases. Both nucleases reproducibly cleaved TGGGG and TGAGC motifs and generated similar repetitive cleavage patterns. However, S$\mu$ DNA cleavages detected in these assays were distinctive for each enzyme. Both enzymes generated precise sense-strand cleavages within TGAGC motifs, but the murine nuclease cut after the first nucleotide and the bovine nuclease after the fourth nucleotide of this motif. Strong antisense cleavages at TGAGC motifs were trailed by a series of weaker cleavages. Significantly, antisense cleavages within these motifs were identical for both enzymes except at the third position.

The bovine and murine nucleases produced prominent yet distinct sense-strand cleavages at a single S$\mu$ substrate TGGGG motif. The murine enzyme cleaved this motif after the first and second nucleotides while the bovine enzyme cut this motif only after the fourth nucleotide. Both enzymes also generated antisense cuts before the second and fourth nucleotides of the TGGGG motif, although a weak cleavage before the first nucleotide of this motif was detected only with the bovine nuclease.

Cleavages generated by these nucleases should produce potential double-stranded breaks within TGGGG and TGAGC motifs. Cleavages detected on the antisense strands of these DNA substrates revealed considerably less specificity than detected at the corresponding sense strand cleavage sites. Nuclease activity at these motifs could potentially produce a large number of different free ends. Strong cuts within TGGGG motifs should generate blunt ends (murine) or 3' overhangs (both), while weak or adjacent cleavages could also generate 5' overhangs, blunt ends, or 3' overhangs. Similarly, strong cleavages within TGAGC motifs should generate 5' overhangs, while additional weak antisense-strand cleavages could also produce shortened 5' overhangs, blunt ends, or 3' overhangs.

Interestingly, Endo-SR activity at consensus motifs appeared to be modulated by adjacent sequence composition. Specific sense-strand cleavage sites were either significantly repressed (murine) or enhanced (bovine) at a TGAGC motif directly adjacent a TGGGG motif. Adjacent sequence also appeared to influence antisense cleavage sites, since both enzymes revealed altered affinity for antisense cleavage sites adjacent to a TGGGG motif. Specifically, murine Endo-SR demonstrated reduced affinity for antisense cleavage sites adjacent to this motif, while bovine Endo-SR revealed enhanced affinity for antisense cleavage sites within the next TGAGC motif.

5.2.2.5 Endonucleolytic Cleavage of Germline Switch Region DNA Substrates

Nuclease assays were subsequently performed with germline switch DNA substrates in order to characterize the essential recognition sequences of bovine and murine Endo-SR. Both nucleases cleaved a murine germline S$\mu$ DNA substrate to produce cleavage patterns similar to those previously detected within a consensus S$\mu$ repeat structure. Endo-SR affinity for S$\mu$ DNA TGAGC motifs appeared to be strongly influenced by adjacent TGGGG motifs. Nuclease assays performed with a human S$\mu$ DNA substrate, which contains a more degenerate repeat structure, also yielded fundamentally similar cleavage patterns. Both enzymes produced strong cleavage sites within all S$\mu$ DNA TGGGC motifs, and weaker cleavages within TGAGC motifs. Novel bovine Endo-SR double cleavage sites detected within TGGGC motifs appeared to resemble shifted versions of murine Endo-SR double cleavage sites. However, each enzyme revealed unique specificity for single-nucleotide variants (T<u>A</u>GGC and <u>G</u>GGC) of this motif.

Nuclease assays performed with a murine S$\alpha$ DNA substrate, revealed more complex cleavage patterns than previously observed with S$\mu$ DNA substrates, possibly due to the greater degeneracy of the analyzed S$\alpha$ DNA sequence. Strong Endo-SR cleavages were again predominantly localized to consensus TGGGC and TGGGA motifs or single-nucleotide variants (TGG<u>A</u>C and T<u>A</u>GGA) of these motifs, while relatively weaker cleavages were primarily detected at consensus TGAGC motifs. Significantly, a single consensus TGGGC motif was cleaved with dramatically different affinity by the bovine and murine enzymes. Both enzymes produced characteristic double cleavages, although cleavages generated by bovine Endo-SR were detectable only upon prolonged exposure. Similar motifs present in human S$\mu$ DNA were cleaved with approximately equal affinities by both enzymes. These results indicate that adjacent sequence composition might have a profound effect on the specificity of these enzymes.

Nuclease assays performed with switch region DNA have shown that both enzymes recognize and cleave degenerate switch motifs within repetitive switch region DNA and are influenced by adjacent sequence. Nuclease assays were therefore also performed with an unrelated plasmid DNA substrate to examine the ability of these enzymes to cleave non-repetitive DNA sequence. Sporadic weak cleavages detected within this DNA substrate predominantly mapped to cryptic single (T<u>A</u>GGC, TGG<u>A</u>A, TG<u>T</u>GA) or double ( <u>C</u>AGGC and T<u>AT</u>GC) nucleotide variants of the G-rich TGGGN switch pentamer motif. Nuclease activity at these sites, however, was dramatically reduced from the activity seen within switch region DNA, which again suggested the importance of adjacent sequence to recognition and cleavage of individual switch pentamer motifs. 5.2.3 Discussion Recently, during a search for factors, which specifically interact with switch region DNA, the inventors identified and partially purified a murine endonuclease activity, Endo-SR, which preferentially cleaves G-rich switch pentamer motifs (Lyon et al., 1996). All attempts to purify this nuclease to homogeneity from murine tissue or cell lines were unsuccessful, however, due the relative scarcity of the responsible enzyme and its rapid inactivation upon purification. Nuclease assays performed with bovine tissues have recently identified a homologous endonuclease activity that, similar to murine Endo-SR (Lyon et al., 1996), is preferentially enriched in nuclear extracts of spleen and thymus.

Neither murine Endo-SR nor this bovine nuclease demonstrates significant enzymatic similarities to any previously described G-specific mammalian endonucleases (see Lyon et al 1996). Both nucleases do, however, share several distinguishing features. Specifically, both enzymes demonstrate pH optimas well below those of previously characterized mammalian endonucleases, and are strongly inhibited ($\geq$90%) at ±1 pH units away from these conditions (FIG. 2B). Also, unlike most other previously characterized endonucleases, neither enzyme requires supplementary $M^{2+}$ for full specific activity. Surprisingly, however, both nucleases are inhibited by relatively low ($\leq$500 mM) concentrations of $M^{2+}$ and EDTA, potentially via displacement of a tightly held divalent met al co-factor.

Nuclease assays performed with germline S$\mu$ and S$\alpha$ DNA substrates revealed cleavage patterns similar to those detected with short regions of murine S$\mu$ DNA consensus sequence. Novel bovine Endo-SR double cleavage sites at TGGGC motifs resemble double cleavage sites produced at TGGGC and TGGGG motifs by murine Endo-SR. Nuclease activity at TGGGC and TGAGC motifs primarily differs by a single sense-strand cleavage, however, and thus these enzymes also demonstrate a similar 'shifted' cleavage site homology at TGAGC motifs. Due to the similarity of TGGGC and TGAGC motifs, it seems likely that these enzymes recognize one or both of these motifs as a degenerate version of a common recognition sequence. Since both nucleases primarily produce strong cleavages at TGGGN motifs, it appears that these enzymes preferentially recognize this G-rich consensus sequence.

The bovine and murine nucleases demonstrated distinctive cleavage affinities for several consensus motifs within the germline S-region DNA substrates. Both enzymes exhibited significantly reduced affinity for all TGAGC motifs directly preceded (murine) or followed (bovine) by TGGGG motifs. Both nucleases also demonstrated distinctive affinity for S$\mu$ and S$\alpha$ TGGGC motifs, apparently due to the recognition of adjacent DNA sequence. Based on these data, these enzymes may interact with recognition sequences that extend beyond the defined boundaries of the cleaved switch pentamers.

As shown in Table 3, sequence analysis of published germline S$\mu$ DNA sequences (Butler and Brown, 1994; Ishiguro et al., 1989; Mills et al., 1990; Sakano et al., 1980) reveals strong compositional biases for certain TGGGN motifs. Single-nucleotide variants of the TGGGN motifs are found at relatively low frequencies, suggesting that these motifs have been conserved through evolution. Murine S$\mu$ DNA predominantly contains the TGGG<u>G</u>(63%) form of this motif, while all other S$\mu$ DNA sequences are highly enriched for TGGG<u>C</u>(46%–86%) and, to a lesser extent, TGGG<u>T</u>(8%–39%) motifs. However, since cows and pigs belong to the same phylogenetic order (Artiodactyla), it seems likely that the sequence composition of bovine S$\mu$ DNA will prove to be roughly homologous to that of porcine S$\mu$ DNA (i.e., heavily enriched for TGGGC and TGAGC motifs). Significantly, due to the unique sequence specificities of murine and bovine Endo-SR, the sequence compositions of murine (TGGGG) and bovine (TGGGC) S$\mu$ region DNA should result in highly similar cleavages within the S$\mu$ DNA of these species.

TABLE 3

COMPARISON OF MAMMALIAN SM REGION DNA COMPOSITION

| Switch motifs | Mouse (1461 bp) | S$\mu$ region DNA[a] Human (4452 bp) | PIG (4025 BP) | Shrew (475 bp) |
|---|---|---|---|---|
| TGAGC | 145[b] | 182 | 219 | 43 |
| TGGGN | 63 | 239 | 209 | 28 |
| TGGGG | 40 | 10 | 12 | 1 |
| TGGGC | 9 | 205 | 125 | 13 |
| TGGGA | 8 | 5 | 5 | 3 |
| TGGGT | 6 | 19 | 67 | 11 |
| TGAGC TGAGC | 80 | 40 | 49 | 12 |
| TGAGC TGGGN | 49 | 50 | 91 | 22 |
| TGGGN TGAGC | 43 | 73 | 115 | 12 |
| TGGGN TGGGN | 2 | 80 | 18 | 1 |

[a]Nucleotide sequences were obtained from the NCBI.
[b]Total number of motifs detected within germline S-region.

All analyzed S$\mu$ regions were found to contain disproportionate numbers of adjacent TGGGN and TGAGC motifs (see Table 3). Murine S$\mu$ DNA contained the most dramatic example of an "ordered" switch pentamer distribution, but similar motif clusters were detected in all analyzed S$\mu$ DNA sequences. Since Endo-SR activity appears to be strongly influenced by adjacent sequence, the relatively high incidence of switch "decamers" may have direct significance to the choice of switch rearrangement sites. Specifically, the switch decamers may dictate or enhance nuclease cleavage sites found within these regions.

Since Endo-SR recognition of switch motifs has been found to be strongly influenced by adjacent DNA sequence, it is tempting to speculate that Endo-SR recognizes degenerate direct repeat sequences within highly repetitive switch regions as a homodimer. Several previously described mammalian nucleases are known to function as homo- or heterodimeric enzymes. Bovine Endo-SR activity, however, demonstrates an apparent molecular mass of ~35 000 when fractionated by native size exclusion chromatography, and directly corresponds to an $M_r$~32 000 protein species identified in these fractions. Due to the close correspondence of these molecular weight values, it appears unlikely that purified bovine Endo-SR forms stable homodimers under these conditions. However, while bovine Endo-SR may not form stable protein dimers in solution, it is conceivable that this protein could form active homodimeric or multimeric enzyme complexes during the recognition of adjacent motifs within highly repetitive switch region DNA. Significantly, formation of such higher-order complexes could potentially enhance Endo-SR affinity for switch repeat sequences (SRS) within these regions and account for the effect of adjacent sequence upon enzyme activity.

Switch region transcriptional activation has been proposed to be a necessary step for recombination as this event could increase accessibility for switch recombination factors (Bottaro et al., 1994; Xu et al., 1993; Zhang et al., 1993). However, work has shown that high-level transcriptional activation, by itself, does not efficiently induce switch recombination (Bottaro et al., 1994). Actual switch DNA rearrangements thus appear likely to require activation of a putative switch-recombinase activity (Purkerson and Isakson, 1992). Such an activity should be highly regulated during B lymphocyte development in order to prevent inappropriate degradation or rearrangement of genomic SRS sequences. Endo-SR activity is almost completely inhibited (~98%) at physiological pH and only demonstrates maximal activity under moderately acidic conditions (~pH 5) that should not normally be encountered in the nuclear micro-environment of most cells. Efficient cleavage of SRS motifs during switch recombination may therefore require de novo activation of Endo-SR via a regulatory post-translational modification or protein-protein interaction. Endo-SR activity is not restricted to lymphoid tissues and thus may have a secondary "housekeeping" function, perhaps in DNA repair, similar to a number of accessory factors previously shown to be involved in V-(D)-J recombination (Oettinger, 1996; Taccioli et al., 1992).

As previously proposed (Lyon et al., 1996), Endo-SR could either directly recognize SRS motifs within accessible, transcriptionally active switch region DNA or be recruited to activated switch regions as part of a putative switch-recombinase complex. Endo-SR activity should, in either case, produce targeted single-stranded nicks or double-stranded breaks in accessible switch region SRS motifs, which could serve as templates for error-prone DNA synthesis/repair and non-homologous recombination events (Dunnick et al., 1989; Dunnick et al., 1993). All of the putative single-strand nicks and double-stranded cuts produced by Endo-SR are, however, consistent with previously characterized switch recombination breakpoints (Dunnick et al., 1993; Kenter et al., 1993; Mowatt et al., 1986; Petrini and Dunnick, 1989; Wuerffel et al., 1992), and could easily account for the DNA deletions, mutations, duplications and insertions commonly found at switch recombination breakpoints and chromosomal DNA translocations (Aguilera et al., 1985; Dunnick et al., 1993; Dunnick et al., 1989; Gerondakis et al., 1984).

5.3 Example 3

Sequence Analysis of Human and Mouse Endo-SR

Protein sequence analysis of the ~32 kDa protein has generated three distinct peptide sequences, two of which were independently generated from samples derived from different Endo-SR purification procedures (FIG. 7). BLASTP computer homology searches (Altschul et al., 1990) performed with these peptides have shown that all three peptides demonstrate significant homology to a predicated 40 kDa human protein, R31240-2, encoded by a proposed gene within the 19p13.2 chromosomal region. Several proteins of known function also demonstrated weak homologies to these peptides, including several proteins with nucleic acid binding and/or phosphodiesterase activities. Short sequence homologies to these proteins, however, while appropriate to the known function of Endo-SR, were significantly weaker than those detected with the predicted R31240-2 gene product. Similar short homology regions were also detected in several proteins with no apparent relevance to Endo-SR function.

Since all three peptides demonstrated statistically significant homologies to the predicted R31240-2 protein sequence, this protein represents a strong candidate for the human analogue of Endo-SR. A protein homology search conducted with the hypothetical R31240-2 protein sequence demonstrated that this protein was most homologous to three *Caenorhabditis elegans* predicted proteins encoded by C07B5.5 on chromosome X and K04H4.6, and F09G8.2 on chromosome III. Nothing is currently known about the putative functions of these three hypothetical proteins, and homology searches conducted with the amino acid sequences of these predicted proteins have not revealed significant homologies to other proteins of known function. R31240-2 was also found to be homologous to a 43 kDa secreted glycoprotein expressed by the intracellular parasite *Trichinella spiralis*. This protein has been shown to undergo nuclear translocation and implicated in the pathogenic transformation of muscle cell satellite nuclei to "nurse" cells (Vassilatis et al., 1992), although its precise function in parasite infection is as yet unknown. R31240-2 protein sequence also demonstrated limited homologies to several proteins of known function, including potentially relevant homologies to several DNA binding proteins and several enzymes involved in the reduction of phosphodiester and/or pyrophosphate bonds. None of these homologies, however, demonstrated any appreciable degree of statistical significance.

Since analyses of R31240-2 have revealed that this putative protein demonstrates both amino acid and potential functional homologies to purified bovine Endo-SR protein, the inventors isolated a R31240-2 cDNA clone in order to address the potential role R31240-2 expression in switch recombination. Switch rearrangement events are primarily restricted to the late pre-B to mature B cell stage of B lymphocyte differentiation and thus R31240-2 should be expressed in these cell stages if it is directly involved in the switch recombination process. Reverse transcriptase-polymerase chain reaction (RT-PCR™) studies, performed with cDNA derived from the Nalm6 human pre-B cell line and R31240-2 gene-specific primers, have shown that R31240-2 mRNA is expressed in human Pre-B cells, since RT-PCR™ amplifies a DNA fragment that directly corresponds to the predicted coding sequence of the R31240-2 gene. Work has also demonstrated that the corresponding R31240-2 gene product is also expressed in this cell line, since specific antibodies raised against recombinant R31240-2 protein strongly hybridize with a single ~40 kDa protein species during western analysis of Nalm6 nuclear extracts. Results indicate that R31240-2 protein is most highly expressed in lymphoid cell lines, and only weakly expressed in non-lymphoid cell lines.

Sequence analysis of the RT-PCR™ gene product has revealed a near perfect homology to the predicated R31240-2 mRNA transcript. The Nalm6 RT-PCR™ product contains two single-nucleotide (nt) point mutations (nt 435: C→T and nt 957: A→G) and a 36 nt insertion within the predicated R31240-2 coding region. Significantly, both point mutations are silent, while the 36 nt "insertion" corresponds to putative intron sequence at the junction of the predicated splice junction of Exon IV, contains no in-frame stop codons, and does not disrupt the predicated reading frame of the downstream coding sequence. Sequence analysis of R31240-2 germline DNA sequence has shown that the region directly adjacent to this putative "insertion" contains a 5' splice site consensus sequence, suggesting that the isolated R31240-2 cDNA most likely arises from bona fide splicing of the R31240-2 primary transcript rather than from a RT-PCR™ artifact. No alternate R31240-2 cDNA species were detected in this assay, indicating that the originally predicated 5' splice junction site at Exon IV is not spliced to produce an alternate R31240-2 mRNA.

Switch recombination has been primarily characterized using mouse model systems. Studies to examine the potential role of R31240-2 in switch recombination can thus most easily be addressed by gene knockout studies performed in mouse cell lines or recombinant mice. A cosmid library of mouse genomic DNA was screened for all clones that strongly hybridize with an R31240-2 cDNA probe in preparation for these studies. Restriction mapping of the isolated cosmid clones identified three apparently overlapping clones, two of which generated identical restriction maps. Due to the detected degree of cosmid overlap it seems very unlikely that the mouse genome contains an R31240-2 gene family.

Sequence analysis of the mouse genomic DNA cosmid clones also demonstrated a substantial degree of sequence conservation between the human and mouse genes. As shown in FIG. 9A, FIG. 9B, FIG. 9C, and FIG. 9D, these clones demonstrated significant homology to the last three exons of the human R31240-2 gene locus. Conceptual translation of the two mouse sequences corresponding to Exons V and VI of the human R31240-2 gene produces a predicted protein fragment that reveals substantial homology to the R31240-2 protein and significantly diverges only within the last few amino acids of this protein fragment. The predicted mouse R-31240-2 Exon V coding region displays considerable homology to human R31240-2 Exon V and appears likely to demonstrate the same splicing due to the conservation of essential nucleotides within the predicted 3' and 5'Exon V splice junctions sequences. Sequence at the beginning of this insert also demonstrates short homology to R31240-2 Exon IV, but since two essential 5' splice junction nucleotides are not conserved within the mouse sequence it is unlikely this region directly corresponds to the Exon IV region of human R31240-2. Mouse sequence corresponding to human R31240-2 Exon VI sequence initiated just after the known human 3' splice junction, and thus no prediction can be made about the 3' splicing of the mouse R31240-2 Exon VI region. Due to these Renato Aguilera et al. uncertainties, accurate comparison of the human and mouse R3 1240-2 coding sequences will require the isolation and sequencing of a mouse R3 1240-2 cDNA clone.

Sequence alignment of the murine R31240-2 protein with three hypothetical C. elegans proteins (C07B5.5, kO4H4.6 and F09GS.2) has revealed a significant amount of protein conservation among these proteins. This alignment has demonstrated that several short stretches of near perfect homology (underlined) are interspersed within larger regions of reduced homology. Secondary protein homology searches were conducted with regions of strong homology detected during this alignment, to determine if these stretches of protein homology represent conserved function domains. Computer homology searches performed with these consensus regions primarily detect weak homologies to a limited number of protein classes, primarily nucleic-acid binding proteins and proteins with phosphodiesterase, pyrophosphatase and/or phosphatase activities, consistent with the functional domains expected for Endo-SR activity. However, protein homologies determined in this fashion, while suggestive, are neither stringent nor consistent enough to reasonably assign putative functions to specific protein regions. See new evidence for role in apoptosis.

The degree of similarity between R31240-2 and the three predicted C. elegans proteins suggests that they may share fundamental functional similarities. However, any functional similarities that may exist among these proteins are most likely restricted to the basic processes of recombination or DNA repair due to the extreme evolutionary distance between the involved species. Significantly, previous work has demonstrated that Endo-SR activity is not restricted to recombinationally active B cells, but is expressed at some level in all assayed tissues or cell types, indicating a probable secondary role for Endo-SR activity in non-lymphocyte DNA recombination, repair or degradation processes. Endo-SR may therefore also play an accessory role in switch recombination analogous to several DNA repair proteins involved in V-(D)-J recombination (Tacciolli et al., 1993; Gu et al., 1997; Ramsden et al., 1997), another lymphocyte sequence-sequence specific recombination process.

These examples describe the characterization of a novel mammalian endonuclease activity that preferentially cleaves two switch pentamer motifs, TGGGN and TGAGC, previously implicated as potential recognition signals in the switch recombination process. This nuclease activity, which was designated Endo-SR, appears to be a putative switch endonuclease activity required for the generation of the site-specific DNA rearrangements characteristic of switch recombination.

Endo-SR activity is preferentially enriched in the lymphoid tissues of all analyzed species, but is not restricted to the B lymphocyte cell lineage, as might be expected for the proposed switch endonuclease activity. Since Endo-SR does not display a lineage restricted expression pattern, it seems likely that this nuclease activity may display a secondary, "housekeeping" function in DNA recombination or repair, as has been shown for some of the accessory factors involved in V(D)J recombination (Tacciolli et al., 1993; Gu et al., 1997; Ramsden et al., 1997).

Nuclease assays performed with murine, human or bovine cell lines or tissues have detected similar nuclease activities in all three species, although each species appears to demonstrate slight differences in the recognition and cleavage specificity of Endo-SR. Species-specific differences in Endo-SR activity primarily result in species-specific cleavage of switch pentamer motifs and selective recognition and cleavage of switch pentamer variant sequences. Selective recognition of specific switch pentamer variants may reflect species-specific differences in switch region sequence composition.

Several groups have shown that several G-rich chromosomal DNA regions, aside from switch region DNA, appear to function as recombination hotspots (Konopka et al., 1985; Weinreb et al., 1985; Wohlrab et al., 1987), and a few mammalian nucleases have now been shown to demonstrate specificity for G-rich DNA sequences (Ruiz-Carrillo and Renaud, 1987; Gottlieb and Muzyczka, 1990). However, none of these nucleases have yet been shown to demonstrate the sequence-specificity and restricted expression pattern predicted for a candidate switch endonuclease activity. Neither murine nor bovine Endo-SR activity reveals any significant homologies to these nucleases, but instead share several features that readily distinguish them from all other described mammalian endonuclease activities. Specifically, murine and bovine Endo-SR demonstrate pH optimas well below those of most other known mammalian nucleases, and are strongly inhibited when assayed at more than a pH unit above or below these values. Furthermore, unlike most other described nucleases, Endo-SR does not require supplemental $M^{2+}$ for full and specific nuclease activity. However, Endo-SR activity can be efficiently repressed by exposure to relatively low concentrations of several common $M^{2+}$ or EDTA, suggesting that these factors compete for or disrupt the binding of a tightly held $M^{2+}$ cofactor.

Peptide sequence analysis of purified bovine Endo-SR has generated three peptides that demonstrate substantial homology to a hypothetical 40 kDa protein, R31240-2, encoded by a predicted gene recently identified within the p13.2 region of human chromosome 19. Computer homology searches conducted with the R31240-2 protein revealed strong homologies to four other predicted proteins of unknown function as well as several weak homologies to known proteins consistent with those expected for a putative switch endonuclease. Studies have demonstrated that R31240-2, presumably the human homolog of Endo-SR, is expressed in the human Nalm6 pre-B cell line. This protein, like Endo-SR, is preferentially expressed in lymphoid cell lines, but not restricted to this cell lineage. Screening of a mouse genomic DNA library with an R31240-2 cDNA probe has resulted in the isolation of three apparently overlapping cosmid clones, suggesting that R31240-2 is encoded by a single-copy gene and that this gene does not belong to a larger gene family.

The role of Endo-SR activity in switch recombination can also be addressed by determination of recombination frequency after selective repression of Endo-SR activity with anti-sense vector constructs or by gene-knockout. Since Endo-SR expression is not restricted to the B cell lineage, it may be involved in secondary, "housekeeping" functions common to all cell types. Based on its characterized nuclease activity, low-level Endo-SR activity in non-lymphoid cell types appears most likely to be involved in DNA recombination, repair or degradation. Work has demonstrated that many genes involved in "housekeeping" processes like those described above can be deleted without any apparent short-term adverse effects on cell viability (Engleward et al., 1996; Reitmar et al., 1995; de Vries et al., 1996; Roest et al., 1996; Rolink et al., 1996; Lowsky et al., 1997; Sukumi et al., 1997; Weeda et al., 1997), and thus it seems likely that deletion or short-term repression of Endo-SR activity will not prove lethal to the affected cell lines.

Specific induction of efficient switch recombination has been shown to require the integration of several diverse signals, and switch recombination demonstrates different degrees of lineage restriction depending upon the context (chromosomal or extrachromosomal) of the recognized switch region DNA sequences. Recently several cell lines have been shown to undergo relatively high-levels of switch recombination during in vitro culture. However, while these cell lines could be used to address the in vivo relevance of Endo-SR to switch recombination, a recombinant mouse gene-knockout model should provide a more accurate view of in vivo switch recombination. Switch recombination frequency in this system could be directly addressed by measurement of the serum levels of the various Ig isotypes in wild-type, heterozygous and homozygous knockout mice.

5.4 Example 4

DNA Sequence of the Murine Endo-SR Gene (SEQ ID NO:1)

ATGGCAACACTGAGATCGCTGCTGCTG-GCTGCGCTGCTGTGGGTCCCTGC-CGAAGCCCTG AGCTGCTATGGGGACTC-CGGGCAGCCTGTGGATTGGTTCGTGGTATACA AGCTGCCGGCT CACAGCGGGTCTAGG-GATACTCCAAAGGGACTGACGTG-TAAATACATGGACCAGAACTCC GACGGTTG-GCAAGACGGTGTAGGGTACATCAACAGCCCG GAGGGAGCCGTGGGCCGCAGC TTGCAGCCAT-TGTACCGAAAGAACTCCAGCCAGCTGGC-CTTTCTACTCTACAACGACCAA CCTC-CTAAATCCAGCTCAACTCGGGACTCTACCGGC CATGGGCATACGAAGGGCAAGCAG CTAAC-CTACACCTATCCCCTTGTCTATGACCA-CAAGCTGGAAGGCTTCTTCGCTCAGAAA TTACCCTACACCTATCCCCTTGTCTAT-GACCACAAGCTGGAAGGCTTCTTCGCT-CAGAAA TTACCTGACCTAGAGACGGTGAT-CAAGAACCAACATGTCCTCCATGAGCCCTGG AATAGC AGTGTAATACTCACTTC-CCAAGCTGGGGCCACCTTCCA-GAGCTTTGCCAAATTTGGAAAA TTTGGAGAT-GACCTGTACTCCGGATGGTTGGCAGAA

5.5 Example 5

Polypeptide of the Murine Endo-SR Protein (SEQ ID NO:2)

MATLRSLLLAALLWVPAEALSCYGDS-GQPVDWFVVYKLPAHSGSRDTPKGLTCK-YMDQNS DGWQDGVGYINSPEGAVGRSLQ-PLYRKNSSQLAFLLYNDQPPKSSSTRDSTGHG HTKGKQ LTYTYPLVYDHKLEGFFAQKLPDLET-VIKNQHVLHEPWNSSVILTSQAGATFQSFAKFGK FGDDLYSGWLAE

5.6 Example 6

5' Fragment of the Genomic Murine Endo-SR Gene (SEQ ID NO:3)

Shown is an 802-base pair 5' fragment of the mouse Endo-SR/DNase II germline DNA sequence. The coding sequences are underlined. Exon 1 extends from position 1 to 95, exon 2, from 210 to 387, and exon 3, from 482 to 560.

<u>ATGGCAACACTGAGATCGCTGCTGCTGGCTGCGCCGCTGTGGGTCCTGCCCGAAGCCCTG</u>

<u>AGCTGCTATGGGGACTCCGGGCAGCCTGTGGATTGGT</u>GAGTAAGTAGTCGCGGGACTGTC

CCCCGCACACTGCCTGGGGACCGGCGCGGGAATCCAAAAAACCTCAGATTCCTTTTCTCT

CCCAACCTCATGTCTTCACGGACCTCCAG<u>GTTCGTGGTATACAAGCTGCCGGCTCACAGC</u>

<u>GGGTCTAGGGATACTCCAAAGGGACTGACGTATAAATACATGGACCAAAACTCCGACGGA</u>

<u>TGGCAAGACGGTGTAGGGTATATCAACAGCTCGGAGGGAGCCGTGGGCCGCAGCTTGCAG</u>

<u>CCATTGTACCGAAAGAACTCCAGCC</u>AGGTGACTTGAGTGCCTTCGGAACCCGGGCCGGGA

CACTGTGGTGGGTCTCGCCGGGAAGGGAAGGTAGTTACATAGCCTCTGTGCATTCTCCTA

GCTGGCCTTTCTACTCTACAACGACCAACCTCCTAAATCCAGCTCAGCTCGGGACTCTAC

CGGCCATGGGCATACAAAGGGTGAGAAGCTTGGACTGGTGGTCCTGGAACCTCCCTGAAT

TGTAAATTTTACCCTCACTAACCTTCCGCCTGATGAAGGTGGGGATTTGCCTGTCCTGG

```
NCTCCGTTTCTCGCTCTAAAACCCANCCATCTGANGCCCCTACCTGCTTGCANGTTAACT

AACTTGACNCTNCCTCCGGTTCAGGTTTTCCTGCNCCTGAACAAAAAAGGGGNTTCTGGC

TTGTTCCCANTNTNCCNCCCTC.........
```

5.7 Example 7

3' Fragment of the Genomic Murine Endo-SR Gene (SEQ ID NO:4)

Shown is a 1582-base pair 3' fragment of the mouse Endo-SRIDNase II gernline DNA sequence. The coding sequences are underlined. Exon 4 extends from position (x+)1 to (x+)32, exon 5, from (x+)54 to (x+)311, and exon 6, from (X+)1025 to (X+)1371, where x is the sequence remaining upstream of this fragment in the genomic clone that is downstream of the 5' fragment shown above as SEQ ID NO:3.

```
X+.........GTCCTTCCCGTTCACTCAGTTTGCAAGGATTGGTGAGTTGAATCACTGA

GAAGCCAAGCTTCAAATTCTTCTGAGGAACCAGTCTCACACGGCTCCCTCGCCTTGTCTT

CTAGGCAAGCAGCTAACCTACACCTATCCCCTTGTCTATGACCACAAGCTGGAAGGCTTC

TTCGCTCAGAAATTACCTGACCTAGAGACGGTGATCAAGAACCAACATGTCCTCCATGAG

CCCTGGAATAGCAGTGTAATACTCACTTCCCAAGCTGGGGCCACCTTCCAGAGCTTTGCC

AAATTTGGAAAATTTGGAGATGGTAAGCCTTGATGTTGAGGGGTGGGGGAGGGCACTTT

CGTTGTAGAAGGGGGTCCCTAGTATCCCTAGGCCTGCGGGCAACACATTTAGAGCCCAGA

TGTCTTTGGGAGTCATATTACAATAATAACTATGAGCAGTAAACAGCCAGCAGACGGGTT

GGGCGGGTGATACATATCTGTGACCTCAGCACTGTGGGGCGGAGATGGAAGCTTGAAGT

CAGCCAACAGACCTAGGTTCAAATGTTGGTTTCTGGATGTGTAATATACAATACAACCTG

AGCCTGTTTGCTCACCTGAAAAATTAGGATATTAAGGGTTCCCTTAGTGGGTTGTGAAAT

AACACATAATTGTTTGGTAAGGATTCCCTTTAGGGGTGTGGGGAGGCGGGCCCTCACTGT

GTATCCCTGGCTGGTNTGGAACTCTCAGAGAGCCATCTGCCTCTACTGTCTCAGCGCAGA

CTTTAAAGGCTTGAGTCTCCATGCCCAGCCTATGTGTTTGTGTAAGACCTCTTTACATTC

CAGGCTAGACTCCATCTGAGAGCCTCTTGTTCCAGTTTTTGAGTGTTAGGGCTGCAGGTG

GACCTGGAGAGGGACCTGACCTGTTATAGGGGCTGCTTAGGTTCACGTCATTCCAAAGTA

GAACATTTGAGCGGAGCAGGAGCCATACCGAGGAATGTACCAGTGCCCTTCACTTCATCT

TTCTTTCCCCTGCAGACCTGTACTCCGGATGGTTGGCAGAAGCCCTTGGCACCAACCTAC

AGGTCCAGTTCTGGCAAAATTCTCCAGGCATCCTGCCCTCCAACTGCTCTGGAGCCTATC

AGGTTCTGGATGTGACACAGACAGGATTCCCTGGCCCATCTAGACTAACTTTCAGTGCCA

CAGAGGACCACTCCAAATGGTGTGTGGCCCCTCAAGGGCCCTGGGCCTGTGTGGGTGACA

CGAATAGGAACAAAGCAGAGACACACCGAGGTGGCGGCACAGTATGCACCCAACTGCCTT

CCTTTTGGAAGGCCTTCCAGTCCCTGGTGAAAGACTGGAAACCCTGTATAGAGGGGAGCT

GACTGAAGCCCATCGGAGCAAAGGACTAAGACTCCGCAGTCTAACCAGGTGGGGCCGGA

CTAGCCTTTACCCCAGCACTTGGGAAGCAGAAGCAGGTGGATCGATTCTCTCTCTCTCTC

TGGTTTTCCGAGACAGGGTTTCTCTGTGTTACCCTTGGCTGTCCTGGAAACTCACTCTGT

AGAACAAGGCCTGGGCCTCCAACTCCAAATCTG
```

References

The following references, to the extent that they provide exemplary procedural or other details supplementary to those set forth herein, are specifically incorporated herein by reference.

U.S. Pat. No. 4,196,265, issued Apr. 1, 1980
U.S. Pat. No. 4,554,101, issued Nov. 19, 1985
U.S. Pat. No. 4,683,195, issued Jul. 28, 1987
U.S. Pat. No. 4,683,202, issued, Jul. 28, 1987
U.S. Pat. No. 4,965,188, issued Oct. 23, 1990
U.S. Pat. No. 4,971,908, issued Nov. 20, 1990
U.S. Pat. No. 5,176,995, issued Jan. 5, 1993
U.S. Pat. No. 5,225,341, issued Jul. 6, 1993
U.S. Pat. No. 5,276,269, issued Jan. 14, 1994
U.S. Pat. No. 5,384,253, issued Jan. 24, 1995
U.S. Pat. No. 5,399,363, issued Mar. 21, 1995
U.S. Pat. No. 5,466,468, issued Nov. 14, 1995
U.S. Pat. No. 5,482,852, issued Jan. 9, 1996
U.S. Pat. No. 5,508,468, issued Apr. 16, 1996
U.S. Pat. No. 5,543,158, issued Apr. 6, 1996
U.S. Pat. No. 5,550,318, issued Aug. 27, 1996
U.S. Pat. No. 5,567,434, issued Oct. 22, 1996
U.S. Pat. No. 5,580,579, issued Dec. 3, 1996
U.S. Pat. No. 5,591,317, issued Jan. 7, 1997
U.S. Pat. No. 5,610,288, issued Mar. 11, 1997
U.S. Pat. No. 5,641,515, issued Jun. 24, 1997
U.S. Pat. No. 5,656,016, issued Aug. 12, 1997
U.S. Pat. No. 5,697,899, issued Dec. 16, 1997
U.S. Pat. No. 5,718,709, issued Feb. 17, 1998
U.S. Pat. No. 5,725,871, issued Mar. 10, 1998
U.S. Pat. No. 5,739,119, issued Apr. 14, 1998
U.S. Pat. No. 5,741,516, issued Apr. 21, 1998
U.S. Pat. No. 5,747,470, issued May 5, 1998
U.S. Pat. No. 5,756,353, issued May 26, 1998
U.S. Pat. No. 5,759,829, issued Jun. 2, 1998
U.S. Pat. No. 5,770,219, issued Jun. 23, 1998
U.S. Pat. No. 5,779,708, issued Jul. 14, 1998
U.S. Pat. No. 5,780,045, issued Jul. 14, 1998
U.S. Pat. No. 5,783,208, issued Jul. 21, 1998
U.S. Pat. No. 5,783,683, issued Jul. 21, 1998
U.S. Pat. No. 5,789,573, issued Aug. 4, 1998
U.S. Pat. No. 5,792,451, issued Aug. 11, 1998
U.S. Pat. No. 5,797,898, issued Aug. 25, 1998
U.S. Pat. No. 5,801,154, issued Sep. 1, 1998
U.S. Pat. No. 5,804,212, issued Sep. 8, 1998

Aguilera, Hope, Sakano, "Characterization of immunoglobulin enhancer deletions in murine plasmacytomas," *EMBO J.*, 4:3689–3693, 1985.

Aizawa, Nakano, Ishida, Horie, Nagai, Ito, Yagita, Okumura, Inoue, Watanabe, "Tumor necrosis factor receptor-associated factor (TRAF) 5 and TRAF2 are involved in CD30-mediated NFkappaB activation," *J. Biol Chem.*, 272, 2042–2045, 1997.

Akifusa, Ohguchi, Koseki, Nara, Semba, Yamato, Okahashi, Merino, Nunez, Hanada, Takehara, Nishihara, "Increase in Bcl-2 level promoted by CD40 ligation correlates with inhibition of B cell apoptosis induced by vacuolar type H(+)- ATPase inhibitor," *Exp. Cell Res.*, 238:82–89, 1998.

Alderson, Armitage, Tough, Strockbine, Fanslow, Spriggs, "CD40 expression by human monocytes: regulation by cytokines and activation of monocytes by the ligand for CD40," *J. Exp. Med.,*. 178:669–674, 1993.

Allen and Choun, "Large unilamellar liposomes with low uptake into the reticuloendothelial system," *FEBS Lett.*, 223:42–46, 1987.

Altschul, Gish, Miller, Myers, Lipman, "Basic local alignment search tool," *J. Mol. Biol.*, 215:403–10, 1990.

Aran, Gottesman, Pastan, "Construction and characterization of bicistronic retroviral vectors encoding the multidrug transporter and betagalactosidase or green fluourescent protein" *Cancer Gene Ther.* 5(4): 195–206, 1998.

Armitage, Fanslow, Strockbine, Sato, Clifford, Macduff, Anderson, Gimpel, Davis-Smith, Maliszewski, et al., "Molecular and biological characterization of a murine ligand for CD40," *Nature*, 357:80–82, 1992.

Armitage, Koch, Frydenlund, Orum, Batz, Schuster, "Peptide nucleic acid-anthraquinone conjugates: strand invasion and photoinduced cleavage of duplex DNA," *Nucl. Acids Res.*, 25(22):4674–4678, 1997.

Armitage, Ly, Koch, Frydenlund, Orum, Batz, Schuster, "Peptide nucleic acid-DNA duplexes: long range hole migration from an internally linked anthraquinone," *Proc. Natl. Acad. Sci. USA*, 94(23):12320–12325, 1997.

Ausubel, Brent, Kingston, Moore, Seidman, Smith, Struhl, In: *Current Protocols in Molecular Biology*, John Wiley and Sons, New York, 1987.

Avrameas, Ternynck, Nato, Buttin, Avrameas, "Polyreactive anti-DNA monoclonal antibodies and a derived peptide as vectors for the intracytoplasmic and intranuclear translocation of macromolecules" *Proc. Natl. Acad. Sci. U.S.A.*, 95(10):5601–6, 1998.

Babu, "A convenient phenotype for DNase-Mutant," *Worm Breeder's Gazette*, 1:10, 1988.

Baker, Baron, Henzel, Spencer, "Molecular cloning and characterization of human and murine DNase II," *Gene*, 215:281–289, 1998.

Balazsovits et al., "Analysis of the effect of liposome encapsulation on the vesicant properties, acute and cardiac toxicities, and antitumor efficacy of doxorubicin," *Cancer Chemother. Pharmacol.*, 23:81–86, 1989.

Ballantyne, Henry, Marcu, "Antibody class switch recombinase activity is B cell stage specific and functions stochastically in the absence of 'targeted accessibility' control," *Int. Immunol.*, 9:963–974, 1997.

Ballantyne, Ozsvath, Bondarchuk, Marcu, "Chromosomally integrated retroviral substrates are sensitive indicators of an antibody class switch recombinase-like activity," *Curr. Top. Microbiol. Immunol,*. 194:439–448, 1995.

Barnes, Lindahl, Sedgwick, "DNA repair," *Curr. Opin. Cell Biol.*, 5:424–433, 1993.

Barry and Eastman, "Endonuclease activation during apoptosis: the role of cytosolic Ca2+ and pH," *Biochem. Biophys. Res. Commun.*, 186:782–789, 1992.

Barry, Reynolds, Eastman,. "Etoposide-induced apoptosis in human HL-60 cells is associated with intracellular acidification," *Cancer Res.* 53:2349–2357, 1993.

Berberich, Shu, Clark, "Cross-linking CD40 on B cells rapidly activates nuclear factor-kappa B," *J. Immunol.*, 153:4357–4366, 1994.

Bergsagel, Chesi, Nardini, Brents, Kirby, Kuehl, "Promiscuous translocations into immunoglobulin heavy chain switch regions in multiple myeloma," *Proc. Natl. Acad. Sci. USA*, 93:13931–13936, 1996.

Bernard, Cory, Gerondakis, Webb, Adams, "Sequence of the murine and human cellular myc oncogenes and two modes of myc transcription resulting from chromosome translocation in B lymphoid tumours," *Eur. Molec. Biol. Org. J.*, 2:2375–2383, 1983.

Berton and Vitetta, "Interleukin 4 induces changes in the chromatin structure of the gamma 1 switch region in resting B cells before switch recombination," *J. Exp. Med.*, 172:375–378, 1990.

Blank, Clark, Wiegand, Luster, "Pertussis toxin inhibition of anti-immunoglobulin-stimulated proliferation and inositol phosphate formation," *Toxicol. Appl. Pharmacol*, 106:278–286, 1990.

Blattner and Tucker, "The Mol. biology of immunoglobulin D.," *Nature*, 307:417–422, 1984.

Boffa, "Thrombomodulin in human brain microvasculature," *Lupus*, 4(2):165–166, 1995.

Boffa, Berard, Sugi, McIntyre, "Antiphosphatidylethanolamine antibodies as the only antiphospholipid antibodies detected by ELISA.II. Kininogen reactivity," *J. Rheumatol.*, 23(8):1375–1379, 1996.

Bottaro, Lansford, Xu, Zhang, Rothman, Alt, "S region transcription per se promotes basal IgE class switch recombination but additional factors regulate the efficiency of the process," *EMBO J.*, 13:665–674, 1994.

Bourlais, Acar, Zia, Sado, Needham, Leverge, "Ophthalmic drug delivery systems—recent advances," *Prog. Retin Eye Res.*, 17(1):33–58, 1998.

Briere, Servet-Delprat, Bridon, Saint-Remy, Banchereau, "Human interleukin 10 induces naive surface immunoglobulin D+ (sIgD+) B cells to secrete IgG1 and IgG3," *J. Exp. Med.*, 179:757–762, 1994.

Brown, Miranda, Galic, Hartman, Lyon, Aguilera, "Regulation of the RAG-1 promoter by the NF-Y transcription factor," *J. Immunol.*, 158:5071–5074, 1997.

Butler and Brown, "The immunoglobulins and immunoglobulin genes of swine," *Vet. Immunol. Immunopathol.*, 43:5–12, 1994.

Caldovic and Hackett Jr., "Development of position-independent expression vectors and their transfer into transgenic fish," *Mol. Mar. Biol. Biotechnol.*, 4(1):51–61, 1995.

Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.

Capecchi, "Altering the genome by homologous recombination," *Science*, 244:1288–1292, 1989.

Capecchi, M. R., "High efficiency transformation by direct microinjection of DNA into cultured mammalian cells," *Cell* 22(2):479–488, 1980.

Carlsson, Sandler, Jansson, "Influence of the neurotoxin capsaicin on rat pancreatic islets in culture, and on the pancreatic islet blood flow of rats," *Eur. J. Pharmacol.*, 312(1):75–81, 1996.

Carver, Dalrymple, Wright, Cottom, Reeves, Gibson, Keenan, Barrass, Scott, Colman, et al., "Transgenic livestock as bioreactors: stable expression of human alpha-1-antitrypsin by a flock of sheep," *Biotechnology NY*, 11(11):1263–1270, 1993.

Castelli, *In: DNA Damage and Repair*, Plenum Press, New York, N.Y., 1989.

Castigli, Alt, Davidson, Bottaro, Mizoguchi, Bhan, Geha, "CD40-deficient mice generated by recombination-activating gene-2-deficient blastocyst complementation," *Proc. Natl. Acad. Sci. USA.*, 91:12135–12139, 1994.

Chandran, Roy, Mishra, "Recent trends in drug delivery systems: liposomal drug delivery system—preparation and characterisation," *Indian J. Exp. Biol.*, 35(8):801–809, 1997.

Charron, Malynn, Robertson, Goff, Alt, "High-frequency disruption of the N-myc gene in embryonic stem and pre-B cell lines by homologous recombination," *Mol. Cell Biol.*, 10:1799–1804, 1990.

Chen and Okayama, "High-efficiency transformation of mammalian cells by plasmid DNA," *Mol. Cell. Biol.*, 7:2745–2752, 1987.

Chesi, Bergsagel, Brents, Smith, Gerhard, Kuehl, "Dysregulation of cyclin D1 by translocation into an IgH gamma switch region in two multiple myeloma cell lines," *Blood*, 88:674–681, 1996.

Choi, Boise, Gottschalk, Quintans, Thompson, Klaus, "The role of bcl-XL in CD40-mediated rescue from anti-mu-induced apoptosis in WEHI-231 B lymphoma cells," *Eur. J. Immunol.*, 25:1352–1357, 1995.

Chou and Morrison, "A common sequence motif near non-homologous recombination breakpoints involving Ig sequences," *J. Immunol.*, 150:5350–5360, 1993.

Christensen, Johansen, Marker, Thomsen, "Circulating intracellular adhesion molecule-1 (ICAM-1) as an early and sensitive marker for virus-induced T cell activation," *Clin. Exp. Immunol.*, 102(2):268–273, 1995.

Chu, Paul, Max, "Quantitation of immunoglobulin mu-gamma 1 heavy chain switch region recombination by a digestion-circularization polymerase chain reaction method," *Proc. Natl. Acad. Sci. USA.*, 89:6978–6982, 1992.

Clark and Ledbetter, "Activation of human B cells mediated through two distinct cell surface differentiation antigens, Bp35 and Bp50," *Proc. Natl. Acad. Sci. USA*, 83:4494–4498, 1986.

Cohen, "Designing antisense oligonucleotides as pharmaceutical agents," *Trends Pharmacol Sci.*, 10(11):435–7, 1989.

Coligan, Kruisbeek, Margulies, Shevach, Strober, (eds.), *In: Current Protocols in Immunology*, John Wiley and Sons, New York, 1991.

Collins and Olive, *Biochem.*, 32:2795–2799, 1993.

Collins, Furlong, Malde, Ascaso, Oliver, Lopez Rivas, "An apoptotic endonuclease activated either by decreasing pH or by increasing calcium," *J. Cell Sci.*, 109:2393–2399, 1996.

Collins, Harmon, Souvlis, Pope, Kerr, "Effects of cycloheximide on B-chronic lymphocytic leukaemic and normal lymphocytes in vitro: induction of apoptosis. Br.," *J. Cancer*, 64:518–522, 1991.

Corey, "Peptide nucleic acids: expanding the scope of nucleic acid recognition," *Trends Biotechnol.*, 15(6):224–229, 1997.

Cote and Ruiz-Carrillo, "Recognition of (dG)n.(dC)n sequences by endonuclease G. Characterization of the calf thymus nuclease," *J. Biol. Chem.*, 264:3301–3310, 1989.

Coune, "Liposomes as drug delivery system in the treatment of infectious diseases: potential applications and clinical experience," *Infection*, 16(3):141–147, 1988.

Couvreur et al., "Nanocapsules, a new lysosomotropic carrier," *FEBS Lett.*, 84:323–326, 1977.

Couvreur et al., "Tissue distribution of antitumor drugs associated with polyalkylcyanoacrylate nanoparticles," *J. Pharm. Sci.*, 69(2):199–202, 1980.

Couvreur, "Polyalkyleyanoacrylates as colloidal drug carriers," *Crit. Rev. Ther. Drug Carrier Syst.*, 5:1–20, 1988.

Cozzi, Tucker, Langford, Pino-Chavez, Wright, O'Connell, Young, Lancaster, McLanghlin, Hunt, Bordin, White, "Characterization of pigs transgenic for human decay-accelerating factor," *Transplantation*, 64(10):1383–1392, 1997.

Cummings, King, Holden, Low, "Purification and characterization of the potent endonuclease in extracts of bovine heart mitochondria," *J. Biol. Chem.*, 262:2005–2015, 1987.

Curiel, D. T., Agarwal., S., Wagner, E., and Cotten, M., "Adenovirus enhancement of transferrin-polylysine-mediated gene delivery," *Proc. Natl. Acad. Sci. USA* 88(19):8850–8854, 1991.

Czene, Tiback, Harms-Ringdahl, "pH-dependent DNA cleavage in permeabilized human fibroblasts. Biochem.," *J.* 323:337–341, 1997.

Daniels and Lieber, "Strand specificity in the transcriptional targeting of recombination at immunoglobulin switch sequences," *Proc. Natl. Acad. Sci. USA*, 92:5625–5629, 1995.

Daniels, Lieber, "Transcription targets recombination at immunoglobulin switch sequences in a strand-specific manner," *Curr. Top. Microbiol. Immunol.* 217:171–189, 1996.

Davis, Calame, Early, Livant, Joho, Weissman, Hood, "An immunoglobulin heavy-chain gene is formed by at least two recombinational events," *Nature*, 283:733–739, 1980.

De Mesmaeker et al., "Antisense oligonucleotides," *Acc. Chem. Res.*, 28:366–374, 1995. de Vries and van Steeg, "XPA knockout mice, *Sem. Cancer Biol.*, 7:229–240, 1996.

Defrance, Vanbervliet, Briere, Durand, Rousset, Banchereau, "Interleukin 10 and transforming growth factor beta cooperate to induce anti-CD40-activated naive human B cells to secrete immunoglobulin A," *J. Exp. Med.*, 175:671–682, 1992.

Delphin and Stavnezer, "Characterization of an interleukin 4 (IL-4) responsive region in the immunoglobulin heavy chain germline epsilon promoter: regulation by NF-IL-4, a C/EBP family member and NF-kappa B/p50," *J. Exp. Med.*, 181:181–192, 1995.

Dignam, Lebovitz, "Accurate transcription initiation by RNA polymerase II in a soluble extract from isolated mammalian nuclei," *Nucl. Acids Res.*, 11:1475–1489, 1983.

Driscoll, "Cell death in *C. elegans*: Molecular insights into mechanisms conserved between nematodes and mammals," *Brain Pathol.*, 6:411–415, 1997.

Douglas, Davis, Illum, "Nanoparticles in drug delivery," *Crit. Rev. Ther. Drug Carrier Syst.*, 3(3):233–261, 1987.

Dunnick, Hertz, Scappino, Gritzrnacher, "DNA sequences at immunoglobulin switch region recombination sites," *Nucl. Acids Res.*, 21:365–372, 1993.

Dunnick, Wilson, Stavnezer, "Mutations, duplication, and deletion of recombined switch regions suggest a role for DNA replication in the immunoglobulin heavy-chain switch," *Mol. Cell Biol.*, 9:1850–1856, 1989.

Eastman, "Survival factors, intracellular signal transduction, and the activation of endonucleases in apoptosis," *Semin. Cancer Biol.*, 6:45–52, 1995.

Ebert, Selgrath, DiTullio, Denman, Smith, Memon, Schindler, Monastersky, Vitale, Gordon, "Transgenic production of a variant of human tissue-type plasminogen activator in goat milk: generation of transgenic goats and analysis of expression," *Biotechnology NY*, 9(9):835–838, 1991.

Egholm, Buchardt, Christensen, Behrens, Freier, Driver, Berg, Kim, Norden, Nielsen, "PNA hybridizes to complementary oligonucleotides obeying the Watson-Crick hydrogen-bonding rules," *Nature*, 365(6446):566–568, 1993.

Eglitis, M. A., and Anderson, W. F., "Retroviral vectors for introduction of genes into mammalian cells," *Biotechniques* 6(7):608–614, 1988.

Eglitis, M. A., Kantoff, P. W., Kohn, D. B., Karson, E., Moen, R. C., Lothrop, C. D., Blaese, R. M., and Anderson, W. F., "Retroviral-mediated gene transfer into hemopoietic cells," *Avd. Exp. Med. Biol.* 241:19–27, 1988.

Enari, Sakahira, Yokoyama, Okawa, Iwamatsu, Nagata, "A caspase-activated DNase that degrades DNA during apoptosis, and its inhibitor ICAD, *Nature*, 391:43–50, 1998.

Engelward, Dreslin, Christensen, Huszar, Kurahara, Samson, "Repair-deficient 3-methyladenine DNA glycosylase homozygous mutant mouse cells have increased sensitivity to alkylation-induced chromosome damage and cell killing," *EMBO J.*, 15:945–952, 1996.

Epstein and Shakes, (eds.), *In: Caenorhabditis elegans*: "Model Biological Analysis of an Organism," Academic Press, Inc. San Diego, Calif., 1995.

Erickson and Izant, (eds.), "In: Biology of antisense RNA and DNA," *Gene Regulation*, vol. 1, Raven Press, New York, N.Y., 1992.

Esser and Radbruch, "Immunoglobulin class switching: molecular and cellular analysis," *Annu. Rev. Immuno.*, 8:717–735, 1990.

Faller and Baltimore, "Liposome encapsulation of retrovirus allows efficient super infection of resistant cell lines," *J. Virol.*, 49(1):269–272, 1984.

Faris, Gaskin, Parsons, "CD40 signaling pathway: anti-CD40 monoclonal antibody induces rapid dephosphorylation and phosphorylation of tyrosine-phosphorylated proteins including protein tyrosine kinase Lyn, Fyn, and Syk and the appearance of a 28-kD tyrosine phosphorylated protein," *J. Exp. Med.*,. 179:1923–1931, 1994.

Fechheimer et al., "Transfection of mammalian cells with plasmid DNA by scrape loading and sonication loading," *Proc. Natl. Acad. Sci. USA*, 84:8463–8467, 1987.

Fehs, Schade, Li, Uhde, Koch, Goller, Ruger, Fehse, Stockschlader, Zander, "Highly-efficient gene transfer with retroviral vectors into human T lymphocytes on fibronectin," *Br. J. Haematol*, 102(2):566–74, 1998.

Fields and Casey, "Signalling functions and biochemical properties of pertussis toxin-resistant G-proteins," *Biochem. J.*, 321:561–571, 1997.

Fire, Xu, Montgomery, Kostas, Driver, Mello, "Potent and specific genetic interference by double-stranded RNA in Caenorhabditis elegans," *Nature*, 391:806–811, 1998.

Fischman, Lambert, Studzinski, "Purification and properties of a nuclear DNA endonuclease from HeLa S3 cells," *Biochem. Biophys Acta*, 567:464–471, 1979.

Footer, Egholm, Kron, Coull, Matsudaira, "Biochemical evidence that a D-loop is part of a four-stranded PNA-DNA bundle. Nickel-mediated cleavage of duplex DNA by a Gly-Gly-His bis-PNA," *Biochemistry*, 35(33):10673–10679, 1996.

Fraley et al., "Entrapment of a bacterial plasmid in phospholipid vesicles: Potential for gene transfer," *Proc. Natl. Acad. Sci. USA*, 76:3348–3352, 1979.

Franz, Mueller, Haartong, Frey, Katus, "Transgenic animal models: new avenues in cardiovascular physiology," *J. Mol. Med.*, 75(2):115–119, 1997.

Fresat and Puglisi, "Application of liposomes as potential cutaneous drug delivery systems. In vitro and in vivo investigation with radioactively labelled vesicles," *J. Drug Target*, 4(2):95–101, 1996.

Fromm, M., Taylor, L. P., and Walbot, V., "Expression of genes transferred into monocot and dicot plant cells by electroporation," *Proc. Natl. Acad. Sci. USA* 82(17):5824–5828, 1985.

Fukita, Mizuta, Shirozu, Ozawa, Shimizu, Honjo, "The human S mu bp-2, a DNA-binding protein specific to the single-stranded guanine-rich sequence related to the immunoglobulin mu chain switch region," *J. Biol. Chem.*, 268:17463–17470, 1993.

Gabizon and Papahadjopoulos, "Liposomes formulations with prolonged circulation time in blood and enhanced uptake by tumors," *Proc. Natl. Acad. Sci. USA*, 85:6949–6953, 1988.

Gaff, Grumont, Gerondakis, "Transcriptional regulation of the germline immunoglobulin C alpha and C epsilon genes: implications for commitment to an isotype switch," *Int. Immunol.*, 4:1145–1151, 1992.

Gaido and Cidlowski, "Identification, purification, and characterization of a calcium-dependent endonuclease (NUC18) from apoptotic rat thymocytes. NUC18 is not histone H2B," *J. Biol. Chem.*, 266:18580–18585, 1991.

Galy and Spits, "CD40 is functionally expressed on human thymic epithelial cells," *J. Immunol.*, 149:775–782, 1992.

Gambacorti-Passerini, Mologni, Bertazzoli, le Coutre, Marchesi, Grignani, Nielsen, "In vitro transcription and translation inhibition by anti-promyelocytic leukemia (PML)/retinoic acid receptor alpha and anti-PML peptide nucleic acid," *Blood*, 88(4):1411–1417, 1996.

Garcia-Bermejo, Perez, Vilaboa, de Blas, Aller, "cAMP increasing agents attenuate the generation of apoptosis by etoposide in promonocytic leukemia cells," *J. Cell Sci.*, 111:637–644, 1998.

Gefter et al., *Somatic Cell Genet.* 3:231–236, 1977.

Gerondakis, Cory, Adams, "Translocation of the myc cellular oncogene to the immunoglobulin heavy chain locus in murine plasmacytomas is an imprecise reciprocal exchange.," *Cell*, 36:973–982, 1984.

Gerondakis, Gaff, Goodman, Grumont, "Structure and expression of mouse germline immunoglobulin gamma 3 heavy chain transcripts induced by the mitogen lipopolysaccharide," *Immunogenetics*, 34:392–400, 1991.

Giulian, Moss, Greaser, "Improved methodology for analysis and quantitation of proteins," *Anal. Biochem.*, 129:277–87, 1983.

Goding, "Monoclonal Antibodies: Principles and Practice," pp. 60–74. 2nd Edition, Academic Press, Orlando, Fla., 1986.

Good and Nielsen, "Progress in developing PNA as a gene-targeted drug," *Antisense Nucl. Acid Drug Dev.*, 7(4):431–437, 1997.

Goodman, Gaff, Gerondakis, "The IL-4 induced increase in the frequency of resting murine splenic B cells expressing germline Ig heavy chain gamma 1 transcripts correlates with subsequent switching to IgG1," *Int. Immunol.*, 5:199–208, 1993.

Gopal, "Gene transfer method for transient gene expression, stable transfection, and cotransfection of suspension cell cultures," *Mol. Cell Biol.*, 5:1188–1190, 1985.

Gossen, Freundlieb, Bender, Muller, Hillen, Bujard, "Transcriptional activation by tetracyclines in mammalian cells," *Science*, 268:1766–1769, 1995.

Gottlieb and Dosanjh, "Mutant cystic fibrosis transmembrane conductance regulator inhibits acidification and apoptosis in C127 cells: possible relevance to cystic fibrosis," *Proc. Natl. Acad. Sci. USA.*, 93:3587–3591, 1996.

Gottlieb and Muzyczka, "Purification and characterization of HeLa endonuclease R. A G-specific mammalian endonuclease," *J. Biol. Chem.*, 265:10836–10841, 1990b.

Gottlieb and Muzyczka, "Substrate specificity of HeLa endonuclease R. A G-specific mammalian endonuclease," *J. Biol. Chem.*, 265:10842–10850, 1990a.

Gottlieb, Gruol, Zhu, Engler, "Preconditioning rabbit cardiomyocytes: role of pH, vacuolar proton ATPase, and apoptosis," *J. Clin. Invest.*, 97:2391–2398, 1996a.

Gottlieb, Nordberg, Skowronski, Babior, "Apoptosis induced in Jurkat cells by several agents is preceded by intracellular acidification," *Proc. NatL. Acad. Sci. USA*, 93:654–658, 1996b.

Graham and van der Eb, "Transformation of rat cells by DNA of human adenovirus 5," *Virology*, 54(2):536–539, 1973.

Gribskov, Burgess, Devereux, "PEPPLOT, a protein secondary structure analysis program for the UWGCG sequence analysis software package," *Nucleic Acids Res.*, 14(1):327–34, 1986.

Gyurko, Tran, Phillips, "Time course of inhibition of hypertension by antisense oligonucleotides targeted to $AT_1$ angiotensin receptor mRNA in spontaneously hypertensive rats," *Am. J. Hypertens.*, 10:565–625, 1997.

Gyurko, Wielbo, Phillips, "Antisense inhibition of $AT_1$ receptor mRNA and angiotensinogen mRNA in the brain of spontaneously hypertensive rats reduces hypertension of neurogenic origin," *Reg. Pep.*, 49(2):167–174, 1993.

Gu, Jin, Gao, Weaver, Alt, "Ku70-deficient embryonic stem cells have increased ionizing radiosensitivity, defective DNA end-binding activity, and inability to support V(D)J recombination," *Proc. Natl. Acad. Sci. USA*, 94:8076–8081, 1997.

Han, Zheng, Schatz, Spanopoulou, "Neoteny in lymphocytes: Rag1 and Rag2 expression in germinal center B cells," *Sci.*, 274:2094–2097, 1996.

Hanakahi, Dempsey, Li, Maizels, "Nucleolin is one component of the B cell-specific transcription factor and switch region binding protein, LR1," *Proc. Natl. Acad. Sci. USA.*, 94:3605–3610, 1997.

Hanissian and Geha, "Jak3 is associated with CD40 and is critical for CD40 induction of gene expression in B cells," *Immunity*, 6:379–387, 1997.

Hanvey, Peffer, Bisi, Thomson, Cadilla, Josey, Ricca, Hassman, Bonham, Au, et al., "Antisense and antigene properties of peptide nucleic acids," *Science*, 258(5087):1481–1485, 1992.

Hara, "The essential region of CD40 cytoplasmic domain for signal transduction in WEHI231 cells," *Hokkaido J. Med. Sci.*, 72:309–317, 1997.

Harland and Weintraub, "Translation of mammalian mRNA injected into Xenopus oocytes is specifically inhibited by antisense RNA," *J. Cell Biol.*, 101:1094–1099, 1985.

Harlow, E. and Lane, D. "Antibodies: A Laboratory Manual.," Cold Spring Harbor Laboratory, Cold Spring Harbor, N.Y., 1988.

Harriman, Volk, Defranoux, Wabl, "Immunoglobulin class switch recombination," *Annu. Rev. Immunol.*, 11:361–384, 1993.

Hart and McKenzie, "Isolation and characterization of human tonsil dendritic cells," *J. Exp. Med.*, 168:157–170, 1988.

Hashida, Tanaka, Matsunami, Yoshihara, Kamiya, Tanigawa, Koide, "Purification and properties of bull seminal plasma Ca2+,Mg2+-dependent endonuclease," *J. Biol. Chem.*, 257:13114–13119, 1982.

Haskell and Bowen, "Efficient production of transgenic cattle by retroviral infection of early embryos," *Mol. Reprod. Dev.*, 40(3):386–390, 1995.

Heath and Martin, "The development and application of protein-liposome conjugation techniques," *Chem. Phys. Lipids*, 40:347–358, 1986.

Heath et al., "Liposome-mediated delivery of pteridine antifolates to cells: in vitro potency of methotrexate and its alpha and gamma substituents," *Biochim. Biophys. Acta*, 862:72–80, 1986.

Hengartner, "Cell Death," In *C. elegans* II, Cold Spring Harbor Laboratory Press, Plainview, N.Y. (D. L. Riddle, T. Blumenthal., B. J. Meyer, and J. R. Priess, Eds.), p. 383–415, 1997.

Henry-Michelland et al., "Attachment of antibiotics to nanoparticles; Preparation, drug-release and antimicrobial activity in vitro, *Int. J. Pharm.*, 35:121–127, 1987.

Hevelone and Hartman, "An endonuclease from *Caenorhabditis elegans*: partial purification and characterization," *Biochem. Genet.*, 26:447–461, 1988.

Hewish and Burgoyne, "The calcium dependent endonuclease activity of isolated nuclear preparations. Relationship between its occurance and the occurance of other classes of enzymes found in nuclear preparations," *Biochem. Biophys. Res. Commun.*, 52:475–481, 1973.

Hibino, Yoneda, Sugano, "Purification and properties of a magnesium-dependent endodeoxyribonuclease endogenous to rat-liver nuclei," *Biochim Biophys. Acta*, 950(3):313–20, 1988.

Honjo and Kataoka, "Organization of immunoglobulin heavy chain genes and allelic deletion model," *Proc. Natl. Acad. Sci. USA*, 75:2140–2144, 1978.

Hope, Aguilera, Minie, Sakano, "Endonucleolytic activity that cleaves immunoglobulin recombination sequences," *Sci.*, 231:1141–1145, 1986.

Hu, O'Rourke, Boguski, Dixit, "A novel RING finger protein interacts with the cytoplasmic domain of CD40," *J. Biol. Chem.*, 269:30069–30072, 1994.

Hwang, Park, Park, "Gastric retentive drug-delivery systems," *Crit. Rev. Ther. Drug Carrier Syst.*, 15(3):243–284, 1998.

Hyrup and Nielsen, "Peptide nucleic acids (PNA): synthesis, properties and potential applications," *Bioorg. Med. Chem.*, 4(1):5–23, 1996.

Imaizumi et al., "Liposome-entrapped superoxide dismutase reduces cerebral infarction in cerebral ischemia in rats," *Stroke*, 21(9):1312–1317, 1990a.

Imaizumi et al., "Liposome-entrapped superoxide dismutase ameliorates infarct volume in focal cerebral ischemia," *Acta. Neurochirurgica Suppl.*, 51:236–238, 1990b.

Ishida, Akiyoshi, Takahashi, "Isolation and purification of calcium and magnesium dependent endonuclease from rat liver nuclei, *Biochem. Biophys. Res. Commun.*, 56:703–710, 1974.

Ishida, Mizushima, Azuma, Kobayashi, Tojo, Suzuki, Aizawa, Watanabe, Mosialos, Kieff et al., "Identification of TRAF6, a novel tumor necrosis factor receptor-associated factor protein that mediates signaling from an amino-terminal domain of the CD40 cytoplasmic region," *J. Biol. Chem.*, 271:28745–28748, 1996b.

Ishida, Tojo, Aoki, Kobayashi, Ohishi, Watanabe, Yamamoto, Inoue, "TRAF5, a novel tumor necrosis factor receptor-associated factor family protein, mediates CD40 signaling,+ *Proc. Natl. Acad. Sci. USA*, 93:9437–9442, 1996a.

Ishiguro, Ichihara, Namikawa, Nagatsu, Kurosawa, "Nucleotide sequence of *Suncus murinus* immunoglobulin mu gene and comparison with mouse and human mu genes," *FEBS Lett.*, 247:317–322, 1989.

Ishii, Etheridge, Gobe, "Cycloheximide-induced apoptosis in Burkitt lymphoma (BJA-B) cells with and without Epstein-Barr virus infection," *Immunol. Cell Biol.*, 73:463–468, 1995.

Itoh, Yonehara, Ishii, Yonehara, Mizushima, Sameshima, Hase, Seto, Nagata, "The polypeptide encoded by the cDNA for human cell surface antigen Fas can mediate apoptosis," *Cell*, 66:233–243, 1991.

Iwasato, Shimizu, Honjo, Yamagishi, "Circular DNA is excised by immunoglobulin class switch recombination, *Cell*, 62:143–149, 1990.

Jabara, Loh, Ramesh, Vercelli, Geha, "Sequential switching from mu to epsilon via gamma 4 in human B cells stimulated with IL-4 and hydrocortisone," *J. Immunol.*, 151:4528–4533, 1993.

Jack, McDowell, Steinberg, Wabl, "Looping out and deletion mechanism for the immunoglobulin heavy-chain class switch, *Proc. Natl. Acad. Sci. USA*, 85:1581–1585, 1988.

Jameson and Wolf, *Compu. Appl. Biosci.*, 4(1):181–6, 1988.

Janz, Muller, Shaughnessy, Potter, "Detection of recombinations between c-myc and immunoglobulin switch alpha in murine plasma cell tumors and preneoplastic lesions by polymerase chain reaction," *Proc. Natl. Acad. Sci. USA*, 90:7361–7365, 1993.

Jaskulski, deRiel, Mercer, Calabretta, Baserga, "Inhibition of cellular proliferation by antisense oligodeoxynucleotides to PCNA cyclin," *Science*, 240(4858):1544–1546, 1988.

Jensen and Pedersen, "Nocturnal blood pressure and relation to vasoactive hormones and renal function in hypertension and chronic renal failure," *Blood Press.*, 6(6):332–342, 1997.

Jessberger and Lieber, "Molecular analysis of DNA rearrangements in the immune system, *Curr. Top. Microbiol. Immunol.*, 217:1–220, 1996.

Jung, Rajewsky, Radbruch, "Shutdown of class switch recombination by deletion of a switch region control element, *Sci.*, 259:984–987, 1993.

Jung, Siebenkotten, Radbruch, "Frequency of immunoglobulin E class switching is autonomously determined and independent of prior switching to other classes, *J. Exp. Med.*, 179:2023–2026, 1994.

Kadowaki, Hayashi, Amakawa, Akasaka, Yabumoto, Ohno, Fukuhara, Okuma, "Class switch recombination of the immunoglobulin heavy chain gene frequently occurs in B-cell lymphomas associated with rearrangement of the BCL2 gene," *Int. J. Hematol.*, 61:69–75, 1995.

Kamesaki, Zwiebel, Reed, Cossman, "Role of bcl-2 and IL-5 in the regulation of anit-IgM-induced growth arrest and apoptosis in immature B cell lines," *J. Immunol.*, 152:3294–3305, 1994.

Kataoka, Kondo, Nishi, Kodaira, Honjo, "Isolation and characterization of endonuclease J: a sequence-specific endonuclease cleaving immunoglobulin genes," *Nucl. Acids Res.*," 12:5995–6010, 1984.

Kataoka, Miyata, Honjo, "Repetitive sequences in classswitch recombination regions of immunoglobulin heavy chain genes," *Cell*, 23:357–368, 1981.

Kawabe, Naka, Yoshida, Tanaka, Fujiwara, Suematsu, Yoshida, Kishimoto, Kikutani, "The immune responses in CD40-deficient mice: impaired immunoglobulin class switching and germinal center formation," *Immunit*, 1:167–178, 1994.

Kenter and Watson, "Cell cycle kinetics model of LPS-stimulated spleen cells correlates switch region rearrangements with S phase," *J. Immunol. Methods*, 97:111–117, 1987.

Kenter, Wuerffel, Sen, Jamieson, Merkulov, "Switch recombination breakpoints occur at nonrandom positions in the S gamma tandem repeat," *J. Immunol.*, 151:4718–4731, 1993.

Kitamura, Roes, Kuhn, Rajewsky, "A B cell-deficient mouse by targeted disruption of the membrane exon of the immunoglobulin mu chain gene," *Nature*, 350:423–426, 1991.

Klein, Wolf, Wu, Sanford, "High-velocity microprojectiles for delivering nucleic acids into living cells. 1987," *Biotechnology*, 24:384–386, 1992.

Knapp, Liu, Newell, Ward, Tucker, Strober, Blattner, "Simultaneous expression of immunoglobulin mu and delta heavy chains by a cloned B-cell lymphoma: a single copy of the VH gene is shared by two adjacent CH genes," *Proc. Natl. Acad. Sci. USA*, 79:2996–3000, 1982.

Knox and Gordon, "Protein tyrosine phosphorylation is mandatory for CD40-mediated rescue of germinal center B cells from apoptosis," *Eur. J. Immunol.*, 23:2578–2584, 1993.

Kohler and Milstein, *Eur. J. Immunol.* 6:511–519, 1976.

Kohler and Milstein, *Nature* 256:495–497, 1975.

Koizumi, Wang, Suzuki, Masuda, Watanabe, "Regulation of bcl-xL expression and Fas susceptibility in mouse B cells by CD40 ligation, surface IgM crosslinking and IL-4," *Mol. Immunol.*, 33:1247–1253, 1996.

Koppelhus, Zachar, Nielsen, Liu, Eugen-Olsen, Ebbesen, "Efficient in vitro inhibition of HIV-1 gag reverse transcription by peptide nucleic acid (PNA) at minimal ratios of PNA/RNA," *Nucl. Acids Res.*, 25(11):2167–2173.

Krowczynska, Rudders, Krontiris, "The human minisatellite consensus at breakpoints of oncogene translocations," *Nucl. Acids Res.*, 18:1121–1127, 1990.

Kuwabara, Kondo, Fukutomi, Fujii, Orii, "Methylation patterns of I epsilon region in B cells stimulated with interleukin 4 and Epstein-Barr virus in patients with a high level of serum IgE," *Eur. J. Immunogenet.*, 22:265–275, 1995.

Kyte and Doolittle, *J. Mol. Biol.*, 157:105–132, 1982.

Lasic, "Novel applications of liposomes," *Trends Biotechnol.*, 16(7):307–321, 1998.

Lepse, Kumar, Ganea, "Extrachromosomal eukaryotic DNA substrates for switch recombination: analysis of isotype and cell specificity," *DNA Cell Biol.*, 13:1151–1161, 1994.

Leung and Maizels, "Regulation and targeting of recombination in extrachromosomal substrates carrying immunoglobulin switch region sequences," *Mol. Cell. Biol.*, 14:1450–1458, 1994.

Leung and Maizels, "Transcriptional regulatory elements stimulate recombination in extrachromosomal substrates carrying immunoglobulin switch-region sequences." *Proc. Natl. Acad. Sci. USA*, 89:4154–4158, 1992.

Li and Eastman, "Apoptosis in an interleukin-2-dependent cytotoxic T lymphocyte cell line is associated with intracellular acidification, Role of the Na(+)/H(+)-antiport," *J. Biol. Chem.*, 270:3203–3211, 1995.

Li, Baccam, Waters, Pessin, Bishop, Koretzky, "CD40 ligation results in protein kinase C-independent activation of ERK and JNK in resting murine splenic B cells," *J. Immunol.*, 157:1440–1447, 1996c.

Li, Daniels, Lieber, "Asymmetric mutation around the recombination break point of immunoglobulin class switch sequences on extrachromosomal substrates," *Nucl. Acids Res.*, 24:2104–2111, 1996a.

Li, Otevrel,. Gao, Cheng, Seed, Stamato, Taccioli, Alt, "The XRCC4 gene encodes a novel protein involved in DNA double-strand break repair and V(D)J recombination," *Cell*, 83:1079–1089, 1995.

Li, Peakman, Golub, Reddy, Ward, Radding, Maizels, "Rad51 expression and localization in B cells carrying out class switch recombination," *Proc. Natl. Acad. Sci. USA*, 93:10222–10227, 1996b.

Liao, "The subunit structure and active site sequence of porcine spleen deoxyribonuclease," *J. Biol. Chem.*, 260:10708–10713, 1985.

Lin and Stavnezer, "Activation of NF-kappaB/Rel by CD40 engagement induces the mouse germ line immunoglobulin Cgamma1 promoter," *Mol. Cell. Biol.*, 16:4591–4603, 1996.

Lindahl, "Repair of intrinsic DNA lesions," *Mutat. Res.*, 238:305–311, 1990.

Loh, Jabara, Geha, "Disodium cromoglycate inhibits Sµ→Sε deletional switch recombination and IgE synthesis in human B cells," *J. Exp. Med.*, 180:663–671, 1994a.

Loh, Jabara, Ren, Fu, Geha, "Role of protein tyrosine kinases in CD40/interleukin-4-mediated isotype switching to IgE," *J. Allergy Clin. Immunol.* 94:784–792, 1994b.

Lopez-Berestein et al., "Liposomal amphotericin B for the treatment of systemic fungal infections in patients with cancer: a preliminary study" *J. Infect. Dis.*, 2151:704, 1985a.

Lopez-Berestein et al., "Protective effect of liposomal-amphotericin B against *C. albicans* infection in mice," *Cancer Drug Delivery*, 2:183, 1985b.

Low, Cummings, King, "The bovine mitochondrial endonuclease prefers a conserved sequence in the displacement loop region of mitochondrial DNA," *J. Biol. Chem.*, 262:16164–16170, 1987.

Lowsky, DeCoteau, Reitmair, Ichinohasama, Dong, Xu, Mak, Kadin, and Minden, "Defects of the mismatch repair gene MSH2 are implicated in the development of murine and human lymphoblastic lymphomas and are associated with the aberrant expression of rhombotin-2 (Lmo-2) and Tal-1 (SCL)," *Blood*, 89:2276–2282, 1997.

Lu, L., Xiao, M., Clapp, D. W., Li, Z. H., and Broxmeyer, H. E., "High efficiency retroviral mediated gene transducion tinto single isolated immature and replatable CD34 (3+) hematopoietic stem/progenitor cells from human umbilical cord blood," *J. Exp. Med.* 178(6):2089–2096, 1993.

Lundgren, Strom, Bergquist, Skog, Heiden, Stavnezer, Severinson, "Cell cycle regulation of immunoglobulin class switch recombination and germ-line transcription: potential role of Ets family members," *Eur. J. Immunol.*, 25:2042–2051, 1995.

Lyon and Aguilera, "Purification and characterization of the immunoglobulin switch sequence-specific endonuclease (Endo-SR) from bovine spleen," *Molecular Imumunology*, 34:209–219, 1997.

Lyon, Harrington, Aguilera, "Cloning and characterization of the Endo-SR/DNase II gene," Submitted, XX:XX-XX, 1998.

Lyon, Miranda, Piao, Aguilera, "Characterization of an endonuclease activity which preferentially cleaves the G-rich immunoglobulin switch repeat sequences," *Mol. Immunol.*, 33:157–169, 1996.

Maki, Roeder, Traunecker, Sidman, Wabl, Raschke, Tonegawa, "The role of DNA rearrangement and alternative RNA processing in the expression of immunoglobulin delta genes," *Cell*, 24:353–365, 1981.

Malisan, Briere, Bridon, Harindranath, Mills, Max, Banchereau, Martinez-Valdez, "Interleukin-10 induces immunoglobulin G isotype switch recombination in human CD40-activated naive B lymphocytes," *J. Exp. Med.*, 183:937–947, 1996.

Maloy et al., "Microbial Genetics" 2nd Edition. Jones and Barlett Publishers, Boston, Mass., 1994.

Mandler, Chu, Paul, Max, Snapper, "Interleukin 5 induces S mu-S gamma 1 DNA rearrangement in B cells activated with dextran-anti-IgD antibodies and interleukin 4: a three component model for Ig class switching," *J. Exp. Med.*, 178:1577–1586, 1993a.

Mandler, Finkelman, Levine, Snapper, "IL-4 induction of IgE class switching by lipopolysaccharide-activated murine B cells occurs predominantly through sequential switching," *J. Immunol.*, 150:407–418, 1993b.

Marcu, Xu L, Kim, "S alpha BP/BSAP/NF-S mu B1, a murine and human B cell stage specific nuclear factor with DNA binding specificity implying roles in switch-recombination and transcription," *Curr. Top. Microbiol. Immunol.*, 182:167–174, 1992.

Marcu, Xu, Kim, "S alpha BP/BSAP/NF-S mu B1, a murine and human B cell stage specific nuclear factor with DNA binding specificity implying roles in switch-recombination and transcription," *Curr. Top. Microbiol. Immunol.*, 182:167–174, 1992.

Margalit, "Liposome-mediated drug targeting in topical and regional therapies," *Crit. Rev. Ther. Drug Carrier Syst.*, 12(2–3):233–261, 1995.

Mathiowitz, Jacob, Jong, Carino, Chickering, Chaturvedi, Santos, Vijayaraghavan, Montgomery, Bassett, Morrell, "Biologically erodable microspheres as potential oral drug delivery systems," *Nature*, 386(6623):410–414, 1997.

Matsuoka, Yoshida, Maeda, Usuda, Sakano, "Switch circular DNA formed in cytokine-treated mouse splenocytes: evidence for intramolecular DNA deletion in immunoglobulin class switching," *Cell*, 62:135–142, 1990.

Mayumi, Ishigami, Kanazashi, Yamaoka, Sumimoto, Heike, Katamura, Hata, Kim, "Positive and negative signals transduced through surface immunoglobulins in human B cells," *J. Allergy Clin. Immunol.*, 94:612–619, 1994.

McKenna, Maio, Brown, "Purification and properties of a mammalian endonuclease showing site-specific cleavage of DNA," *J. Biol. Chem.*, 256:6435–6443, 1981.

Meisenholder, Martin, Green, Nordberg, Babior, Gottlieb, "Events in apoptosis. Acidification is downstream of protease activation and BCL-2 protection," *J. Biol. Chem.*, 271:16260–16262, 1996.

Melamed, Wang, Roifinan, "Antigen receptor-mediated protein tyrosine kinase activity is regulated by a pertussis toxin-sensitive G protein," *J. Immunol.*, 149:169–174, 1992.

Mello, Kramer, Stinchcomb, Ambros, "Efficient gene transfer in C.elegans: extrachromosomal maintenance and integration of transforming sequences," *EMBO J.*, 10:3959–3970, 1991.

Meng, Wielbo, Gyurko, Phillips, "$AT_1$ receptor mRNA antisense oligonucleotide inhibits central angiotensin induced thirst and vasopressin," *Reg. Pep.*, 54:543–551, 1994.

Michaelson, Singh, Snapper, Sha, Baltimore, Birshtein, "Regulation of 3' IgH enhancers by a common set of factors, including κB-binding proteins," *J. Immunol.* 156:2828–2839, 1996.

Mills, Brooker, Camerini-Otero, "Sequences of human immunoglobulin switch regions: implications for recombination and transcription," *Nucl. Acids Res.*, 18:7305–7316, 1990.

Mills, Mitchell, Harindranath, Max, "Human Ig S gamma regions and their participation in sequential switching to IgE," *J. Immunol.*, 155:3021–3036, 1995.

Miranda, Chokler, Aguilera, "The murine nucleolin protein is an inducible DNA and ATP binding protein which is readily detected in nuclear extracts of lipopolysaccharide-treated splenocytes," *Exp. Cell Res.*, 217:294–308, 1995.

Mizuta, Fukita, Miyoshi, Shimizu, Honjo, "Isolation of cDNA encoding a binding protein specific to 5'-phosphorylated single-stranded DNA with G-rich sequences," *Nucl. Acids Res.*, 21:1761–1766, 1993.

Mollegaard, Buchardt, Egholm, Nielsen, "Peptide nucleic acid.DNA strand displacement loops as artificial transcription promoters," *Proc. Natl. Acad. Sci. USA*, 91(9):3892–3895, 1994.

Mond, Lees, Snapper, "T cell-independent antigens type 2," *Annu. Rev. Immunol.*, 13:655–692, 1995.

Montague, Gaido, Frye, Cidlowski, "A calcium-dependent nuclease from apoptotic rat thymocytes is homologous with cyclophilin. Recombinant cyclophilins A, B, and C have nuclease activity," *J. Biol. Chem.*, 269:18877–18880, 1994.

Moore, Boswell, Hoffman, Burgess, Hromas, "Mutant H-ras over-expression inhibits a random apoptotic nuclease in myeloid leukemia cells," *Leuk. Res.*, 17:703–709, 1993.

Morana, Wolf, Li, Reynolds, Brown, Eastman, "The involvement of protein phosphatases in the activation of ICE/CED-3 protease, intracellular acidification, DNA digestion, and apoptosis," *J. Biol. Chem.*, 271:18263–18271, 1996.

Mori and Fukatsu, "Anticonvulsant effect of DN-1417 a derivative of thyrotropin-releasing hormone and liposome-entrapped DN-1417 on amygdaloid-kindled rats," *Epilepsia*, 33(6):994–1000, 1992.

Morozov, Falzon, Anderson, Kuff, "DNA-dependent protein kinase is activated by nicks and larger single-stranded gaps," *J. Biol. Chem.*, 269:16684–16688, 1994.

Morris et al., "A new peptide vector for effcient delivery of oligonucleotides into mamalain cell," *Nucleic Acids Res.*, 25(14):2730–2736, 1997.

Mortensen, Conner, Chao, Geisterfer-Lowrance, Seidman, "Production of homozygous mutant ES cells with a single targeting construct," *Mol. Cell Biol.*, 1992:2391–2395, 1992.

Mowatt and Dunnick, "DNA sequence of the murine gammal switch segment reveals novel structural elements," *J. Immunol.*, 136:2674–2683, 1986.

Muller et al., "Efficient transfection and expression of heterologous genes in PC12 cells," *Cell, Biol.*, 9(3):221–229, 1990.

Nakamura, Sakaki, Watanabe, Takagi, "Purification and characterization of the Ca2+ plus Mg2+-dependent endodeoxyribonuclease from calf thymus chromatin," *J. Biochem.*, (Tokyo), 89:143–152, 1981.

Nakamura, Ogawa, Tsunematsu, "Characterization of monoclonal nonspecific suppressor factor (MNSF) with the use of a monoclonal antibody," *J. Immunol.*, 138(6):1799–803, 1987.

Nicolas and Rubenstein, "Retroviral vectors," *Biotechnology*, 10:493–513, 1988.

Nicolas and Rubinstein, "Retroviral vectors," *In: Vectors: A survey of molecular cloning vectors and their uses*, Rodriguez and Denhardt (eds.), Stoneharn: Butterworth, pp. 494–513, 1988.

Nicolau and Gersonde, "Incorporation of inositol hexaphosphate into intact red blood cells, I. fusion of effector-containing lipid vesicles with erythrocytes," *Naturwissenschaften* (Germany), 66(11):563–566, 1979.

Nicolau and Sene, "Liposome-mediated DNA transfer in eukaryotic cells," *Biochem. Biophys. Acta*, 721:185–190, 1982.

Nielsen, DiGiovanni, Christensen, Knepper, Harris, "Cellular and subcellular immunolocalization of vasopressin-regulated water channel in rat kidney," *Proc. Natl. Acad. Sci. USA*, 90(24):11663–11667, 1993.

Nikaido, Nakai, Honjo, "Switch region of immunoglobulin Cmu gene is composed of simple tandem repetitive sequences," *Nature*, 292:845–848, 1981.

Nikaido, Yamawaki-Kataoka, Honjo, "Nucleotide sequences of switch regions of immunoglobulin C epsilon and C gamma genes and their comparison," *J. Biol. Chem.*, 257:7322–7329, 1982.

Norton, Piatyszek, Wright, Shay, Corey, "Inhibition of human telomerase activity by peptide nucleic acids," *Nat. Biotechnol.*, 14(5):615–619, 1996.

Norton, Waggenspack, Varnum, Corey, "Targeting peptide nucleic acid-protein conjugates to structural features within duplex DNA," *Bioorg. Med. Chem.*, 3(4):437–445, 1995.

Nossal, "Negative selection of lymphocytes," *Cell*, 76:229–239, 1994.

Obata, Kataoka, Nakai, Yamagishi, Takahashi, Yamawaki-Kataoka, Nikaido, Shimizu, Honjo, "Structure of a rearranged gamma 1 chain gene and its implication to immunoglobulin class-switch mechanism," *Proc. Natl. Acad. Sci. USA*, 78:2437–2441, 1981.

Oettinger, "Cutting apart V(D)J recombination," *Curr. Opin. Gen. Dev.*, 6:141–145, 1996.

Ohno, Migita, Murakami, "c-myc gene in a murine plasmocytoma without visible chromosomal translocations moves to chromosome 12F1 with Pvt-1 and rearranges with IgH enhancer-S mu sequences," *Int. J. Cancer*, 49:102–108, 1991.

Ono, Hirose, Miyazaki, Yamamoto, Matsumoto, "Transgenic medaka fish bearing the mouse tyrosinase gene: expression and transmission of the transgene following electroporation of the orange-colored variant," *Pigment Cell Res.*, 10(3):168–175, 1997.

Orum, Nielsen, Jorgensen, Larrson, Stanley, Koch, "Sequence-specific purification of nucleic acids by PNA-controlled hybrid selection," *Biotechniques*, 19(3):472–480, 1995.

Ott and Marcu, "Mol. requirements for immunoglobulin heavy chain constant region gene switch-recombination revealed with switch-substrate retroviruses," *Int. Immunol.* 1:582–591, 1989.

Ott, Alt, Marcu, "Immunoglobulin heavy chain switch region recombination within a retroviral vector in murine pre-B cells," *EMBO J.*, 6:577–584, 1987.

Owens Jr., Finkelman, Mountz, Mushinski, "Nonhomologous recombination at sites within the mouse JH-C delta locus accompanies C mu deletion and switch to immunoglobulin D secretion," *Mol. Cell. Biol.*, 11:5660–5670, 1991.

Paillard and Strauss, "Analysis of the mechanism of interaction of simian Ku protein with DNA," *Nuc. Acids Res.*, 19:5619–5624, 1991.

Park, Makepeace, Lyons, Song, "Effect of intracellular acidity and ionomycin on apoptosis in HL-60 cells," *Eur. J. Cancer*, 32A:540–546, 1996.

Paulie, Ehlin-Henriksson, Mellstedt, Koho, Ben-Aissa, Perlmann, "A p50 surface antigen restricted to human urinary bladder carcinomas and B lymphocytes," *Cancer Immunol., Immunother.*, 20:23–28, 1985.

Perez-Sala, Collado-Escobar, Mollinedo, "Intracellular alkalinization suppresses lovastatin-induced apoptosis in HL-60 cells through the inactivation of a pH-dependent endonuclease," *J. Biol. Chem.*, 1995:6235–6242, 1995.

Peris, Jung, Resnick, Walker, Malakhova, Bokrand, Wielbo, "Antisense inhibition of striatal $GABA_A$ receptor proteins decreases GABA-stimulated chloride uptake and increases cocaine sensitivity in rats," *Mol. Brain Res.*, 57:310–312, 1998.

Perry-O'Keefe, Yao, Coull, Fuchs, Egholm, "Peptide nucleic acid pre-gel hybridization:
an alternative to southern hybridization," *Proc. Natl. Acad. Sci. USA*, 93(25):14670–14675, 1996.

Petrini and Dunnick, "Products and implied mechanism of H chain switch recombination," *J. Immunol.*, 142:2932–2935, 1989.

Petrini and Dunnick, "Products and implied mechanism of H chain switch recombination," *J. Immunol.*, 142:2932–2935, 1989.

Phillips, "Antisense inhibition and adeno-associated viral vector delivery for reducing hypertension," *Hypertension*, 29(2):177–187, 1997.

Phillips and Gyurko, "Antisense oligonucleotides: New tools for physiology," *News Physiol. Sci.*, 12:99–105, 1997.

Phillips, Wielbo, Gyurko, "Anitsense inhibiiton of hypertension: a new strategy for renin-angiotensin candidate genes," *Kidney International.*, 46:1554–1556, 1994.

Pikul et al., "In vitro killing of melanoma by liposome-delivered intracellular irradiation, *Arch. Surg.*, 122(12):1417–1420, 1987.

Pinto-Alphandary, Balland, Couvreur, "A new method to isolate polyalkylcyanoacrylate nanoparticle preparations," *J. Drug Target*, 3(2):167–169, 1995.

Pinto-Sietsma and Paul, "Transgenic rats as models for hypertension," *J. Hum. Hypertens.*, 11(9):577–581, 1997.

Potter et al., "Enhancer-dependent expression of human κ immunoglobulin genes introduced into mouse pre-B lymphocytes by electroporation," *Proc. Natl. Acad. Sci. USA*, 81:7161–7165, 1984.

Prokop and Bajpai, *Ann. N.Y. Acad. Sci.*, Vol. 646, 1991.

Purkerson and Isakson, "A two-signal model for regulation of immunoglobulin isotype switching," *FASEB J.*, 6:3245–3252, 1992.

Purkerson and Isakson, "Interleukin 5 (IL-5) provides a signal that is required in addition to IL-4 for isotype switching to immunoglobulin (Ig) G1 and IgE," *J. Exp. Med.*, 175:973–982, 1992b.

Quintanar-Guerrero, Allemann, Doelker, Fessi, "Preparation and characterization of nanocapsules from preformed polymers by a new process based on emulsification-diffusion techinque," *Phamr. Res.*, 15(7):1056–1062, 1998.

Ramirez, Carracedo, Zamzami, Castedo, Kroemer, "Pertussis toxin inhibits activation-induced cell death of human thymocytes, pre-B leukemia cells and monocytes," *J. Exp. Med.*, 180:1147–1152, 1994.

Ramsden, van Gent, Gellert, "Specificity in V(D)J recombination: new lessons from biochemistry and genetics," *Curr. Op. Immunol.*, 9:114–120, 1997.

Rebollo, Gomez, Martinez de Aragon, Lastres, Silva, Perez-Sala, "Apoptosis induced by IL-2 withdrawal is associated with an intracellular acidification," *Exp. Cell Res.*, 218:581–585, 1995.

Reitmair, Schmits, Ewel, Bapat, Redston, Mitri, Waterhouse, Mittucker, Wakeham, Liu et al., "MSH2 deficient mice are viable and susceptible to lymphoid tumors," *Nature Genetics*, 11:64–70, 1995.

Ren, Morio, Fu, Geha, "Signal transduction via CD40 involves activation of lyn kinase and phosphatidylinositol-3-kinase, and phosphorylation of phospholipase C gamma 2," *J. Exp. Med.*, 179:673–680, 1994b.

Renneisen et al., "Inhibition of expression of human immunodeficiency virus-1 in vitro by antibody-targeted liposomes containing antisense RNA to the env region," *J. Biol. Chem.*, 265(27):16337–16342, 1990.

Reynolds, Li, Craig, Eastman, "BCL-2 and MCL-1 expression in Chinese hamster ovary cells inhibits intracellular acidification and apoptosis induced by staurosporine," *Exp. Cell Res.*, 225:430–436, 1996.

Ribeiro and Carson, "$Ca^{2+}/Mg^{(2+)}$-dependent endonuclease from human spleen: purification, properties, and role in apoptosis," *Biochem.*, 32:9129–9136, 1993.

Riddle, Blumenthal., Meyer, Priess, (eds.), *In: C. elegans II.*, Cold Spring Harbor Laboratory Press, Plainview, N.Y., 1997.

Ridgway, "Mammalian expression vectors", *Biotechnology*, 10:467–92, 1988.

Ridgway, "Mammalian expression vectors," *In: Vectors: A survey of molecular cloning vectors and their uses*, Rodriguez R L, Denhardt D T, ed., Stoneham: Butterworth, pp. 467–492, 1988.

Rippe et al., "DNA-mediated gene transfer into adult rat hepatocytes in primary culture," *Mol. Cell Biol.*, 10:689–695, 1990.

Roest, van Klaveren, de Wit, van Gurp, Koken, Vermey, van Roijen, Hoogerbrugge, Vreeburg, Baarends, et al., "Inactivation of the HR6B ubiquitin-conjugating DNA repair enzyme in mice causes male sterility associated with chromatin modification," *Cell*, 86:799–810, 1996.

Rolink, Melchers, Andersson, "The SCID but not the RAG-2 gene product is required for S mu-S epsilon heavy chain class switching," *Immunity*, 5:319–330, 1996.

Roth and Wilson, "Nonhomologous recombination in mammalian cells: role for short sequence homologies in the joining reaction," *Mol. Cell. Biol.*, 6:4295–4304, 1986.

Rothman, Chen, Lutzker, Li, Stewart, Coffman, Alt, "Structure and expression of germ line immunoglobulin heavy-chain epsilon transcripts: interleukin-4 plus lipopolysaccharide-directed switching to C epsilon," *Mol. Cell Biol.*, 10:1672–1679, 1990.

Ruiz-Carrillo and Renaud, "Endonuclease G: a (dG)n X (dC)n-specific DNase from higher eukaryotes," *EMBO J.*, 6:401:407, 1987.

Sakano, Maki, Kurosawa, Roeder, Tonegawa, "Two types of somatic recombination are necessary for the generation of complete immunoglobulin heavy-chain genes," *Nature*, 286:676–683, 1980.

Sakumi, Shiraishi, Shimizu, Tsuzuki, Ishikawa, Sekiguchi, "Methylnitrosourea-induced tumorigenesis in MGMT gene knockout mice," *Cancer Res.*, 57:2415–2418, 1997.

Sambrook et al., "Molecular Cloning: A Laboratory Manual," Cold Spring Harbor Laboratory, Cold Spring Harbor, N.Y., 1989.

Sarma, Lin, Clark, Rust, Tewari, Noelle, Dixit, "Activation of the B-cell surface receptor CD40 induces A20, a novel zinc finger protein that inhibits apoptosis," *J. Biol. Chem.*, 270:12343–12346, 1995.

Schriever, Freedman, Freeman, Messner, Lee, Daley, Nadler, "Isolated human follicular dendritic cells display a unique antigenic phenotype," *J. Exp. Med*, 169:2043–2058, 1989.

Schwab, Chavany, Duroux, Goubin, Lebeau, Helene, Saison-Behmoaras, "Antisense oligonucleotides adsorbed to polyalkylcyanoacrylate nanoparticles specifically inhibit mutated Ha-ras-mediated cell proliferation and tumorigenicity in nude mice," *Proc. Natl. Acad. Sci. USA*, 91(22):10460–10464, 1994.

Sculier et al., "Pilot study of amphotericin B entrapped in sonicated liposomes in cancer patients with fungal infections," *J. Cancer Clin. Oncol.*, 24(3):527–538, 1988.

Seeger, Batz, Orum, "PNA-mediated purification of PCR™ amplifiable human genomic DNA from whole blood," *Biotechniques*, 23(3):512–517, 1997.

Segal, "Biochemical Calculations," 2nd Edition, John Wiley & Sons, New York, 1976.

Severinson, Bergstedt-Lindqvist, van der Loo, Fernandez, "Characterization of the IgG response induced by polyclonal B cell activators," *Immunol. Rev.*, 67:73–85, 1982.

Sharma and Srikant, "G protein coupled receptor signaled apoptosis is associated with activation of a cation insensitive acidic endonuclease and intracellular acidification," *Biochem. Biophys. Res. Commun.*, 242:134–140, 1998.

Sharma and Srikant, "Induction of wild-type p53, Bax, and acidic endonuclease during somatostatin-signaled apoptosis in MCF-7 human breast cancer cells," *Int. J. Cancer*, 76:259–266, 1998.

Sharma, Patel, Srikant, "Subtype-selective induction of wild-type p53 and apoptosis, but not cell cycle arrest, by human somatostatin receptor 3," *Mol. Endocrinol.*, 10:1688–1696, 1996.

Shimizu and Honjo, "Immunoglobulin class switching," *Cell*, 36:801–803, 1984.

Shimizu, Takahashi, Yaoita, Honjo, "Organization of the constant-region gene family of the mouse immunoglobulin heavy chain," *Cell*, 28:499–506, 1982.

Shiokawa, Ohyama, Yamada, Takahashi, Tanuma, "Identification of an endonuclease responsible for apoptosis in rat thymocytes," *Eur. J. Biochem.*, 226:23–30, 1994.

Shockett and Stavnezer, "Inhibitors of poly(ADP-ribose) polymerase increase antibody class switching," *J. Immunol.*, 151:6962–6976, 1993.

Shparago, Zelazowski, Jin, McIntyre, Stuber, Pecanha, Kehry, Mond, Max, Snapper, "IL-10 selectively regulates murine Ig isotype switching," *Int. Immunol.*, 8:781–790, 1996.

Siebenkotten, Esser, Wabl, Radbruch, "The murine IgG1/IgE class switch program," *Eur. J. Immunol.*, 22:1827–1834, 1992.

Snapper and Mond, "Towards a comprehensive view of immunoglobulin class switching," *Immunol. Today*, 14:15–17, 1993.

Snapper, Zelazowski, Rosas, Kehry, Tian, Baltimore, Sha, "B cells from p50/NF-kappa B knockout mice have selective defects in proliferation, differentiation, germline CH transcription, and Ig class switching," *J. Immunol.*, 156:183–191, 1996.

Song, Rothe, Goeddel, "The tumor necrosis factor-inducible zinc finger protein A20 interacts with TRAF1/TRAF2 and inhibits NF-kappaB activation," *Proc. Natl. Acad. Sci. USA*, 93:6721–6725, 1996.

Spanopoulou, Roman, Corcoran, Schlissel, Silver, Nemazee, Nussenzweig, Shinton, Hardy, Baltimore, "Functional immunoglobulin transgenes guide ordered B-cell differentiation in Rag-1-deficient mice," *Genes Develop.*, 8:1030–1042, 1994.

Stanhope-Baker, Hudson, Shaffer, Constantinescu, Schlissel, "Cell type-specific chromatin structure determines the targeting of V(D)J recombinase activity in vitro," *Cell*, 85:887–897, 1996.

Stanton and Marcu, "Nucleotide sequence and properties of the murine gamma 3 immunoglobulin heavy chain gene switch region: implications for successive C gamma gene switching," *Nucl. Acids Res.*, 10:5993–6006, 1982.

Stavnezer-Nordgren and Sirlin, "Specificity of immunoglobulin heavy chain switch correlates with activity of germline heavy chain genes prior to switching," *EMBO J.* 5:95–102, 1986.

Stratling, Grade, Horz, "Ca/Mg-dependent endonuclease from porcine liver. Purification, properties, and sequence specificity," *J. Biol. Chem.*, 259:5893–5898, 1984.

Sulston, "Post-embryonic development in the ventral cord of *Caenorhabditis elegans*," *Philos. Trans. R. Soc. Lond. B. Biol. Sci.*, 275:287–297, 1976.

Suzuki, Shin, Fjuikura, Matsuzaki, Takata, "Direct gene transfer into rat liver cells by in vivo electroporation," *FEBS Lett.*, 425(3):436–440, 1998.

Szurek, Petrini, Dunnick, "Complete nucleotide sequence of the murine gamma 3 switch region and analysis of switch recombination sites in two gamma 3-expressing hybridomas," *J. Immunol.*, 135:620–626, 1985.

Taccioli, Cheng, Varghese, Whitmore, Alt, "A DNA repair defect in Chinese hamster ovary cells affects V(D)J recombination similarly to the murine scid mutation," *J. Biol. Chem.*, 269:7439–7442, 1994.

Taccioli, Gottlieb, Blunt, Priestley, Demengeot, Mizuta, Lehmann, Alt, Jackson, Jeggo, "Ku80: product of the XRCC5 gene and its role in DNA repair and V(D)J recombination," *Science*, 265:1442–1445, 1994.

Taccioli, Rathbun, Oltz, Stamato, Jeggo, Alt, "Impairment of V(D)J recombination in double-strand break repair mutants," *Sci.*, 160:207–210, 1993.

Taccioli, Rathbun, Shinkai, Oltz, Cheng, Whitmore, Stamato, Jeggo, Alt, "Activities involved in V(D)J recombination," *Curr. Top. Microbiol. Immunol.*, 182:107–114, 1992.

Takakura, "Drug delivery systems in gene therapy," *Nippon Rinsho*, 56(3):691–695, 1998.

Takenaga, Serizawa, Azechi, Ochiai, Kosaka, Igarashi, Mizushima, "Microparticle resins as a potential nasal drug delivery system for insulin," *J. Controller Release*, 52(1–2):81–87, 1998.

Takeuchi, Rothe, Goeddel, "Anatomy of TRAF2. Distinct domains for nuclear factor-kappaB activation and association with tumor necrosis factor signaling proteins," *J. Biol. Chem.*, 271:19935–19942, 1996.

Temin, "Retrovirus vectors for gene transfer: Efficient integration into and expression of exogenous DNA in vertebrate cell genome," *In: Gene Transfer*, Kucherlapati (ed.), Plenum Press, New York, pp. 149–188, 1986.

Thiede, Bayerdorffer, Blasczyk, Wittig, Neubauer, "Simple and sensitive detection of mutations in the ras proto-oncogenes using PNA-mediated PCR™ clamping," *Nuc. Acids Res.*, 24(5):983–984, 1996.

Tomkinson and Linn, "Purification and properties of a single strand-specific endonuclease from mouse cell mitochondria," *Nucl. Acids Res.*, 14:9579–9593, 1986.

Torriglia, Chaudun, Chany-Fournier, Jeanny, Courtois, Counis, "Involvement of DNase II in nuclear degeneration during lens cell differentiation," *J. Biol. Chem.*, 270:28579–28585, 1995.

Torriglia, Chaudun, Courtois, Counis, "On the use of $Zn^{2+}$ to discriminate endonucleases activated during apoptosis," *Biochimie*, 79:435–438, 1997.

Truong-Le, August, Leong, "Controlled gene delivery by DNA-gelatin nanopspheres," *Hum. Gene Ther.*, 9(12):1709–1717, 1998.

Tur-Kaspa et al., "Use of electroporation to introduce biologically active foreign genes into primary rat hepatocytes," *Mol. Cell Biol.*, 6:716–718, 1986.

Tsubata, Wu, Honjo, "B-cell apoptosis induced by antigen receptor crosslinking is blocked by a T-cell signal through CD40," *Nature*, 364:645–648, 1993.

Tsuzuki, Fujii, Sakumi, Tominaga, Nakao, Sekiguchi, Matsushiro, Yoshimura, Morita, "Targeted disruption of the Rad51 gene leads to lethality in embryonic mice," *Proc. Natl. Acad. Sci. USA*, 93:6236–6240, 1996.

Uckun, Schieven, Dibirdik, Chandan-Langlie, Tuel-Ahlgren, Ledbetter, "Stimulation of protein tyrosine phosphorylation, phosphoinositide turnover, and multiple previously unidentified serine/threonine-specific protein kinases by the Pan-B-cell receptor CD40/Bp50 at discrete developmental stages of human B-cell ontogeny," *J. Biol. Chem.*, 266:17478–17485, 1991.

Van Cott, Lubon, Russell, Butler, Gwazdauskas, Knight, Drohan, Velander, "Phenotypic and genotypic stability of multiple lines of transgenic pigs expressing recombinant human protein C," *Transgenic Res.*, 6(3):203–212, 1997.

Vanbever, Fouchard, Jadoul, De Morre, Preat, Marty, "In vivo noninvasive evaluation of hairless rat skin after high-voltage pulse exposure," *Skin Parmacol. Appl. Skin Physiol.*, 11(1):23–34, 1998.

Vasanthakumar and Ahmed, "Modulation of drug resistance in a daunorubicin resistant subline with oligonucleoside methylphosphonates," *Cancer Commun.*, 1(4):225–232, 1989.

Vassilatis, Despommier, Misek, Polvere, Gold, Van der Ploeg, "Analysis of a 43-kDa glycoprotein from the intracellular parasitic nematode Trichinella spiralis," *J. Biol. Chem.*, 267(26):18459–65, 1992.

Ventura et al., *Nucl. Acids Res.*, 21:3249–55, 1993.

Veselkov, Demidov, Frank-Kamenetskii, Nielsen, "PNA as a rare genome-cutter," *Nature*, 379(6562):214, 1996.

Vickers, Griffith, Ramasamy, Risen, Freier, "Inhibition of NF-kappa B specific transcriptional activation by PNA strand invasion," *Nucl. Acids Res.*, 23(15):3003–3008, 1995.

Vidal, Morris, Chaloin, Heitz, Divita, "New strategy for RNA vectorization in mammalian cells. Use of a peptide vector," *C.R. Acad. Sci. III*, 320(4):279–87, 1997.

Vieira and Messing, "The pUC plasmids, an M13mp7-derived system for insertion mutagenesis and sequencing with synthetic universal primers," *Gene* 19:259–268, 1982.

Villalba, Ferrari, Bozza, Del Senno, Di Virgilio, "Ionic regulation of endonuclease activity in PC12 cells, *Biochem. J.*, 311:1033–1038, 1995.

von Schwedler, Jack H. M, Wabl, "Circular DNA is a product of the immunoglobulin class switch rearrangement," *Nature*, 345:452–456, 1990.

Wagner, E., Zatloukal., K., Cotten, M., Kirlappos, H., Mechtler, K., Curiel, D. T., and Birnstiel, M. L., "Coupling of adenovirus to transferrin-polylysine/DNA complexes greatly enhances receptor-mediated gene delivery and expression of transfected genes," *Proc. Natl. Acad. Sci. USA* 89(13):6099–6103, 1992.

Walker and Sikorska, "New aspects of the mechanism of DNA fragmentation in apoptosis," *Biochem. Cell Biol.*, 75:287–299, 1997.

Wang and Furth, "Mammalian endonuclease, DNase V. Purification and properties of enzyme of calf thymus," *J. Biol. Chem.*, 252:116–124, 1977.

Wang, Furth, Rose, "Purification and characterization of a DNA single strand specific endonculease from human cells," *Biochem.*, 17:544–549, 1978.

Wang, Lu, Chen, Liao, "Porcine spleen deoxyribonuclease II. Covalent structure, cDNA sequence, molecular cloning, and gene expression," *J. Biol. Chem.*, 273:17192–17198, 1998.

Warren and Berton, "Induction of germ-line gamma 1 and epsilon Ig gene expression in murine," *J. Immunol.*, 155:5637–5646, 1995.

Waters, Saikh, Stavnezer, "A B-cell-specific nuclear protein that binds to DNA sites 5' to immunoglobulin S alpha tandem repeats is regulated during differentiation," *Mol. Cell Biol.*, 9:5594–5601, 1989.

Waterston and Brenner, "A suppressor mutation in the nematode acting on specific alleles of many genes," *Nature*, 275:715–719, 1978.

Weeda, Donker, de Wit, Morreau H, Janssens, Vissers, Nigg, van Steeg, Bootsma, Hoeijmakers, "Disruption of mouse ERCC1 results in a novel repair syndrome with growth failure, nuclear abnormalities and senescence," *Curr. Biol.*, 7:427–439, 1997.

Wess, J., "G-protein-coupled receptors: molecular mechanisms involved in receptor activation and selectivity of G-protein recognition, *FASEB J.*, 11:346–354, 1997.

White, Word, Humphries, Blattner, Tucker, "Immunoglobulin D switching can occur through homologous recombination in human B cells," *Mol. Cell. Biol.*, 10:3690–3699, 1990.

Wielbo, Sernia, Gyurko, Phillips, "Antisense inhibition of hypertension in the spontaneously hypertensive rat," *Hypertension*, 25(3):314–319, 1994.

Wielbo, Simon, Phillips, Toffolo, "Inhibition of hypertension by peripheral administration of antisense oligodeoxynucleotides," *Hypertension*, 28(1): 147–151, 1995.

Wielbo, Shi, Sernia, "Antisense inhibition of angiotensinogen in hepatoma cell culture is enhanced by cationic liposome delivery," *Biochem. Biophy. Research Comm.*, 232:794–799, 1997.

Williams and Maizels, "LR1, a lipopolysaccharide-responsive factor with binding sites in the immunoglobulin switch regions and heavy-chain enhancer," *Genes Develop.*, 5:2353–2361, 1991.

Williams, Hanakahi, Maizels, "Purification and properties of LR1, an inducible DNA binding protein from mammalian B lymphocytes," *J. Biol. Chem.*, 268:13731–13737, 1993.

Williams, Hanakahi, Maizels, "Purification and properties of LR1, an inducible DNA binding protein," *J. Biol. Chem.*, 268:13731–13737, 1993.

Wills, Gesteland, Barnett, Bolten, Waterston, "The genes sup-7 X and sup-5 III of *C. elegans* suppress amber nonsense mutations via altered transfer RNA, *Cell*, 33:575–583, 1983.

Wills, Gesteland, Karn, Barnett, Bolten, Waterston, "The genes sup-7 X and sup-5 III of *C. elegans* suppress amber nonsense mutations via altered transfer RNA," *Cell*, 33:575–583, 1983.

Wilson, Mochon, Boxer, "Induction of bcl-2 expression by phosphorylated CREB proteins during B-cell activation and rescue from apoptosis," *Mol. Cell Biol.*, 16:5546–5556, 1996.

Wohlrab, McLean, Wells, "The segment inversion site of herpes simplex virus type 1 adopts a novel DNA structure," *J. Biol. Chem.*, 262(13):6407–16, 1987.

Wolf, Modrow, Motz, Jameson, Hermann, Fortsch, "An integrated family of amino acid sequence analysis programs," *Comput. Appl. Biosci.*, 4(1):187–91, 1988.

Wong, T. E., and Neumann, E., "Electric field mediated gene transfer," *Biochim. Biophys. Res. Commun.* 107(2):584–587, 1982.

Worm and Geha, "CD40-mediated lymphotoxin alpha expression in human B cells is tyrosine kinase dependent," *Eur. J. Immunol.*, 25:2438–2444, 1995.

Wu and Wu, "Receptor-mediated in vitro gene transfections by a soluble DNA carrier system," *J. Biol. Chem.*, 262:4429–4432, 1987.

Wu and Wu, "Evidence for targeted gene delivery to HepG2 hepatoma cells in vitro," *Biochemistry*, 27:887–892, 1988.

Wuerffel, Jamieson, Morgan, Merkulov, Sen, Kenter, "Switch recombination breakpoints are strictly correlated with DNA recognition motifs for immunoglobulin S gamma 3 DNA-binding proteins," *J. Exp. Med.*, 176:339–349, 1992.

Wuerffel, Nathan, Kenter, "Detection of an immunoglobulin switch region-specific DNA-binding protein in mitogen-stimulated mouse splenic B cells," *Mol. Cell Biol.*, 10:1714–1718, 1990.

Wyatt, Rudders, Zelenetz, Delellis, Krontiris, "BCL2 oncogene translocation is mediated by a chi-like consensus," *J. Exp. Med.*, 175:1575–1588, 1992.

Xu and Stavnezer, "Regulation of transcription of immunoglobulin germ-line gamma 1 RNA: analysis of the promoter/enhancer," *EMBO J.*, 11:145–155, 1992.

Xu, Gorham, Li, Bottaro, Alt, Rothman, "Replacement of germ-line epsilon promoter by gene targeting alters control of immunoglobulin heavy chain class switching," *Proc. Natl. Acad. Sci. USA*, 90:3705–3709, 1993.

Xu, Kim, Marcu, "Properties of B cell stage specific and ubiquitous nuclear factors binding to immunoglobulin heavy chain gene switch regions," *Int. Immunol.*, 4:875–887, 1992.

Yancopoulos, DePinho, Zimmerman, Lutzker, Rosenberg, Alt, "Secondary genomic rearrangement events in pre-B cells: VHDJH replacement by a LINE-1 sequence and directed class switching,". *EMBO J.*, 5:3259–3266, 1986.

Yang et al., "In vivo and in vitro gene transfer to mammalian somatic cells by particle bombardment," *Proc. Natl. Acad. Sci. USA*, 87:9568–9572, 1990.

Yashihara, Tanigawa, Koide, "Inhibition of rat liver $Ca^{2+}$, $Mg^{2+}$-dependent endonuclease activity by nicotinamide adenine dinucleotide and poly(adenosine diphosphate ribose) synthase," *Biochem. Biophys. Res. Commun.*, 59:658–665, 1974.

Yasuda, Takeshita, Iida, Nakajima, Hosomi, Nakashima, Kishi, "Molecular cloning of the cDNA encoding human deoxyribonuclease II.," *J. Biol. Chem.*, 273:2610–2616, 1998.

Yoshihara, Tanaka, Hashida, Ura, Kamiya, Tanigawa, Koide, "Stimulation of bull seminal $Ca^{2+}$, $Mg^{2+}$-dependent endonuclease by various DNA-binding proteins," *Biochem. Biophys. Res. Commun.*, 106:803–810, 1982.

Young, Ardman, Shinkai, Lansford, Blackwell, Mendelsohn, Rolink, Melchers, Alt, "Influence of immunoglobulin heavy- and light-chain expression on B-cell differentiation," *Genes Develop.*, 8:1043–1057, 1994.

Zambaux, Bonneaux, Gref, Maincent, Dellacherie, Alonso, Labrude, Vigneron, "Influence of experimental paparmeters on the characteristics of poly(lactic acid) nanoparticles prepared by a double emulsion method," *J. Controlled Release*, 50(1–3):31–40, 1998.

Zhang, Bottaro, Li, Stewart, Alt, "A selective defect in IgG2b switching as a result of targeted mutation," *EMBO J.*, 12:3529–3537, 1993.

Zhang, Cheah, Saxon, "Secondary deletional recombination of rearranged switch region in Ig isotype-switched B cells. A mechanism for isotype stabilization," *J. Immunol.*, 154:2237–2247, 1995.

Zhang, Mills, Saxon, "Switch circles from IL-4-directed epsilon class switching from human B lymphocytes. Evidence for direct, sequential., and multiple step sequential switch from mu to epsilon Ig heavy chain gene," *J. Immunol.*, 152:3427–3435, 1994.

zur Muhlen, Schwarz, Mehnert, "Solid lipid nanoparticles (SLN) for controlled drug delivery—drug release and release mechanism," *Eur. J. Pharm. Biopharm.*, 45(2):149–155, 1998.

Zwaal, Broeks, van Meurs, Groenen, Plasterk, "Target-selected gene inactivation in Caenorhabditis elegans by using a frozen transposon insertion mutant bank," *Proc. Natl. Acad. Sci. USA.*, 90:7431–7435, 1993.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An isolated nucleic acid molecule encoding a murine endonuclease-SR protein, wherein the nucleic acid molecule comprises the nucleotide sequence of SEQ ID NO:1, or comprises a nucleic acid fragment of SEQ ID NO:1, and said fragment encodes a protein having endonuclease-SR biological activity.

2. A vector comprising the nucleic acid molecule of claim 1.

3. The vector of claim 2, wherein said vector is a plasmid, cosmid, phagemid, virus, baculovirus, yeast artificial chromosome, bacterial artificial chromosome or phage.

4. The vector of claim 3, wherein said virus is an adenovirus, an adenoassociated virus, a retrovirus, a Herpes virus, or a vaccinia virus.

5. A host cell comprising the vector of claim 2.

6. The host cell of claim 5, further defined as a bacterial cell.

7. The host cell of claim 6, wherein said bacterial cell is an E. coli, Pseudomonas sp. or salmonella cell.

8. The host cell of claim 5, further defined as a eukaryotic cell.

9. The host cell of claim 8, further defined as an animal cell, a yeast cell, or a fungal cell.

10. The host cell of claim 9, wherein said animal cell is a human, mouse, rat, monkey, chicken, dog, cat, horse, pig, cow, sheep, goat or hamster cell.

11. The host cell of claim 9, wherein said animal cell is a cancer cell.

12. The host cell of claim 11, wherein said cancer cell is a tumor cell.

13. A method of preparing a polypeptide, comprising the steps of:
   (a) culturing the host cell of claim 5 under conditions effective to allow expression of the encoded polypeptide; and
   (b) collecting said polypeptide so expressed.

14. A nucleic acid detection kit comprising, in suitable container means, the nucleic acid molecule of claim 1 and a detection reagent.

15. A method for detecting a nucleotide sequence encoding an endonuclease-SR polypeptide, comprising the steps of:
   (a) obtaining nucleic acids from a sample, the nucleic acids in the sample encoding an endonuclease-SR polypeptide;
   (b) contacting said nucleic acids from the sample with a nucleic acid probe comprising a nucleotide sequence complementary to SEQ ID NO:1, or a nucleotide sequence complementary to a fragment of SEQ ID NO:1, under conditions effective to form a complex; and
   (c) detecting the complex so formed.

16. A method of detecting an endonuclease-SR polypeptide-encoding polynucleotide, said method comprising the steps of:
   (a) obtaining nucleic acids from a sample suspected of containing an endonuclease-SR polypeptide-encoding polynucleotide;
   (b) hybridizing said nucleic acids with a labeled probe comprising at least 25 contiguous nucleotides of SEQ ID NO:1; and
   (c) detecting in the sample the pretsence of compltxes between said nucleic acids and said probe, wherein the presence of said complexes is indicative of the presence of said endonuclease-SR polypeptide-encoding polynucleotide, or fragments thereof.

* * * * *